(12) United States Patent
Spence

(10) Patent No.: US 9,463,268 B2
(45) Date of Patent: Oct. 11, 2016

(54) CANNULA SYSTEMS AND METHODS

(76) Inventor: Paul A. Spence, Louisville, KY (US)

(*) Notice: Subject to any disclaimer, the term of this patent is extended or adjusted under 35 U.S.C. 154(b) by 1043 days.

(21) Appl. No.: 13/227,272

(22) Filed: Sep. 7, 2011

(65) Prior Publication Data

US 2012/0059213 A1 Mar. 8, 2012
US 2012/0259157 A9 Oct. 11, 2012

Related U.S. Application Data

(60) Provisional application No. 61/459,055, filed on Dec. 6, 2010, provisional application No. 61/402,892, filed on Sep. 7, 2010.

(51) Int. Cl.
*A61M 5/00* (2006.01)
*A61M 1/36* (2006.01)
*A61B 17/11* (2006.01)

(52) U.S. Cl.
CPC ..... *A61M 1/3653* (2013.01); *A61B 2017/1135* (2013.01); *A61M 1/3659* (2014.02)

(58) Field of Classification Search
CPC .... A61M 1/22; A61M 1/101; A61M 1/1008; A61M 1/3659; A61M 1/3653; A61B 2017/1135
USPC .................................. 604/7, 8, 264; 600/16
See application file for complete search history.

(56) References Cited

U.S. PATENT DOCUMENTS

| | | |
|---|---|---|
| 2,935,068 A | 5/1960 | Donaldson |
| 3,195,540 A | 7/1965 | Waller |
| 3,818,511 A * | 6/1974 | Goldberg ............ A61M 1/3659 264/257 |
| 3,942,535 A | 3/1976 | Schulman |
| 4,014,317 A | 3/1977 | Bruno |
| 4,080,958 A | 3/1978 | Bregman et al. |

(Continued)

FOREIGN PATENT DOCUMENTS

| | | |
|---|---|---|
| FR | 1 514 319 | 2/1968 |
| WO | WO 82/01644 A1 | 5/1982 |

(Continued)

OTHER PUBLICATIONS

Antaki, J. F. et al., "Development progress of the University of Pittsburgh streamliner: a mixed flow blood pump with magnetic bearings," ASAIO Journal, 46(2):194 (2000) (Abstract only).

(Continued)

*Primary Examiner* — Leslie Deak
*Assistant Examiner* — Ariana Zimbouski
(74) *Attorney, Agent, or Firm* — Lerner, David, Littenberg, Krumholz & Mentlik, LLP

(57) ABSTRACT

Disclosed herein is a cannula assembly for directing the flow of material from an organ chamber, e.g., blood from the left chamber of the heart, and methods of placing the cannula assembly in fluidic communication with the chamber. The cannula assembly includes an elongate tubular member and a coupling assembly disposed at the distal end of elongate tubular member. The elongate tubular member includes a lumen extending from a distal opening at the distal end to a proximal opening at the proximal end. The coupling assembly includes a retaining element and a retention member configured to cooperate with each other and with the portion of the organ wall surrounding the opening in the wall to couple or anchor cannula system to the wall and to provide fluidic communication between the distal opening of the elongate tubular member and the organ chamber.

13 Claims, 49 Drawing Sheets

(56) References Cited

U.S. PATENT DOCUMENTS

| | | |
|---|---|---|
| 4,116,589 A | 9/1978 | Rishton |
| 4,366,819 A | 1/1983 | Kaster |
| 4,790,825 A | 12/1988 | Bernstein et al. |
| 4,994,078 A | 2/1991 | Jarvik |
| 4,995,857 A | 2/1991 | Arnold |
| 5,163,954 A | 11/1992 | Curcio et al. |
| 5,171,207 A | 12/1992 | Whalen |
| 5,171,218 A | 12/1992 | Fonger et al. |
| 5,190,528 A | 3/1993 | Fonger et al. |
| 5,287,852 A | 2/1994 | Arkinstall |
| 5,290,227 A | 3/1994 | Pasque |
| 5,290,251 A | 3/1994 | Griffith |
| 5,312,341 A | 5/1994 | Turi |
| 5,338,301 A | 8/1994 | Diaz |
| 5,344,385 A | 9/1994 | Buck et al. |
| 5,344,443 A | 9/1994 | Palma et al. |
| 5,449,342 A | 9/1995 | Hirose et al. |
| 5,545,191 A | 8/1996 | Mann et al. |
| 5,653,676 A | 8/1997 | Buck et al. |
| 5,676,670 A | 10/1997 | Kim |
| 5,695,471 A | 12/1997 | Wampler |
| 5,697,936 A | 12/1997 | Shipko et al. |
| 5,701,919 A | 12/1997 | Buck et al. |
| 5,704,891 A | 1/1998 | Mussivand |
| 5,711,753 A | 1/1998 | Pacella et al. |
| 5,738,649 A | 4/1998 | Macoviak |
| 5,741,316 A | 4/1998 | Chen et al. |
| 5,743,845 A | 4/1998 | Runge |
| 5,840,070 A | 11/1998 | Wampler |
| 5,858,009 A | 1/1999 | Jonkman |
| 5,904,666 A | 5/1999 | DeDecker et al. |
| 5,921,971 A | 7/1999 | Agro et al. |
| 5,924,848 A | 7/1999 | Izraelev |
| 5,924,975 A | 7/1999 | Goldowsky |
| 5,938,412 A | 8/1999 | Izraelev |
| 5,941,813 A | 8/1999 | Sievers et al. |
| 5,944,745 A | 8/1999 | Rueter |
| 5,947,892 A | 9/1999 | Benkowski et al. |
| 5,948,006 A | 9/1999 | Mann |
| 5,965,089 A | 10/1999 | Jarvik et al. |
| 5,984,857 A | 11/1999 | Buck et al. |
| 6,001,056 A | 12/1999 | Jassawalla et al. |
| 6,017,355 A | 1/2000 | Hessel et al. |
| 6,116,862 A | 9/2000 | Rau et al. |
| 6,132,363 A | 10/2000 | Freed et al. |
| 6,186,999 B1 | 2/2001 | Chen |
| 6,273,861 B1 | 8/2001 | Bates et al. |
| 6,299,575 B1 | 10/2001 | Bolling |
| 6,328,699 B1 | 12/2001 | Eigler et al. |
| 6,354,299 B1 | 3/2002 | Fischell et al. |
| 6,358,266 B1 | 3/2002 | Bonutti |
| 6,406,420 B1 * | 6/2002 | McCarthy et al. ............ 600/16 |
| 6,428,464 B1 | 8/2002 | Bolling |
| 6,471,633 B1 | 10/2002 | Freed |
| 6,511,412 B1 | 1/2003 | Freed et al. |
| 6,530,876 B1 | 3/2003 | Spence |
| 6,565,536 B1 | 5/2003 | Sohn |
| 6,579,223 B2 | 6/2003 | Palmer |
| 6,669,708 B1 | 12/2003 | Nissenbaum et al. |
| 6,723,039 B2 | 4/2004 | French et al. |
| 6,808,508 B1 | 10/2004 | Zafirelis et al. |
| 6,889,082 B2 | 5/2005 | Bolling et al. |
| 6,926,662 B1 | 8/2005 | Aboul-Hosn et al. |
| 6,955,175 B2 | 10/2005 | Stevens et al. |
| 6,994,094 B2 | 2/2006 | Schwartz |
| 6,994,666 B2 | 2/2006 | Shannon et al. |
| 7,037,253 B2 | 5/2006 | French et al. |
| 7,048,681 B2 | 5/2006 | Tsubouchi et al. |
| 7,056,294 B2 | 6/2006 | Khairkhahan et al. |
| 7,077,801 B2 | 7/2006 | Haverich |
| 7,169,164 B2 | 1/2007 | Borillo et al. |
| 7,214,230 B2 | 5/2007 | Brock et al. |
| 7,273,446 B2 | 9/2007 | Spence |
| 7,288,104 B2 | 10/2007 | Heil, Jr. |
| 7,340,288 B1 | 3/2008 | Karicherla et al. |
| 7,473,239 B2 | 1/2009 | Wang et al. |
| 7,520,850 B2 | 4/2009 | Brockway |
| 7,585,290 B2 | 9/2009 | Kathrani et al. |
| 7,666,203 B2 | 2/2010 | Chanduszko et al. |
| 7,766,813 B2 | 8/2010 | Spence |
| 7,785,246 B2 | 8/2010 | Aboul-Hosn et al. |
| 7,881,807 B2 * | 2/2011 | Schaer .......... 607/122 |
| 7,905,823 B2 | 3/2011 | Farnan et al. |
| 8,092,364 B2 | 1/2012 | Spence |
| 8,157,720 B2 | 4/2012 | Marseille et al. |
| 8,308,715 B2 | 11/2012 | Farnan et al. |
| 8,333,686 B2 | 12/2012 | Marseille et al. |
| 8,333,687 B2 | 12/2012 | Farnan et al. |
| 8,333,727 B2 | 12/2012 | Farnan |
| 8,343,029 B2 | 1/2013 | Farnan et al. |
| 8,394,010 B2 | 3/2013 | Farnan |
| 8,460,168 B2 | 6/2013 | Farnan |
| 8,465,410 B2 | 6/2013 | Marseille et al. |
| 8,512,012 B2 | 8/2013 | Akdis et al. |
| 8,545,379 B2 | 10/2013 | Marseille et al. |
| 8,545,380 B2 | 10/2013 | Farnan et al. |
| 8,607,800 B2 | 12/2013 | Thapliyal et al. |
| 8,784,291 B2 | 7/2014 | Farnan et al. |
| 2002/0082614 A1 | 6/2002 | Logan et al. |
| 2002/0151761 A1 | 10/2002 | Viole et al. |
| 2002/0173693 A1 | 11/2002 | Landesberg |
| 2003/0069468 A1 | 4/2003 | Bolling et al. |
| 2003/0088147 A1 | 5/2003 | Bolling et al. |
| 2003/0139643 A1 | 7/2003 | Smith et al. |
| 2003/0176760 A1 | 9/2003 | El Oakley et al. |
| 2004/0116992 A1 | 6/2004 | Wardle et al. |
| 2004/0147803 A1 | 7/2004 | Hegde et al. |
| 2006/0009737 A1 | 1/2006 | Whiting et al. |
| 2007/0049787 A1 | 3/2007 | Nose et al. |
| 2007/0106315 A1 | 5/2007 | Gregoric et al. |
| 2007/0197855 A1 | 8/2007 | Richardson et al. |
| 2007/0233041 A1 | 10/2007 | Gellman |
| 2008/0076959 A1 | 3/2008 | Farnan et al. |
| 2008/0076960 A1 * | 3/2008 | Marseille et al. ............... 600/16 |
| 2008/0243081 A1 | 10/2008 | Nance |
| 2009/0023975 A1 * | 1/2009 | Marseille ........... A61B 17/3421 600/16 |
| 2009/0112050 A1 * | 4/2009 | Farnan et al. ................... 600/16 |
| 2009/0182188 A1 | 7/2009 | Marseille et al. |
| 2010/0010500 A1 | 1/2010 | Beane et al. |
| 2010/0160725 A1 | 6/2010 | Kiser et al. |
| 2010/0185044 A1 | 7/2010 | Kassab et al. |
| 2010/0198040 A1 | 8/2010 | Friedman et al. |
| 2010/0249490 A1 * | 9/2010 | Farnan .................. A61M 1/101 600/16 |
| 2010/0249491 A1 | 9/2010 | Farnan et al. |
| 2010/0249920 A1 | 9/2010 | Bolling et al. |
| 2011/0054487 A1 | 3/2011 | Farnan |
| 2011/0066170 A1 | 3/2011 | Farnan |
| 2011/0112353 A1 | 5/2011 | Farnan et al. |
| 2011/0112632 A1 | 5/2011 | Chau et al. |
| 2011/0137234 A1 | 6/2011 | Farnan et al. |
| 2011/0190697 A1 | 8/2011 | Farnan |
| 2011/0196190 A1 | 8/2011 | Farnan et al. |
| 2011/0196191 A1 | 8/2011 | Farnan et al. |
| 2011/0200451 A1 | 8/2011 | Lehmann et al. |
| 2012/0004496 A1 | 1/2012 | Farnan et al. |
| 2012/0078032 A1 | 3/2012 | Spence |
| 2012/0116317 A1 | 5/2012 | Kassab et al. |
| 2012/0259157 A9 | 10/2012 | Spence |
| 2013/0060267 A1 | 3/2013 | Farnan et al. |
| 2013/0116715 A1 | 5/2013 | Weber |
| 2013/0150772 A1 | 6/2013 | Farnan et al. |
| 2013/0172661 A1 | 7/2013 | Farnan et al. |
| 2013/0231521 A1 | 9/2013 | Farnan |
| 2014/0107399 A1 | 4/2014 | Spence |
| 2015/0223839 A1 | 8/2015 | Spence et al. |

FOREIGN PATENT DOCUMENTS

| | | |
|---|---|---|
| WO | WO 97/42413 A1 | 11/1997 |
| WO | WO 99/59652 A1 | 11/1999 |
| WO | WO 01/80927 A2 | 11/2001 |
| WO | WO 2005/037345 A2 | 4/2005 |

(56) References Cited

FOREIGN PATENT DOCUMENTS

| WO | WO 2007/047933 A2 | 4/2007 |
|---|---|---|
| WO | WO 2008/027869 A2 | 3/2008 |
| WO | WO 2009/045624 A1 | 4/2009 |
| WO | WO 2009/055651 A1 | 4/2009 |
| WO | WO 2013/022420 | 2/2013 |

OTHER PUBLICATIONS

Antaki, J. F. et al., "In vivo evaluation of the nimbus axial flow ventricular assist system: Criteria and methods," ASAIO Journal, 39:M231-M236 (1993).

Arrow International, Inc., AutoCAT™2WAVE™, Brochure, Arrow International, Inc. USA (2003), 4 pages.

Baird, R. J. et al., Le Support Mecanique Du Ventricule Gauche, L'Union Med. du Canada, Tome 93, pp. 258-268 (1964).

Brooks, S. G. et al., "The use of a latissimus dorsi myocutaneous flap to cover an axillobifemoral vascular prosthetic graft," Eur. J. Vasc. Surg., 3:367-368 (1989).

Cavallaro, A. et al., "The effect of body weight compression on axillo-femoral by-pass patency," J. Cardiovasc. Surgery, 29:476-479 (1988).

Cochran, R. P. et al., "Ambulatory intraaortic balloon pump use as bridge to heart transplant," Ann. Thorac. Surg., 74:746-752 (2002).

Copeland, J. G. III, "Thromboembolism and bleeding: Clinical strategies," Ann. Thorac. Surg., 61:376-377 (1996).

Datascope, The CS100(TM) Intelligent Counterpulsation, Brochure (2003), 11 pages.

Dennis, C. et al., "Clinical Use of a Cannula for Left Heart Bypass Without Thoracotomy: Experimental Protection Against Fibrillation by Left Heart Bypass," Annals of Surgery, 156(4):623-636 (1962).

Dennis, C. et al., "Reducation of the Utilization of the Heart by Left Heart Bypass," Circulation Research, Journal of the American Heart Association, 10:298-305 (1962).

Dennis, C. et al., "Left atrial cannulation without thoracotomy for total left heart bypass," Acta Chir Scand., 123:267-279 (1962).

El-Banayosy, A. et al., "Bridging to cardiac transplantation with the thoratec ventricular assist device," Thorac. Cardiovasc. Surg., 47:307-310 (1999).

Fraser, K. H. et al., "Computational fluid dynamics analysis of thrombosis potential in left ventricular assist device drainage cannulae," ASAIO Journal, 56(3):157-163 (2010).

Freed, P. S. et al., "Intraaortic balloon pumping for prolonged circulatory support," The American Journal of Cardiology, 61(8):554-557 (1988).

Greenberg, B. et al., "Effects of continuous aortic flow augmentation in patients with exacerbation of heart failure inadequately responsive to medical therapy: Results of the multicenter trial of the orqis medical cancion system for the enhanced treatment of heart failure unresponsive to medical therapy (momentum)," Circulation, 118:1241-1249 (2008).

Gristina, A. G. et al., "Biomaterial-centered sepsis and the total artificial heart," JAMA, 259:870-874 (1988).

Helman, D. N. et al., "Left ventricular assist device bridge-to-transplant network improves survival after failed cardiotomy," Ann. Thorac. Surg., 68:1187-1194 (1999).

Jaski, B. E. et al., "Diagnosis and treatment of complications in patients implanted with a TCI left ventricular assist device," Journal of Interventional Cardiology, 8(3):275-282 (1995).

Jeevanadam, V. et al., "Circulatory assistance with a permanent implantable IABP: Initial human experience," Circulation, 106(1):I-183-I-188 (2002).

Johnson, W. C. et al., "Is axillo-bilateral femoral graft an effective substitute for aortic-bilateral Iliac/femoral graft?: An analysis of ten years experience," Annals of Surgery, 186(2):123-129 (1977).

Kawahito, K. et al., "Ex vivo phase 1 evaluation of the DeBakey/NASA axial flow ventricular assist device," Artificial Organs, 20(1):47-52 (1996).

Kawai, A. et al., "Management of infections in mechanical circulatory support devices," Cardiac Surgery: State of the Art Reviews, 7(2):413-424 (1993).

Kirklin, J. K. et al., "Mechanical circulatory support: Registering a therapy in evolution," Circ. Heart Fail., 1:200-205 (2008).

Korfer, R. et al., "Temporary pulsatile ventricular assist devices and biventricular assist devices," Ann. Thorac. Surg., 68:678-683 (1999).

Litwak, K. N. et al., "Retrospective analysis of adverse events in preclinical ventricular assist device experiments," ASAIO Journal, 54:1-4 (2008).

Magee, T. R. et al., "Reinforced vascular grafts: a comparative study," Eur. J. Vasc. Surg., 6:21-25 (1992).

MaGovern, G. J. et al., "The biopump and postoperative circulatory support," Ann. Thorac. Surg., 55:245-249 (1993).

Manord, J. D. et al., "Implications for the vascular surgeon with prolonged (3 to 89 days) intraaortic balloon pump counterpulsation," J. Vasc. Surg., 26:511-516 (1997).

McBride, L. R. et al., "Clinical experience with 111 thoratec ventricular assist devices," Ann. Thorac. Surg., 67:1233-1239 (1999).

Morales, D. L. S. et al., "Lessons learned from the first application of the DeBakey VAD child: An intracorporeal ventricular assist device for children," The Journal of Heart and Lung Transplantation, 24(3):331-337 (2005).

Mussivand, T. et al., "Progress with the heartsaver ventricular assist device," Ann. Thorac. Surg., 68:785-789 (1999).

Nanas, J. N. et al., "A valveless high stroke volume counterpulsation device restores hemodynamics in patients with congestive heart failure and intractable cardiogenic shock awaiting heart transplantation," The Journal of Thoracic and Cardiovascular Surgery, 111(1):55-61 (1996).

Nanas, J. N. et al., "Comparison of an implanted abdominal aortic counterpulsation device with the intraaortic balloon pump in a heart failure model," J. Am College Cardiology, 7(5):1028-1035 (1986).

Nanas, J. N. et al., "Effectiveness of a counterpulsation device implanted on the ascending aorta," Trans. Am. Soc. Artif. Intern. Organs, 33:203-206 (1987).

Nanas, J. N. et al., "Hemodynamic effects of a counterpulsation device implanted on the ascending aorta in severe cardiogenic shock," Trans. Am. Soc. Artif. Intern. Organs, 34:229-234 (1988).

Nanas, J. N. et al., "Preclinical evaluation of the abdominal aortic counterpulsation device," American Heart Journal, 116(4):1003-1008 (1998).

Noon, G. P. et al., "Clinical experience with the micromed DeBakey ventricular assist device," Ann. Thorac. Surg., 71:S133-S138 (2001).

Nose, Y. et al., "Can we develop a nonpulsatile permanent rotary blood pump? Yes, we can," Artificial Organs, 20(6):467-474 (1996).

Ochiai, Y. et al., "In vivo hemodynamic performance of the cleveland clinic coraide blood pump in calves," Ann. Thorac. Surg., 72:747-752 (2001).

Ozawa, K. et al., "Inflow system for long-term ventricular assist device (LVAD)," In: Transactions American Society for Artificial Internal Organs, vol. XXVI, New Orleans, Louisiana, Apr. 17-19, 1980, pp. 24-28.

Park, J. K. et al., "Intraaortic balloon pump management of refractory congestive heart failure in children," Pediatric Cardiology, 14(1):19-22 (1993).

Reddy, R. C. et al., "End organ function with prolonged nonpulsatile circulatory support," ASAIO Journal, 41:M547-M551 (1995).

Rosenbaum, A. M. et al., "Intra-aortic balloon counterpulsation as a 'bridge'•to cardiac transplantation. Effects in nonischemic and ischemic cardiomy opathy," Chest, 106(6):1683-1688 (1994).

Schmid, C. et al., "Influence of inflow cannula length in axial-flow pumps on neurologic adverse event rate:Results from a multi-center analysis," The Journal of Heart and Lung Transplantation, 27(3):253-260 (2008).

Slater, J. P. et al., "Low thromboembolic risk without anticoagulation using advanced-design left ventricular assist devices," Ann. Thorac Surg., 62:1321-1328 (1996).

Sunshine Heart, Inc. Prospectus, Underwriter Wilson HTM Corporate Finance Limited (2004), 116 pages.

(56) References Cited

OTHER PUBLICATIONS

Tayama, E. et al., "The DeBakey ventricular assist device: current status in 1997," Artificial Organs, 23(12):1113-1116 (1999).
Terrovitis, J. V. et al., "Superior performance of a paraaortic counterpulsation device compared to the intraaortic balloon pump," World Journal of Surgery, 27(12):1311-1316 (2003).
Zile, M. R. et al., "Progressive improvement in cardiac performance with continuous aortic flow augmentation (aortic flow therapy) in patients hospitalized with severe heart failure: Results of the multicenter trial of the orqis medical cancion system for the enhanced treament of heart failure unresponsive to medical therapy (momentum)," The Journal of Heart and Lung Transplantation, 29(1):86-92 (2010).
International Search Report for International Application No. PCT/US2001/040579, mailed Nov. 15, 2001, 4 pages.
International Preliminary Examination Report for International Application No. PCT/US2001/040579, dated Jul. 15, 2002, 7 pages.
Office Action for U.S. Appl. No. 14/055,485, mailed Apr. 7, 2014, 6 pages.
Antaki et al., "An improved left ventricular cannula for chronic dynamic blood pump support," *Artif Organ* 19(7):671-675 (1995) (Abstract only).
Bachman, "Development and Evaluation of the Quintessential Ventricular Cannula," *MS Thesis*, University of Pittsburgh (2008).
Baird et al., "Survey of Mechanical Assistance of the Circulation and the Present Status of Left-Heart Bypass," pp. 340-345 (1965).
"Cannula-Tip Development for Minimal Invasive Pumps,"Medizinische Universitate Wien, Center for Medical Phsics and Biomedical Engineering as printed on Jan. 31, 2011.
Curtis et al, "Novel ventricular apical vannula: in vitro evaluation using transparent, compliant ventricular casts," *ASAIO J.* 44(5):M691-M695 (1998) (Abstract only).
DeBakey, "The Artificial Heart," The History of Surgery in Houston, Kenneth L. Maitox, ed., pp. 346-358 (1998).
International Search Report mailed on Nov. 30, 2011, in International Application No. PCT/US2011/050709.

Kyo et al., "Percutaneous Introduction of Left Atrial Cannula for Left Heart Bypass: Utility of Biplane Transesophageal Echocardiographic Guidance for Transseptal Puncture," *Artif Organs*, 16(4): 386-391 (1992).
Macha et al., "Survival for Up to Six Months in Calves Supported With an Implantable Axial Flow Ventricular Assist Device," *ASAIO Journal*, 43:311-315 (1997).
Nishimura et al., "Results of Chronic Animal Experiments With a New Version of a Magnetically Suspended Centrifugal Pump," *ASAIO Journal*, 44:M725-M727 (1998).
Petition to Request Inter Partes Reexamination of U.S. Pat. No. 6,530,876, filed on Dec. 19, 2011.
Takami et al., "Anatomical Consideration for an Implantable Centrifugal Biventricular Assist System," *Artif Organs*, 21(10):1132-1136 (1997).
World Heart Corporation, *World Heart*, 1998 Annual Report.
Meyns et al., "Proof of Concept: Hemodynamic Response to Long-Term Partial Ventricular Support With the Synergy Pocket Micro-Pump", *JACC*, 54(1):79-86 (2009).
Office Action for Chinese Application No. 201180051436.8, dated Feb. 15, 2015, 13 pages.
Office Action for U.S. Appl. No. 14/055,485, mailed Dec. 10, 2014, 9 pages.
International Search Report and Written Opinion for International Application No. PCT/US2013/065277, mailed Jan. 9, 2014, 11 pages.
International Search Report and Written Opinion for International Application No. PCT/US2014/068626, mailed Apr. 30, 2015, 12 pages.
Office Action for Israel Application No. 225104, dated Mar. 27, 2016.
Office Action for U.S. Appl. No. 14/055,485, mailed Sep. 22, 2015, 10 pages.
Final Office Action for U.S. Appl. No. 14/055,485, mailed May 18, 2016, 10 pages.

\* cited by examiner

TO PATIENT'S HEAD

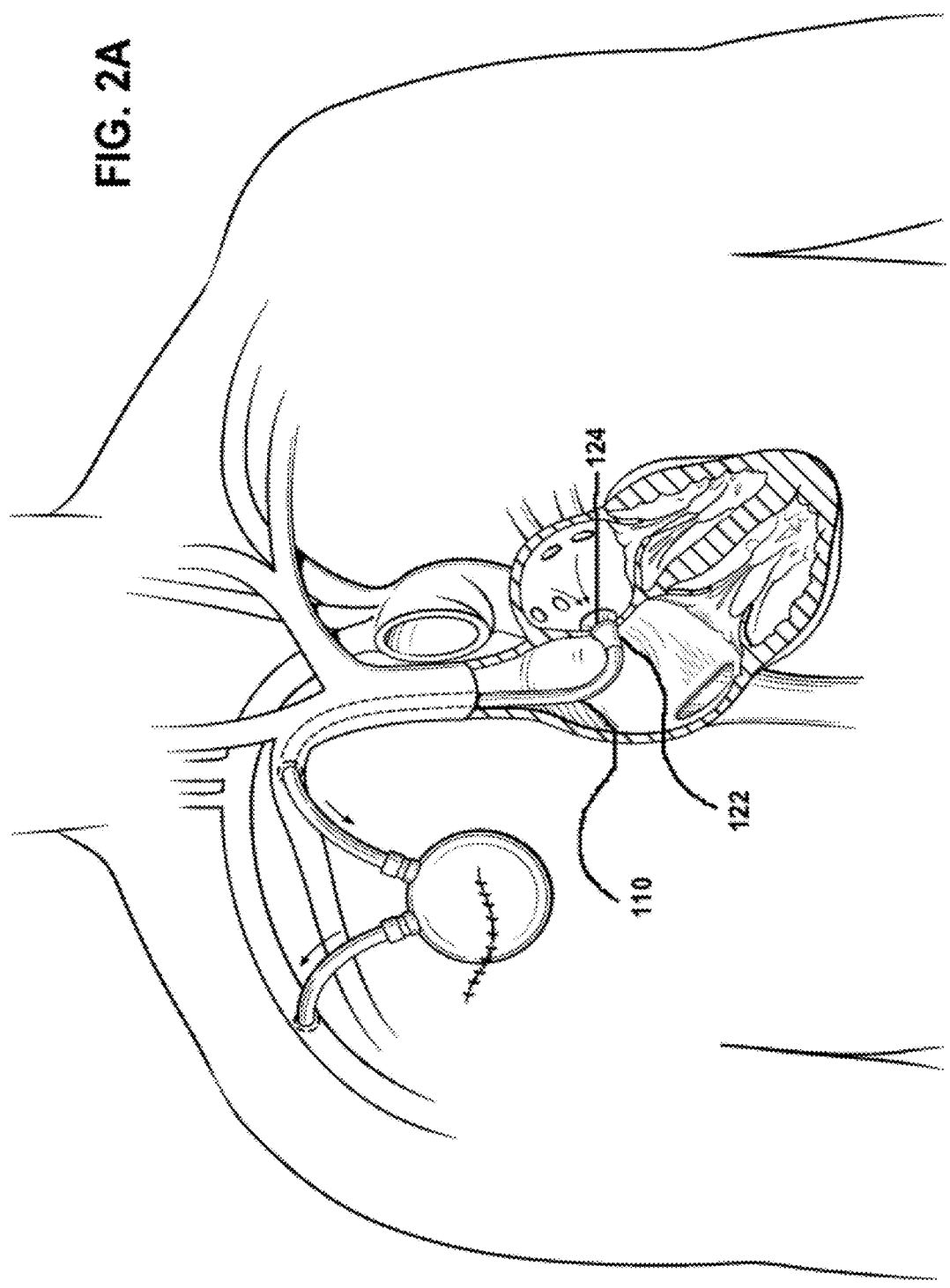

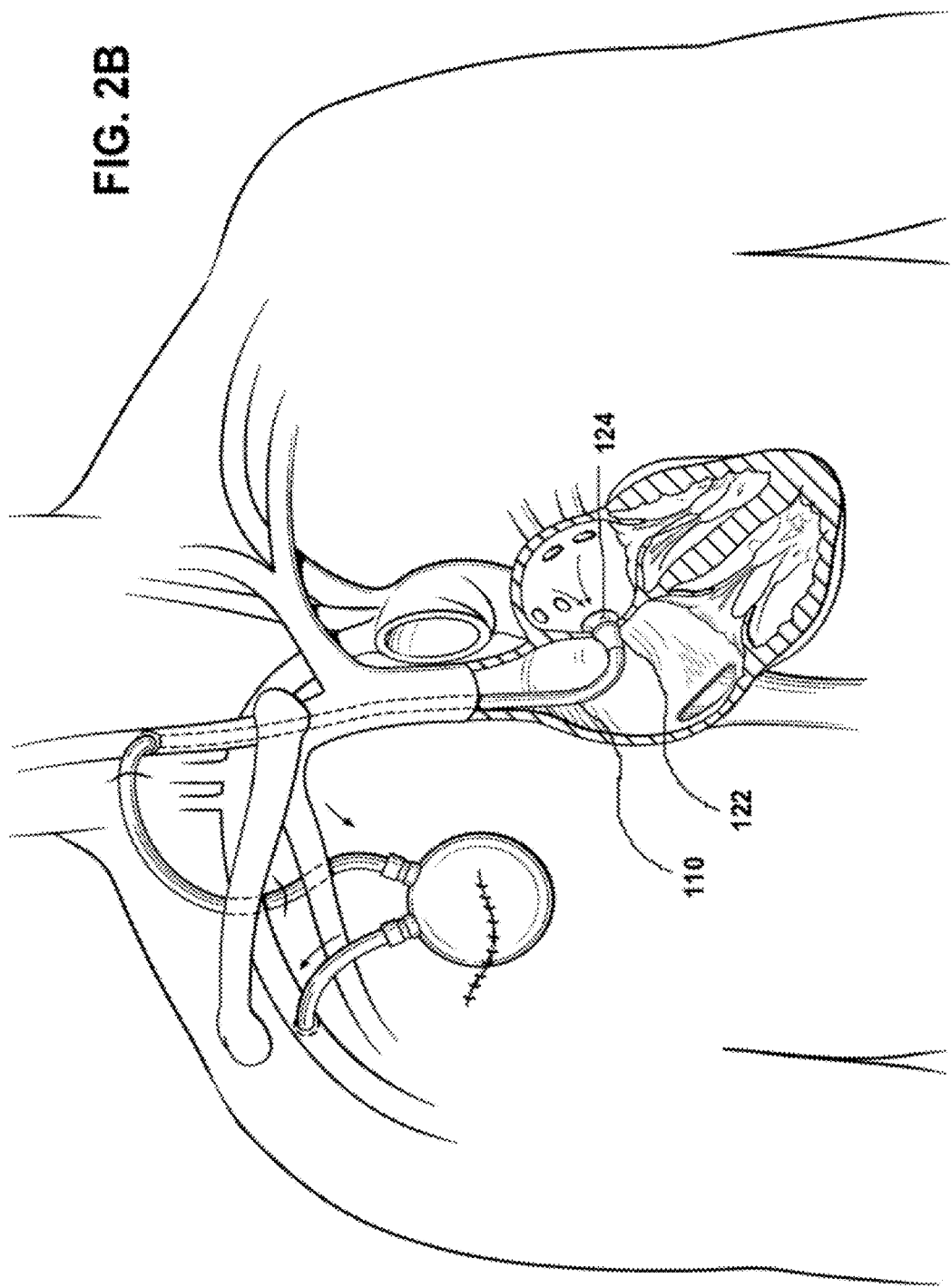

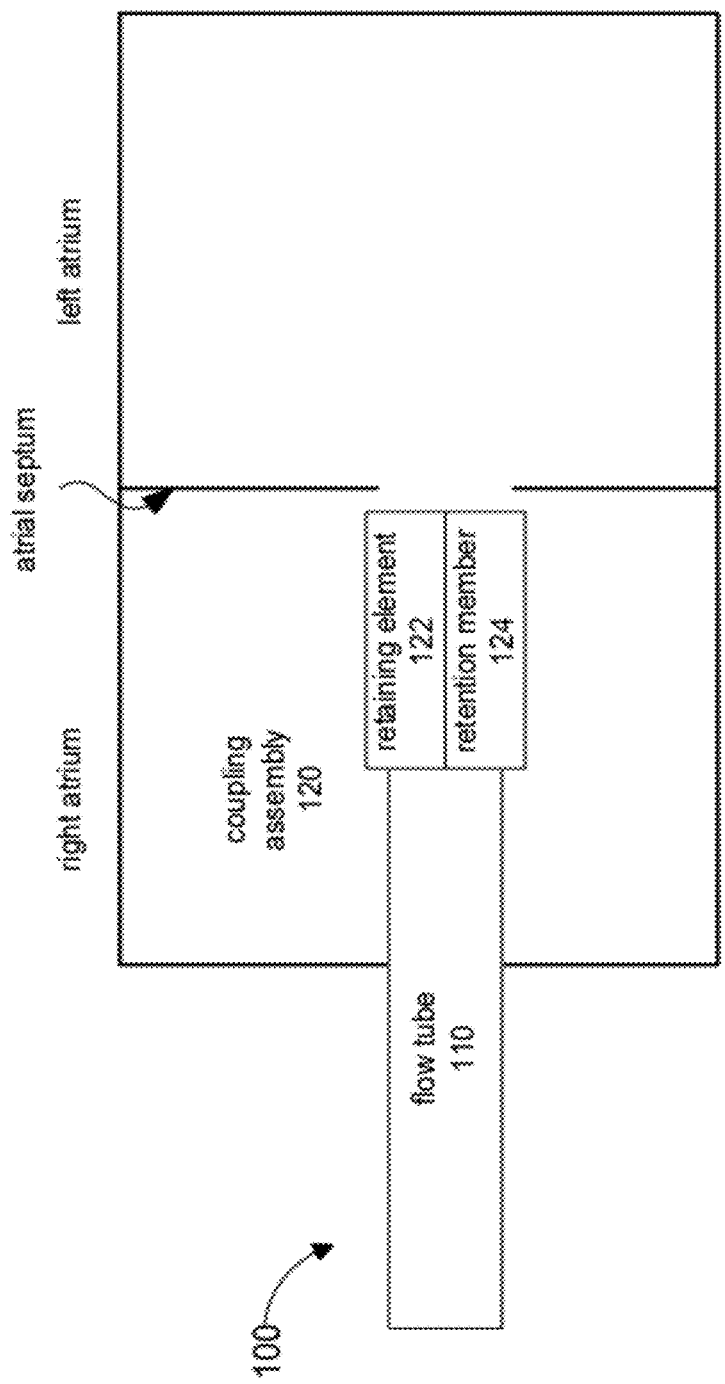

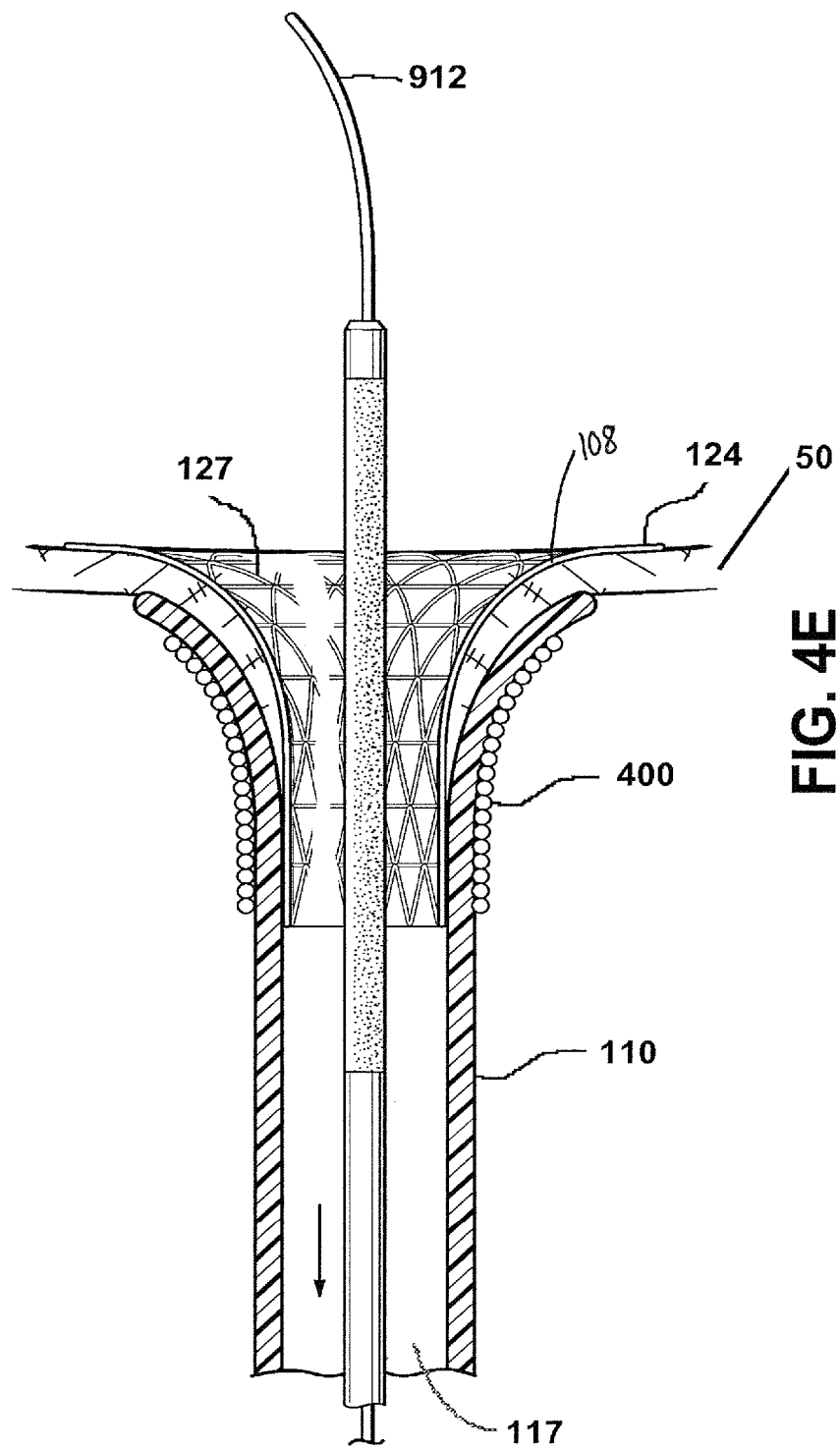

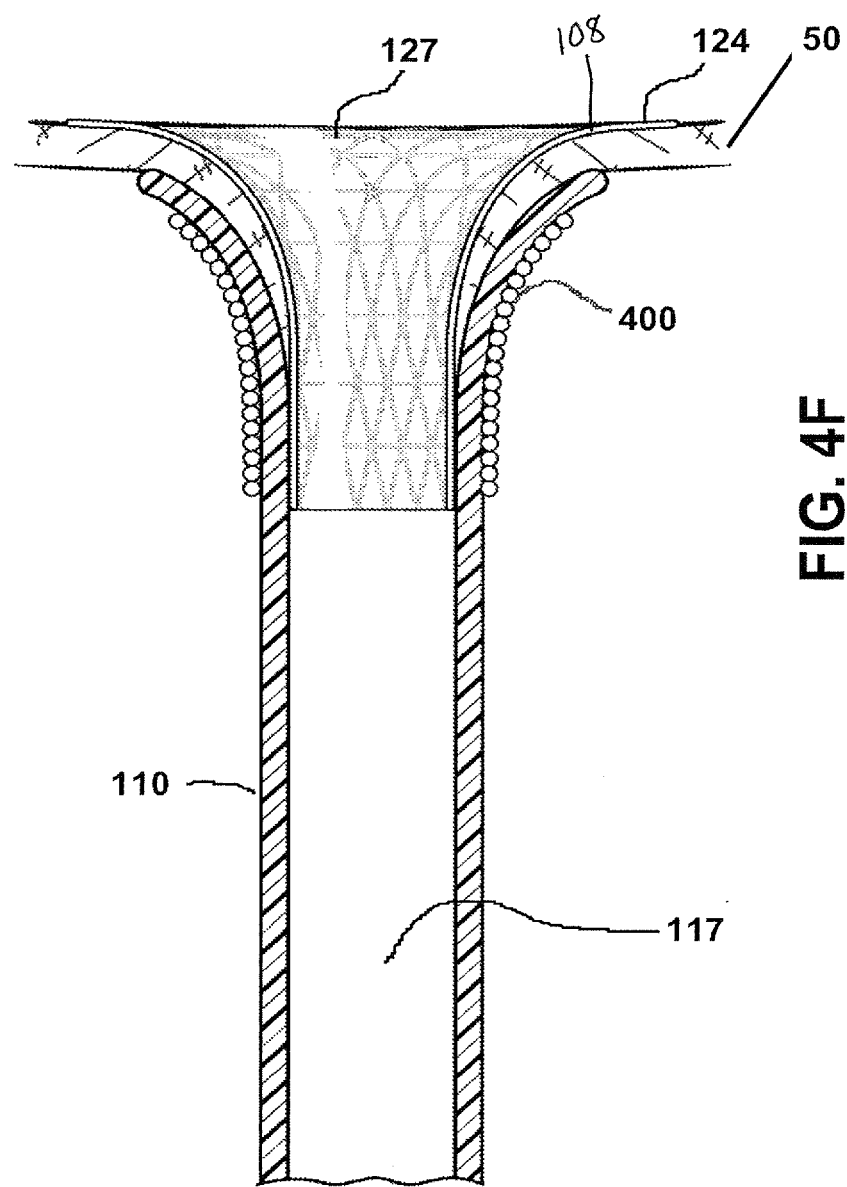

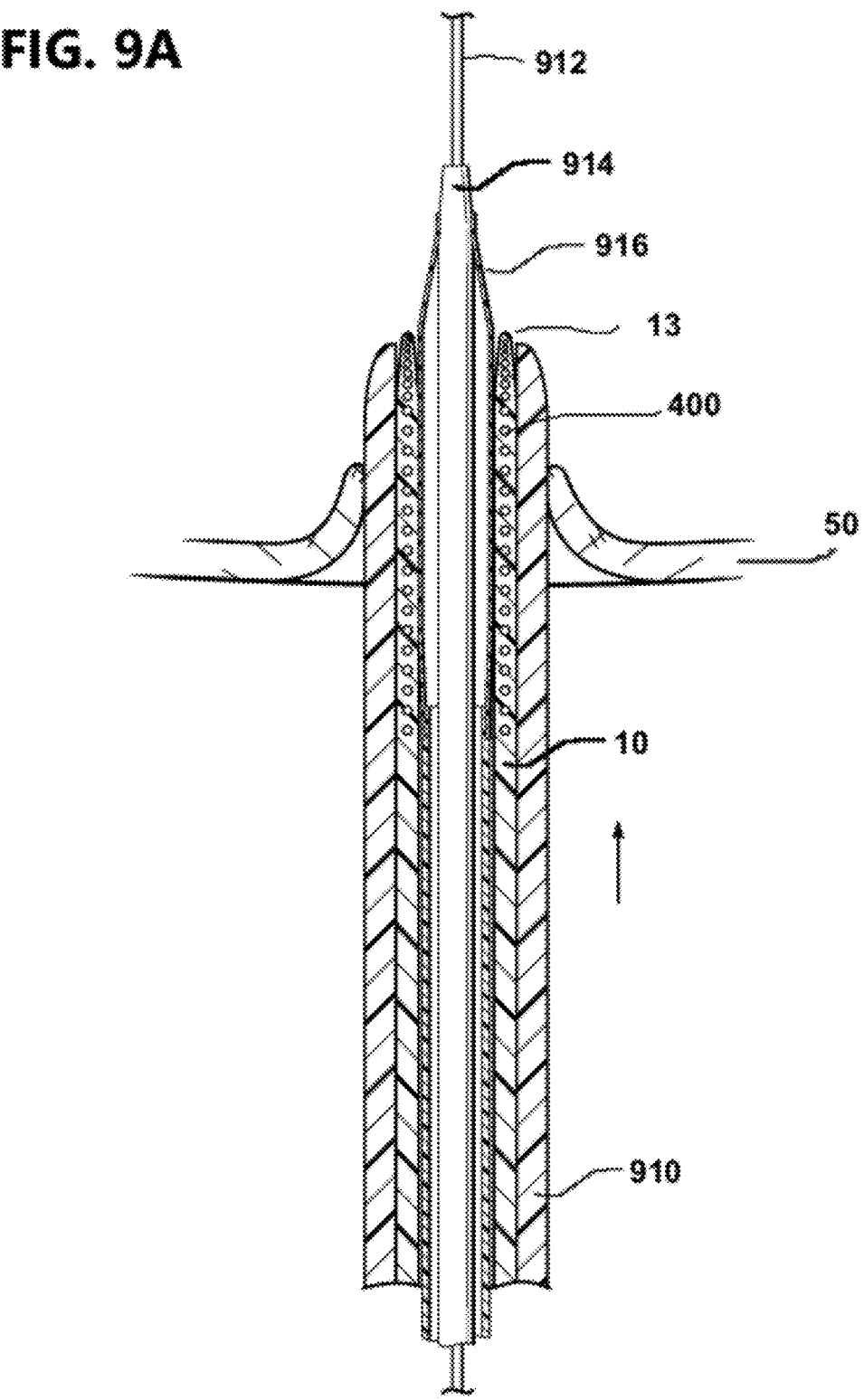

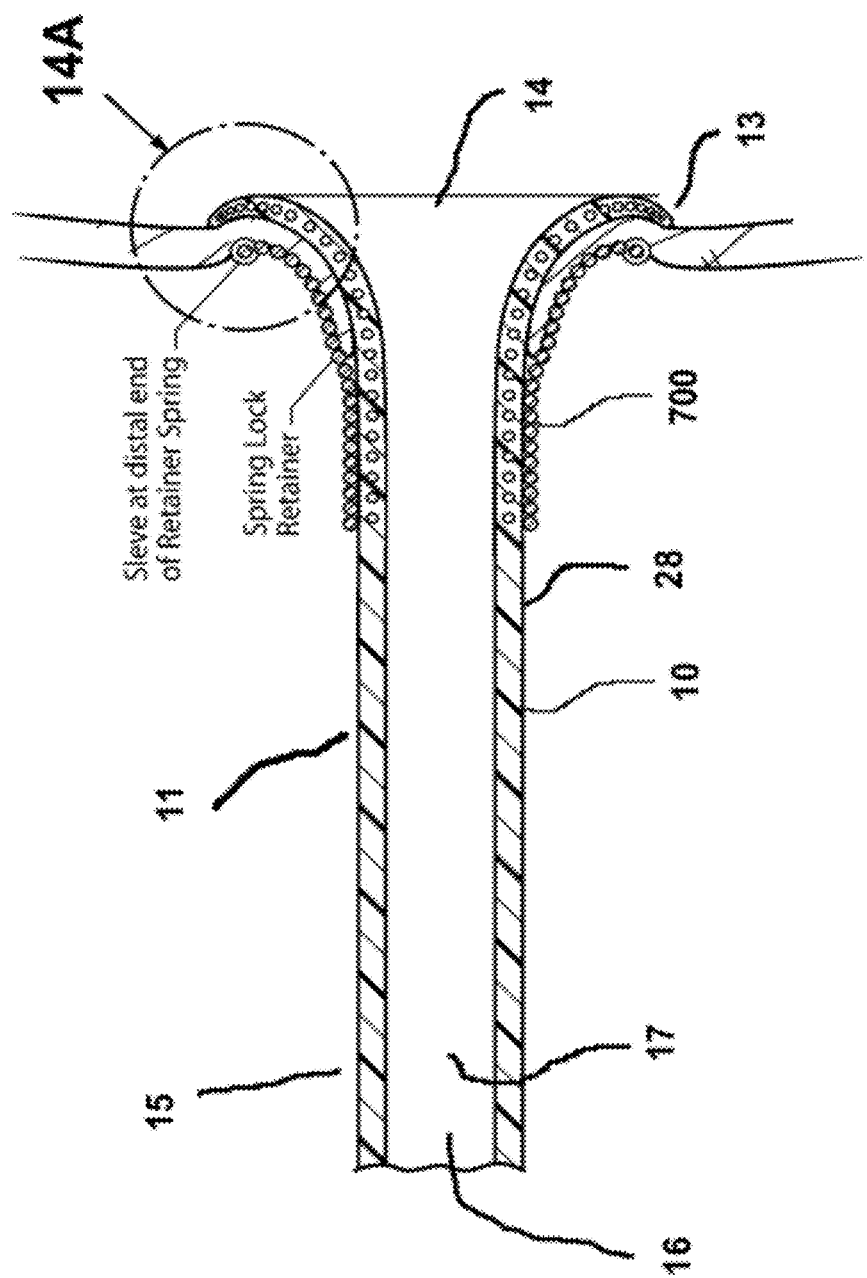

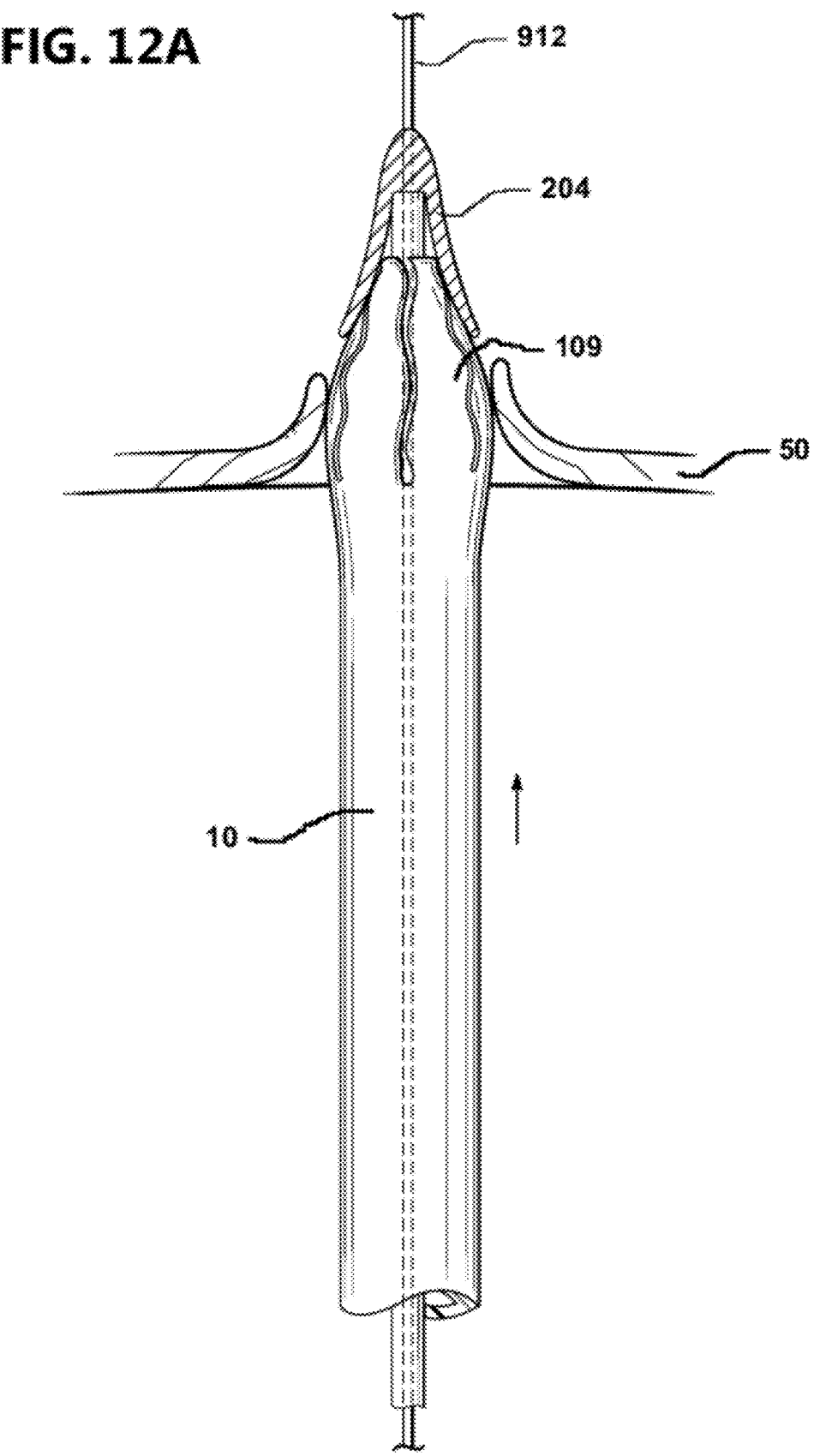

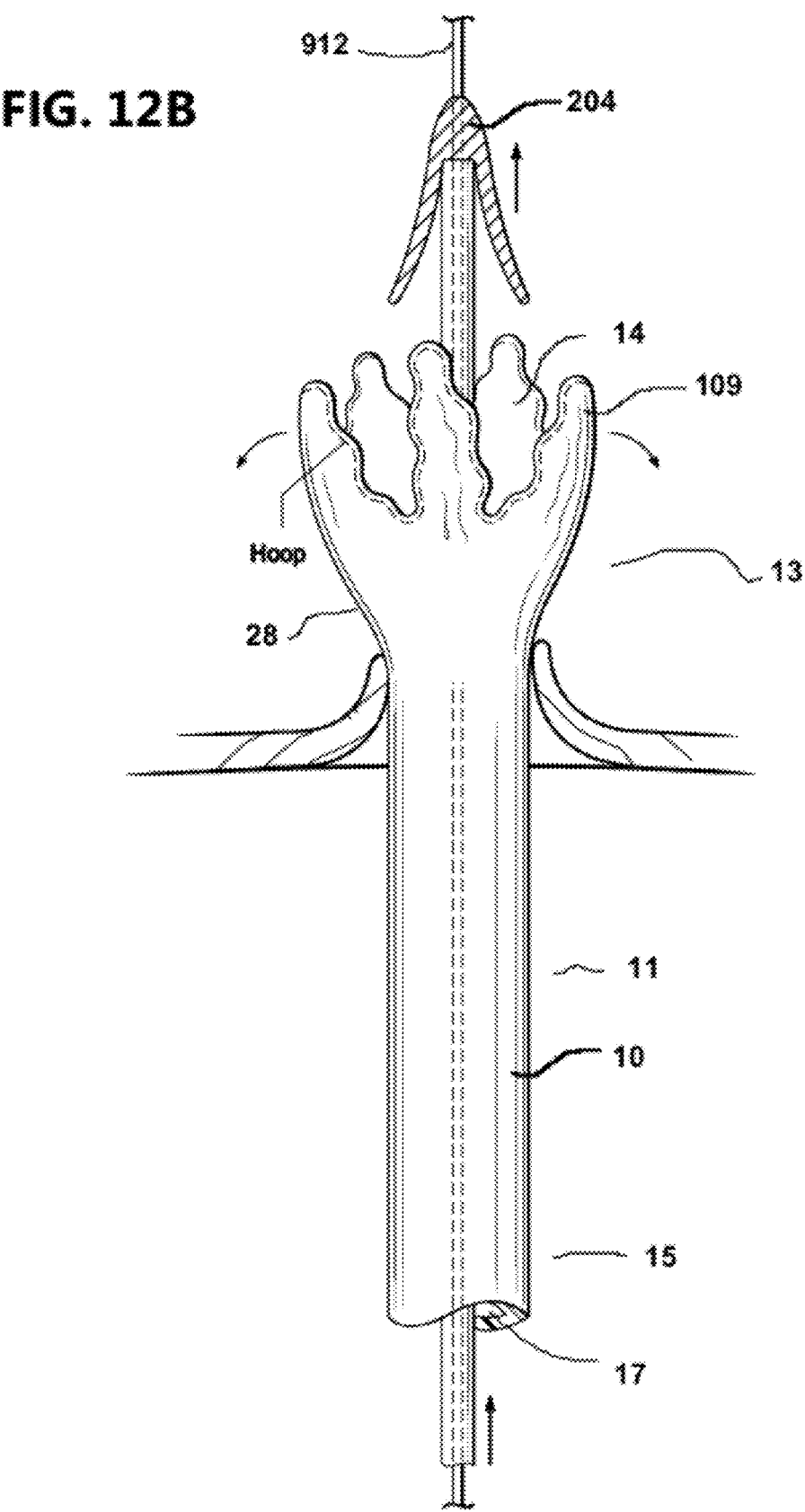

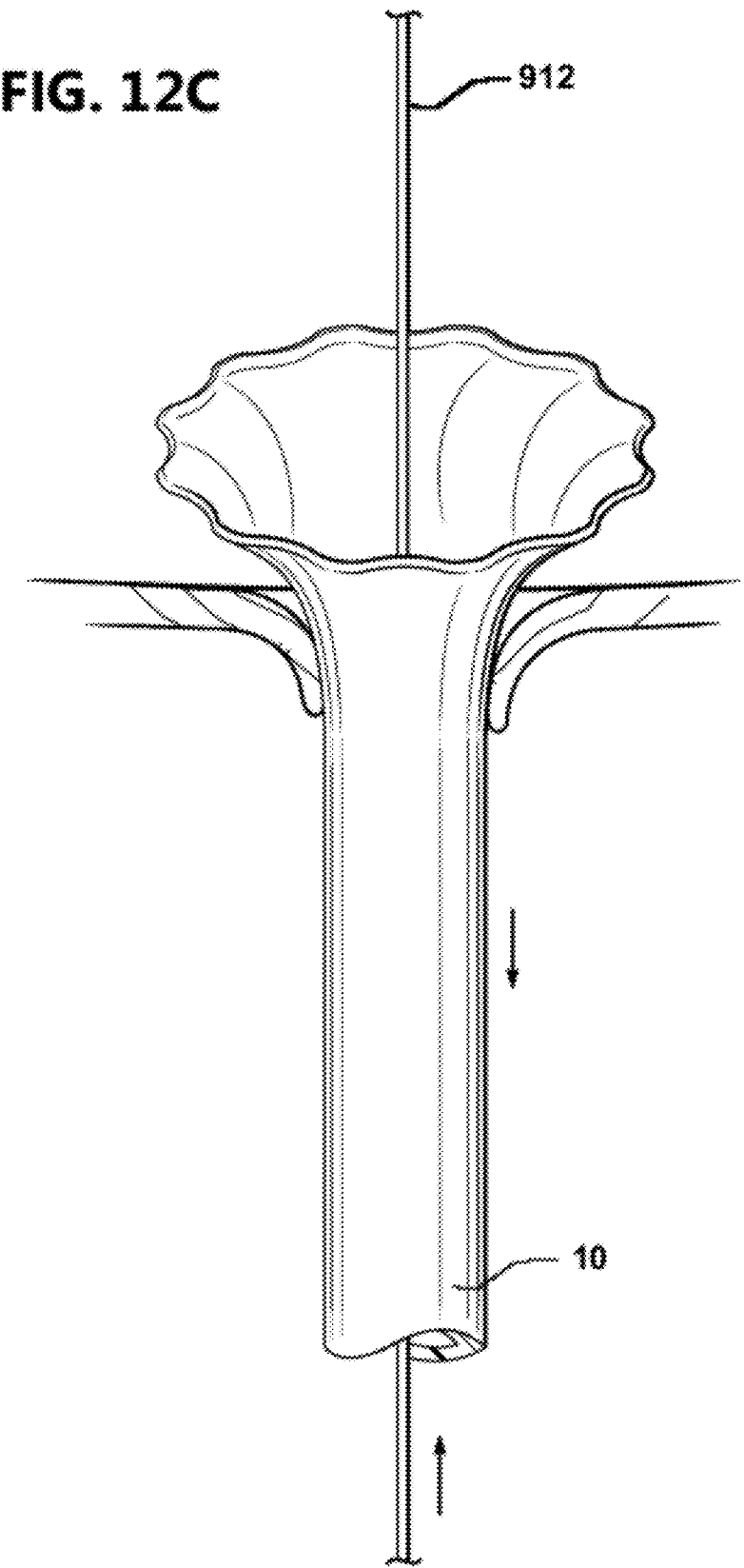

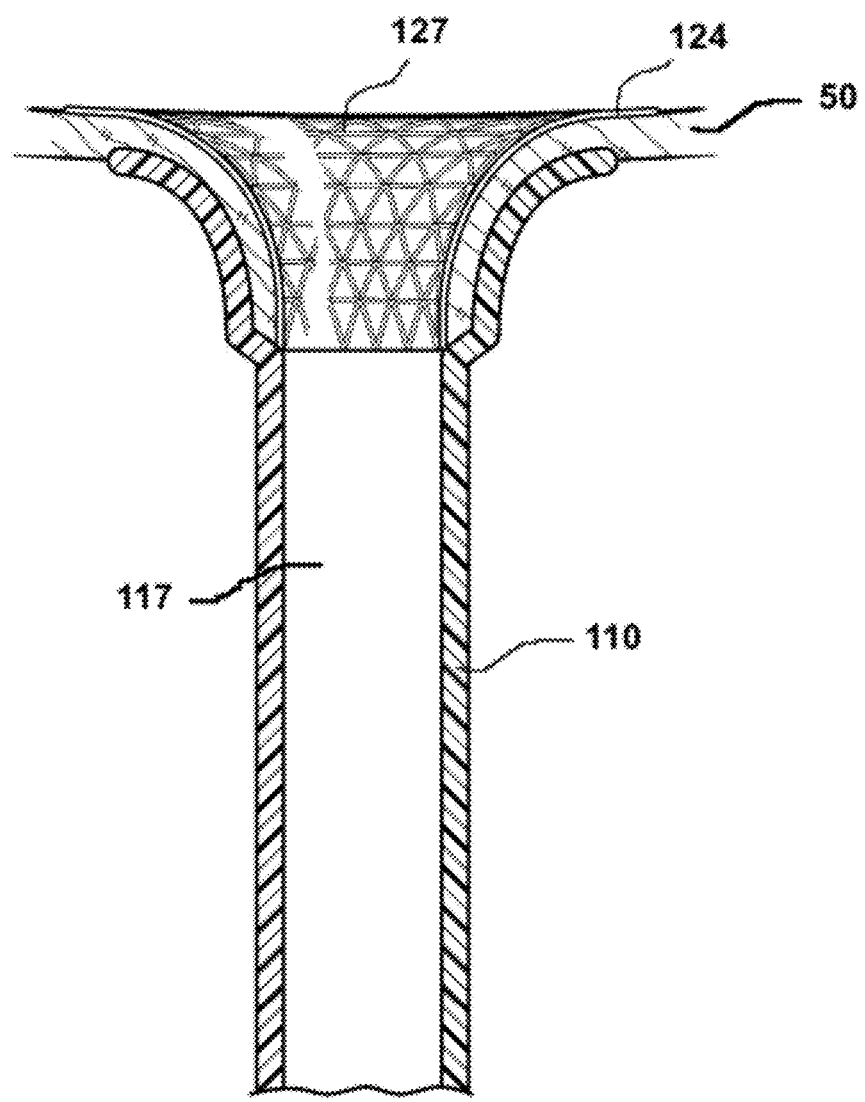

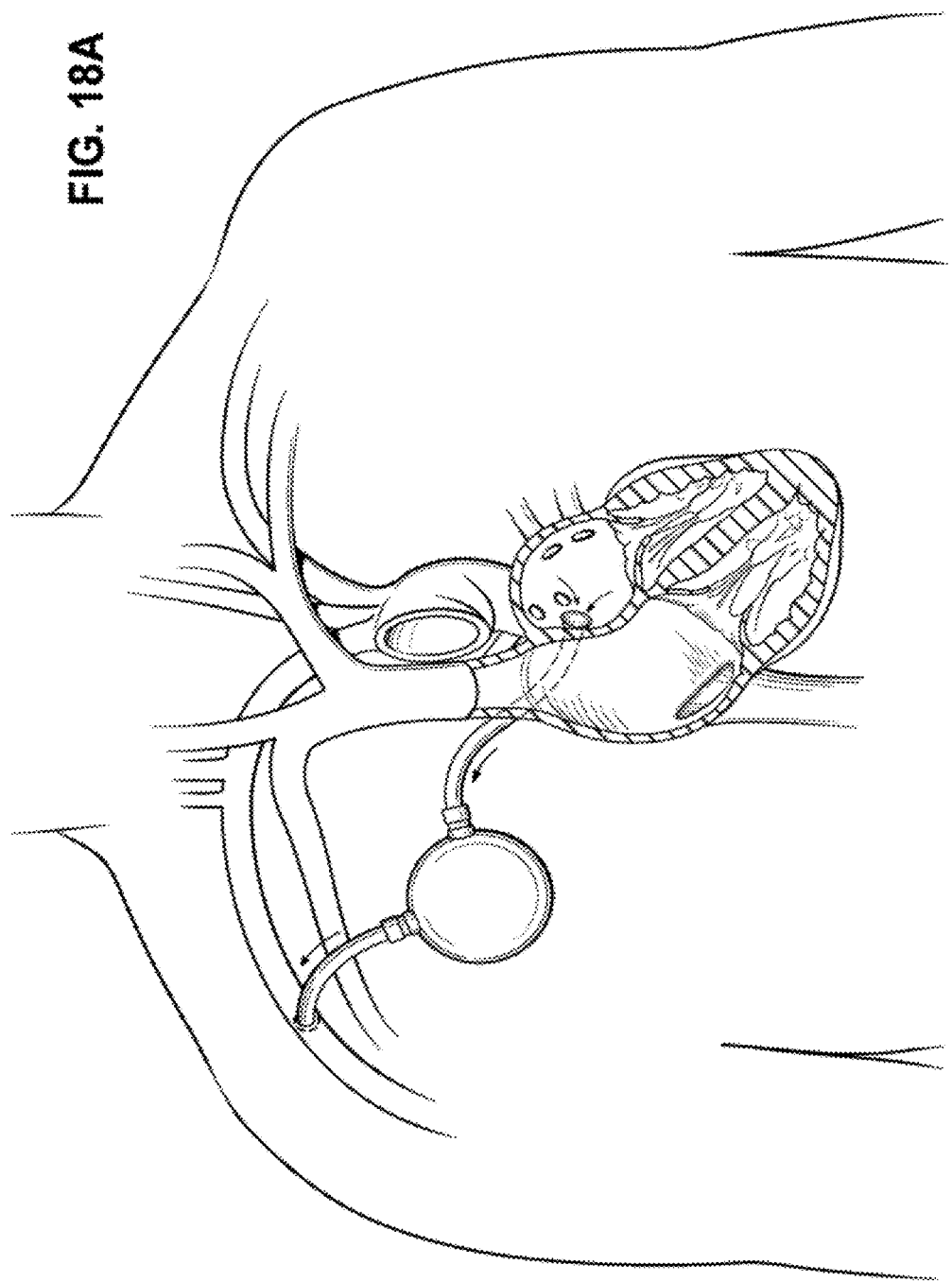

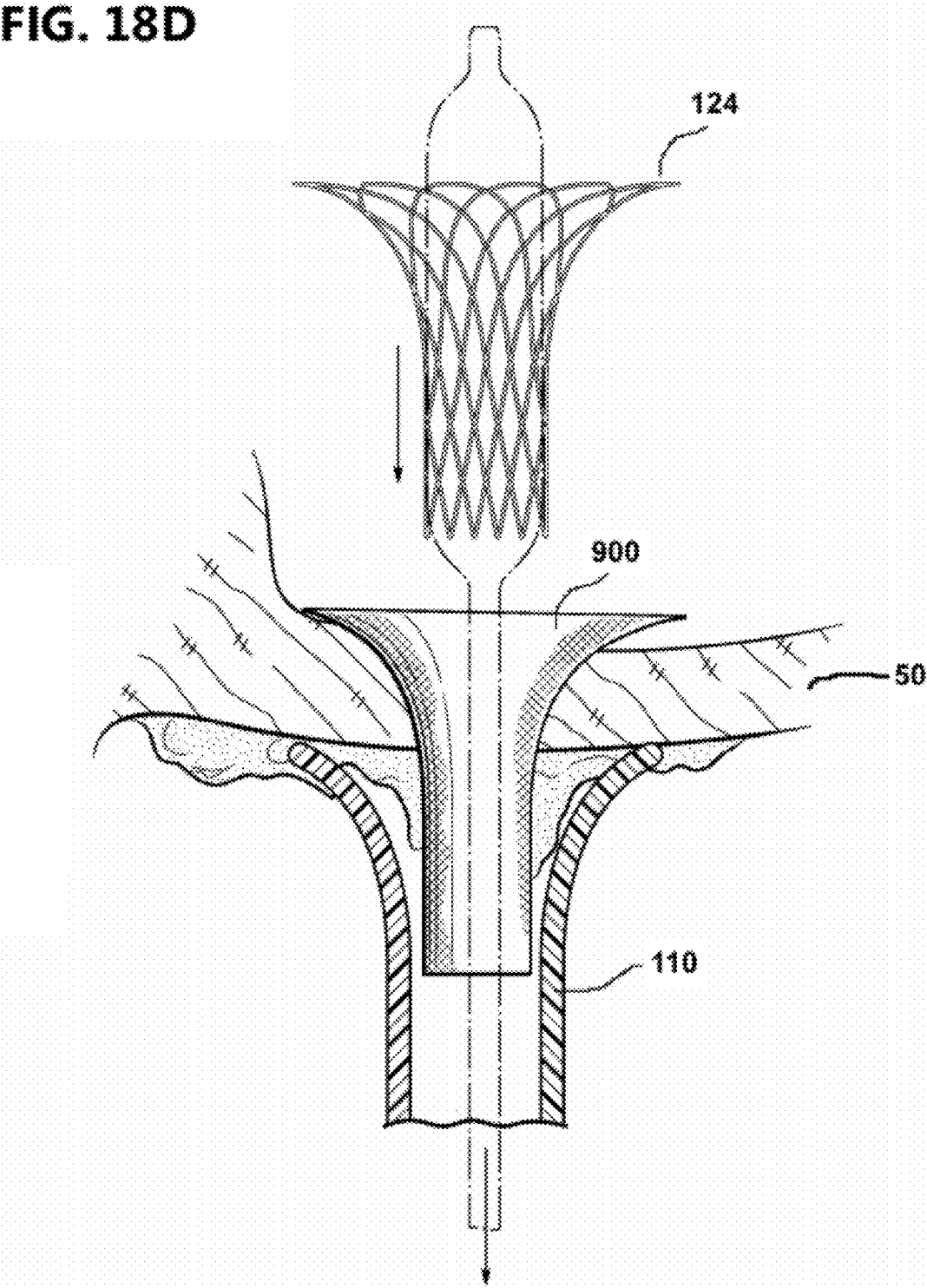

CANNULA SYSTEMS AND METHODS

CROSS-REFERENCE TO RELATED APPLICATIONS

This application claims the benefit of U.S. Provisional Application No. 61/459,055, filed Dec. 6, 2010, and U.S. Provisional Application No. 61/402,892, filed Sep. 7, 2010, the entire contents of which applications are hereby incorporated by reference.

FIELD OF INVENTION

Described herein is a cannula system to direct the flow of material from the chamber of an organ, e.g., the left atrium of a heart, and methods of placing the cannula system in fluidic communication with the organ chamber.

BACKGROUND OF THE INVENTION

Congestive heart failure occurs when cardiac function is impaired to the point that there is insufficient blood flow to support a person's activities. It is the largest problem in cardiac care today and there are more than 5 million patients with this diagnosis in the U.S. In general, patients can be treated with medications, but when symptoms are advanced, cardiac transplantation or the implantation of blood pumps may be necessary. Unfortunately, cardiac transplantation is limited by the donor pool and each year fewer than 2,000 patients undergo this procedure.

It has also been determined that the inflow cannula for a blood pump may result in clinical compositions. Clots may form around the inflow cannula as it sits in the chamber of the left atrium (or left ventricle). These clots may break off and enter the pump and then pass anywhere in the circulation. Embolization of material can cause damage to any part of the body but embolization to the brain is the most feared complication. Entry of clot into the brain generally causes brain dysfunction and the results can be mild—such as a temporary and slight slurring of speech or gait impairment to a terrible catastrophic loss of function that leaves a patient in a wheelchair or bedridden and unable to communicate. In this situation death may be a potential outcome.

Another deficiency that is encountered with cannulation of the left atrium is collapse of the left atrium and occlusion (temporary or permanent) of the inflow cannula by atrial tissue. This is similar to what happens with a vacuum cleaner tube that is brought close to material such as a curtain—the tube becomes obstructed and eventually occluded by the fabric as it is progressively sucked inside the tube. The left atrium is a very pliable thin walled structure (usually 1 mm to 3 mm in thickness). An atrial cannula is fastened to the atrial septum with 5 mm to 10 mm or more of cannula tip projecting into the left atrium. A cannula tip sitting in the left atrium and flowing at 2 to 3 liters per minute can easily suction a part of the atrial wall into the cannula leading to cannula obstruction and loss of pump flow. As flow stops in the cannula, clots may form in the cannula and when the obstruction is relieved a clot may be ejected into the circulation. Alternatively, the cannula may completely clot off and make it impossible to pump blood when the obstruction is relieved. The atrial tissue may also be injured. The first patients treated with superficial supplemental blood pumping had relatively low levels of flow, but new generations of pumps can flow at much higher rates and it would be useful to have a way to avoid the problem of a cannula suctioning atrial tissue that results in cannula obstruction and clotting and still allow the pump to flow at rates of 5 liters per minute or more.

Another problem with a cannula implanted in the left atrium is that it must be fastened securely in position. When a cannula is directed into the left atrium from the chest, it is necessary to seal the cannula to prevent bleeding and dislodgement. Typically this requires the placement of a suture circumferentially around the cannula to hold it in position e.g., a purse string suture. Also, there is frequently tissue such as fat around the entry site, and this must be dissected to ensure that no fat is forced into the heart when the cannula is pushed into the heart. If fat is pushed into the heart, it can embolize anywhere in the circulation. This means the surgeon must make a chest incision big enough to pass sutures and gain good exposure of this region. A better attachment to the heart would allow the surgeon to reduce the size of his incision and even work through endoscopic ports. Alternatively, the cannula may be passed into the left atrium from the right atrium, the hole through the septum must be sealed and the cannula must be held in place. Sealing and holding the cannula in place is not simple. An improved method of holding a cannula in place that eliminates the need for suturing and provides a secure and fluid tight seal would be valuable to patients and surgeons in preventing complications from superficial blood pumping.

Furthermore, creating a defect in the wall of the atrium to introduce a cannula is also a difficult problem. Simply pushing a cannula through a small hole is dangerous since the atrial tissue may tear. This may leave a large hole which is difficult to close.

Introducing a cannula inside the heart is usually done by placing the cannula inside catheters for delivery. This increases the diameter of the delivery system. It also creates further problems because a cannula may "snag" inside the delivery catheter. To guarantee delivery, there are serious development and manufacturing problems in maintaining the correct gap tolerances between the cannula and the catheter. Lubricants may be necessary. And even with excellent design, the operator may be forced to insert a cannula along a circuitous course. Bends may make it impossible for even the best engineered system to permit delivery of the cannula. It would be useful to eliminate the need for a catheter In summary, superficial blood pumping is a promising therapy for many patients with heart failure and it is now technically possible to pump the entire blood flow from a surface location with a very small pump. Improvements in methods and devices for cannulating the heart will make this procedure easier and safer.

SUMMARY OF INVENTION

This disclosure describes new devices, methods and systems for directing the flow of material from a chamber of an organ, e.g., the left atrium of a heart via a wall of the organ. In one embodiment, the flow of material is directed without the need to place a cannula into the chamber, e.g., the cannula system comprises a retention member that provides a smooth inflow for blood (eliminating clots) into an elongate tubular member, avoids suction against the atrial wall, and is held in place with a retaining means that provides solid fixation to prevent blood leaks and cannula dislodgement and eliminates the need for suturing.

Accordingly, in one embodiment, provided herein is a cannula system comprising a retention member, an elongate tubular member, and a means for retaining the cannula system in fluid communication with the organ chamber.

In one embodiment, the retention member is hollow and has a lumen or tubular cavity extending between its distal and proximal ends, wherein the distal end of the retention member may be expanded from a first configuration to a second configuration. When expanded to the second configuration, the perimeter of the outer surface of the distal end of the retention member is larger than the perimeter of the outer surface of the proximal end of the retention member. In one embodiment, the elongate tubular member has a distal end with a distal opening, a proximal end with a proximal opening, and a lumen extending therebetween, wherein the distal end of the elongate tubular member is configured to cooperate with one or both of the retention member and the organ wall to trap the outer surface of the distal end of the retention member to the chamber side of the organ wall, with the lumens of the retention member and the elongate tubular member in fluidic communication.

In one embodiment, the retention member and the elongate tubular member are separable, and the perimeter of the outer surface of the proximal end of the retention member is smaller than the perimeter of the distal opening of the elongate tubular member such that the proximal end of the retention member may be disposed concentrically within the distal opening of the elongate tubular member to provide the fluid communication between the two lumens. In one embodiment the lumen of the elongate tubular member is flared, e.g., has a funnel or trumpet shape at its distal end. In one embodiment, where the expanded second configuration of the retention member conforms to the flared shape of the distal end of the elongate tubular member; material may flow from the chamber through the retention member into the elongate tubular member. In one embodiment, where the inner surface of the flared distal opening of the elongate tubular member is anchored to the organ wall outside the chamber, and the retention member may optionally be absent; material flows from the chamber directly into the elongate tubular member outside the organ.

In another embodiment, the retention member and the elongate tubular member are integrally connected and manufactured as single component, e.g., an inflow tube, of the system. In this embodiment, the proximal end of the retention member is integral with the distal end of the elongate tubular member to form the cannula. However, the distal end of the inflow tube may expand from a first configuration to a second configuration in which the perimeter of the outer surface of the distal end is larger than the perimeter of the outer surface of the proximal end of the inflow tube. Accordingly, the distal end of the cannula may still have a flared or trumpet shape, the outer surface of which may be anchored to the chamber side of an organ wall when the cannula system is in fluid communication with the organ.

The hollow retention member or distal end of an inflow tube may be self expanding or may require additional manipulation for expansion, e.g., inflation with a balloon. When self expanding, the hollow retention or distal end of an inflow tube member may be compressed or retained in the first compressed configuration by a compression member, which may be a sheath, a compression tip, a suture, a forceps and a combination thereof. In one embodiment, the means for compressing is a sheath. In another embodiment, the compression element is part of a dilator. In the first compressed configuration the distal end of the hollow retention member or inflow tube may have an outer surface perimeter that is generally consistent with, or in some embodiments smaller than, the outer surface perimeter of the elongate tubular member or the proximal end of the inflow tube, respectively.

In one embodiment, the distal end of the retention member or inflow tube comprises a textured surface at the interface of the distal end and the chamber side of the organ wall. In one embodiment, the textured surface is provided by a fabric that promotes tissue ingrowth, e.g., teflon, dacron, etc. In another embodiment, a circumferential step is formed at the junction between the textured surface and/or fabric and the retention member.

A cannula system as disclosed herein further comprises a means for retaining the system in fluidic communication with the organ, such as a retaining element. In one embodiment, the retaining element is selected from the group consisting of a plurality of barbs, at least one annular ring, and elongate struts within the hollow retention member. Other retaining means include stents or springs that are configured to cause circumferential contact between the outer surface of the retention member and the chamber side of the wall.

In one embodiment, a cannula system as disclosed herein is made of any biocompatible material. In another embodiment, the cannula system is made of a polymer such as silicone or polyurethane. In one embodiment, at least the elongate tubular member of a cannula system disclosed herein comprises cables embedded in the walls, stiffeners, or other means to adjust the position of the cannula system.

The major advantages of this cannula system are clear regardless of whether the hollow retention member and elongate tubular member are separable or manufactured as integrally connected. For example, the flared distal end of the cannula system reduces the formation of stagnant areas and eddy currents. Further, the flared, funnel, or trumpet shape of the cannula system herein provides for the flow of material out of the organ in a smooth gentle curve that will produce little turbulence. Accordingly, a cannula system disclosed herein may be useful to direct the flow of material from any organ chamber, e.g., food from the stomach, blood from the heart, etc. In one embodiment, the cannula system is used to direct blood from the left atrium of the heart.

In one embodiment, the cannula system is placed in fluidic communication with an organ chamber by advancing the cannula system as described herein to the chamber, disposing the retention member in the first configuration through an opening in a wall of the organ into the chamber so that the retention member is disposed inside the chamber of the organ and the lumen of the proximal end of the retention member is in fluid communication with the lumen of the elongate tubular member outside the chamber, expanding the retention member to a second configuration, and trapping the retention member to a portion of the chamber side of the organ wall surrounding the opening with at least a portion of the trapped wall conforming to the shape of the retention member in its second configuration.

In one embodiment, the retention member, or distal end of the cannula comprising an integrally connected retention member and elongate tubular member, is disposed through the opening with a catheter assembly. In one embodiment, the retention member or distal end of the cannula is disposed through the opening without a catheter.

In one embodiment, wherein the hollow retention member and the elongate tubular member are separable, and wherein the elongate tubular member includes a flared distal opening, the method comprises anchoring the inner surface of the flared distal opening of the elongate tubular member to the organ wall outside the chamber and removing the retention member from the inside chamber of the organ through the hole in the wall and the elongate tubular member.

BRIEF DESCRIPTION OF THE DRAWINGS

FIGS. 2A-2B are diagrammatic views of an illustrative circulatory assist system positioned in the human heart shown in cross-section.

FIG. 2C is a schematic representation of an exemplary cannula system for directing the flow of blood from the left atrium chamber of a heart in a patient through the right atrium chamber of the heart.

FIGS. 4A-4E are longitudinal cross-sectional views of another exemplary cannula system and an exemplary method of placing the cannula system into fluidic communication with a chamber of an organ using a catheter delivery system and a balloon.

FIG. 4F is a longitudinal cross-sectional view of the cannula system of FIGS. 4A-4E in fluidic communication with a chamber of an organ.

FIGS. 9A-9C are longitudinal cross-sectional views of another exemplary cannula system and an exemplary method of placing the cannula system into fluidic communication with a chamber of an organ using a catheter delivery system.

FIG. 9D is a longitudinal cross-sectional view of another exemplary cannula system in fluidic communication with a chamber of an organ.

FIGS. 12A-12C are longitudinal cross-sectional views of another exemplary cannula system and an exemplary method of placing the cannula system into fluidic communication with a chamber of an organ without use of a catheter.

FIG. 17 is a cross-sectional view of another exemplary cannula system in fluidic communication with a chamber of an organ.

FIG. 18A is a diagrammatic view of an illustrative circulatory assist system positioned in the human heart shown in cross-section.

FIGS. 18B-18F are longitudinal cross-sectional views of another exemplary cannula system and an exemplary method of placing the cannula system in fluidic communication with a chamber of an organ.

DETAILED DESCRIPTION

Figure 1A:
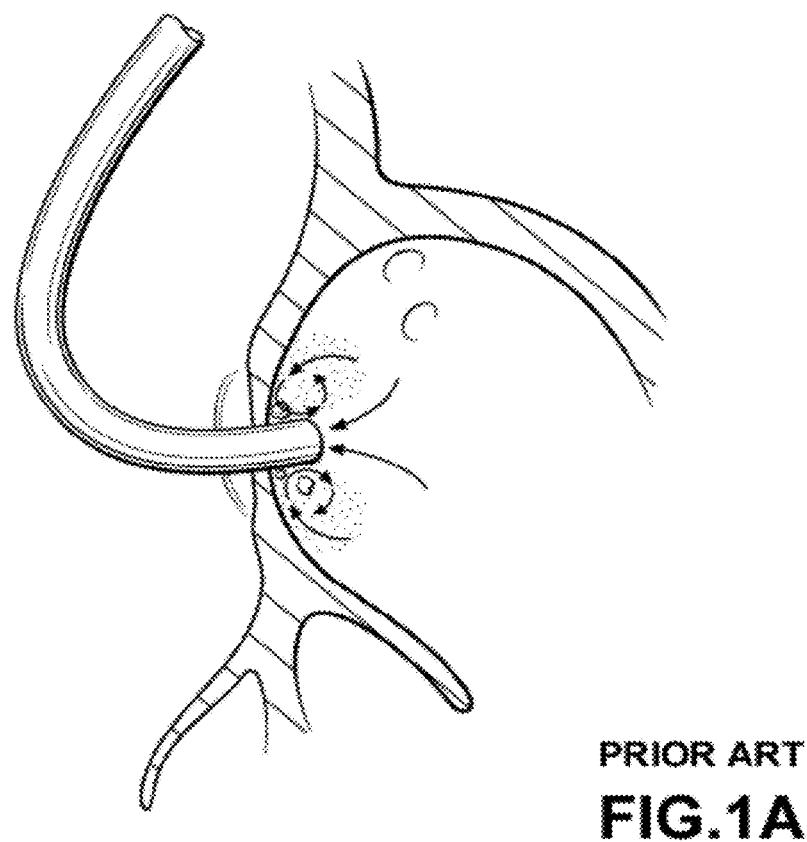
FIGS. 1A-1C are diagrammatic views of a prior art cannula accessing the left atrium of the heart by the atrial septum.

FIG. 1A illustrates an inflow cannula for a heart pump positioned in the left atrium of the heart according to a known approach, with the tip of the inflow cannula extending about one centimeter into the left atrium from the atrial septum. While blood flow into the inflow cannula is brisk, the blood around the inflow cannula is stagnant and can form eddy currents that limit the entry of fresh blood to wash the area surrounding the inflow cannula. Clots may form in this region.

Figure 1B:
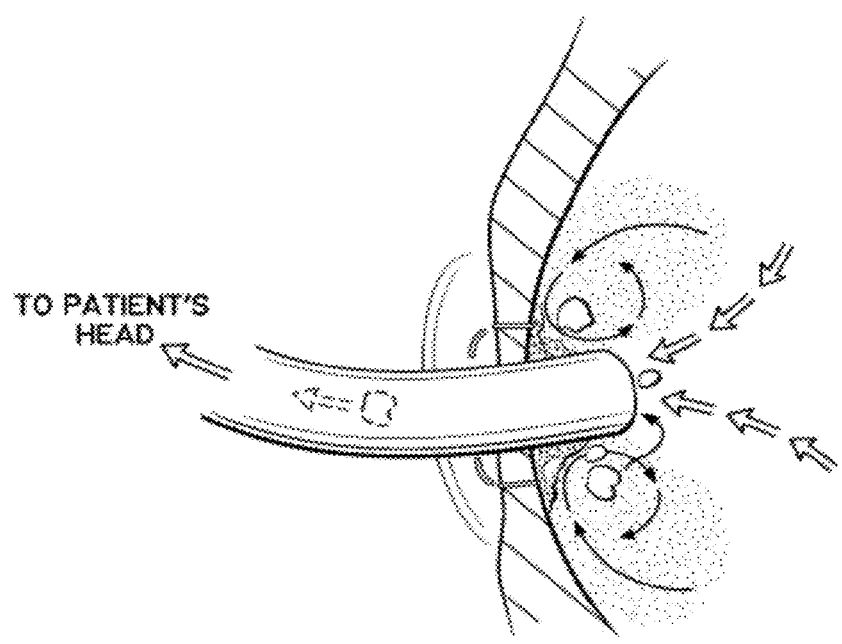

FIG. 1B shows that a clot has formed and attached to the atrial wall around the inflow cannula. Other clots may form along the side of the inflow cannula, and may not attach securely to the inflow cannula and thus may become dislodged. Clots may be drawn into the inflow cannula by the strong flow induced by the blood pump.

Figure 1C:
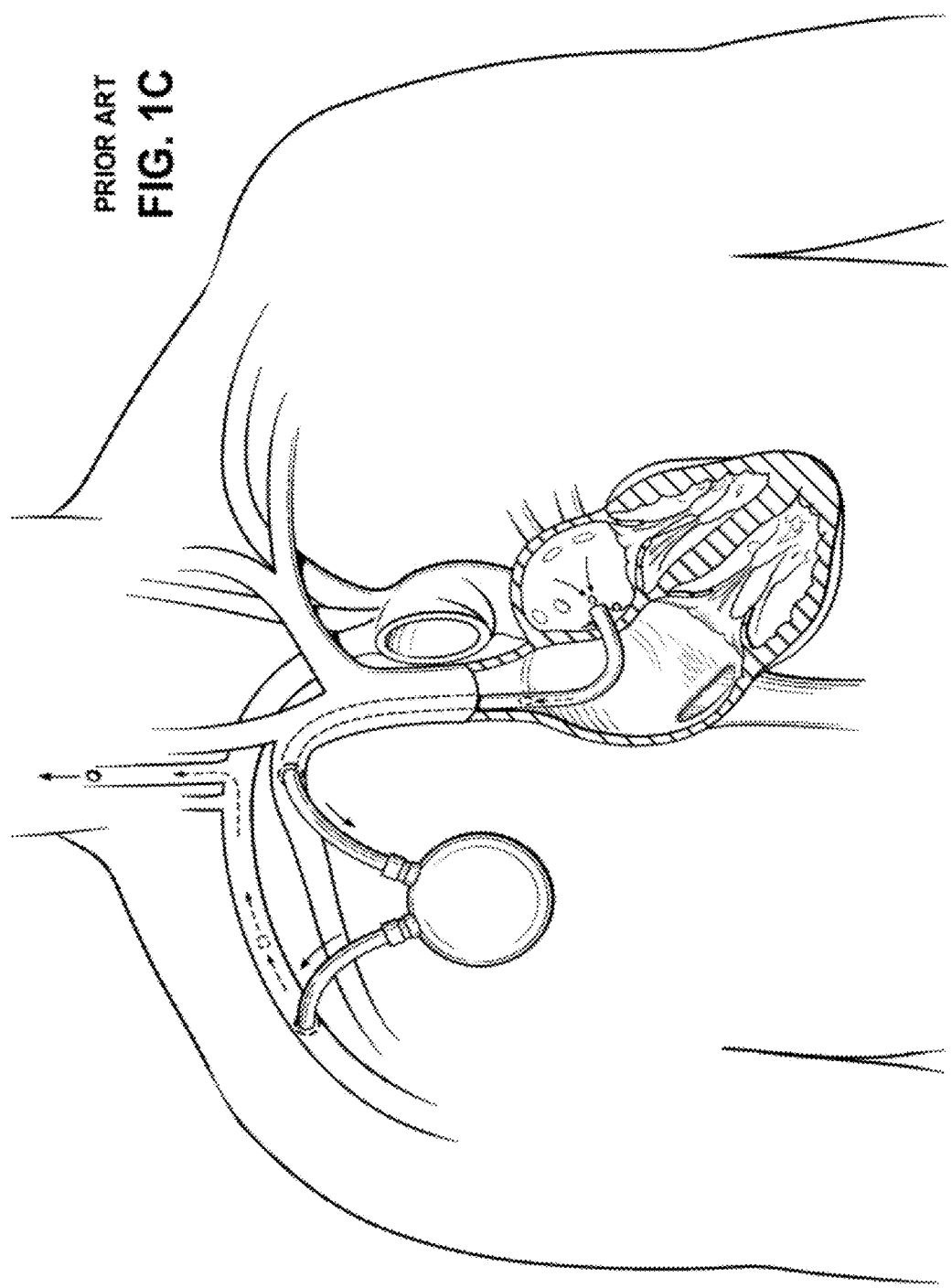

FIG. 1C indicates a catastrophic outcome for a clot originating around the inflow cannula inside the left atrium. A clot has formed around the inflow cannula tip, entered the inflow cannula and has been suctioned through the pump, into the subclavian artery and is shown passing into the patient's right carotid artery. A clot of this size may be lethal—or cause permanent and severe brain dysfunction.

This disclosure describes new devices, methods and systems for directing the flow of material from a chamber of an organ, and in particular, for directing blood from the left atrium of the heart. For example, the devices, methods and systems described herein may be incorporated into a circulatory assist system to improve the flow of material from the left atrium of the heart and reduce the risk of embolism.

Shown in FIGS. 2A and 2B are diagrammatic views of an illustrative circulatory assist system positioned in the human heart for superficial blood pumping. Here an cannula system is shown directed from the axillary or subclavian vein into the right atrium and across the interatrial septum with its retention member sitting inside the left atrium. The cannula system draws blood into a pump, which expels the blood via a second, outflow cannula into the subclavian artery. The cannula system can be introduced from any available large vein in the head or neck area including the axillary and subclavian veins in the shoulder and the jugular vein in the neck. The outflow cannula can be connected with a superficial operation to the subclavian, axillary and carotid arteries.

The cannula system shown in FIG. 2A enters the venous system in the subclavian or axillary vein. It is also possible to enter the venous system via the jugular vein as shown in FIG. 2B. The cannula system may be passed over the clavicle to the pump implanted in a pocket formed in the patient's chest (which is in a typical location for a pacemaker). A tube running over the clavicle may feel uncomfortable for a patient or the tube may become compressed against the clavicle especially when a patient lies on his side (particularly risky when the patient is asleep and unaware). This can reduce blood inflow into the pump. A useful alternative would be to pass the cannula system under the clavicle to the pacemaker pocket as shown in FIG. 2B. The portion of the cannula system that passes under the clavicle is shown in dotted lines.

Using this configuration, the cannula system may be introduced into the jugular vein without cutting down on the vein. There are many standard commercially available kits that allow jugular access. Typically, the procedure starts by cannulating the jugular vein in the neck with a needle. A wire is then introduced into the vein through the needle. The skin entry site is then enlarged with a knife blade or other sharp instrument. A series of dilators are then passed over the wire to stretch a tract from the skin to the vein. The cannula system can then be passed down this track either directly or inside a catheter. The distal end of the cannula system can then be placed across the interatrial septum to provide inflow of blood from the left atrium to the pump. The proximal end of the cannula can be passed from the skin entry site, under the clavicle, and to the pacemaker pocket such that the entire cannula system is positioned below the skin after implantation. To facilitate passing the cannula system from the jugular entry site to the pacemaker pocket, one or more small incisions may be made above and/or below the clavicle. For example, the cannula system may first be passed from the initial skin entry site to the region just above the clavicle and subsequently be passed under the clavicle in a carefully controlled fashion to avoid injury to arteries, veins and nerves which pass under the clavicle.

The pump can be of any type or shape and it is shown disposed inside a superficial pocket outside the chest cavity in the area typically used to implant a pacemaker. It can be implanted under the skin or under the muscle on the chest wall.

The pump requires a control and power input (not shown). This is typically done with an electrical cable that travels from the pump to the outside of the patient. The electrical drive line or cable is attached to a controller and power source. Many varieties of cables, power supplies and controllers have been described.

Pumps can also be powered by a fully implantable system (not shown) that does not require a drive line through the skin. In this situation the controller unit is implanted in the patient and a transcutaneous energy transmission receiving system is implanted to receive power and it is stored in implanted batteries. Typically the system is recharged by placing an external unit on the skin overlying the implant to allow recharging.

An exemplary cannula system 100 disclosed herein is shown schematically in FIG. 2C in the right atrium of a patient's heart, engaging the atrial septum at an opening in the septum. Cannula system 100 is configured to allow passage of blood from the left atrium via the opening in the atrial septum and to an intake port of a blood pump (not shown in FIG. 2C). Cannula system 100 includes an elongate tubular member 110 and a coupling assembly 120 disposed at the distal end of elongate tubular member 110. Elongate tubular member 110 includes a lumen extending from a distal opening at the distal end to a proximal opening at the proximal end. Coupling assembly 120 includes a retaining element 122 and a retention member 124. Retaining element 122 and retention member 124 are configured to cooperate with each other and with the portion of the atrial septum surrounding the opening in the septum to couple or anchor cannula system 100 to the septum and to provide fluidic communication between the distal opening of the elongate tubular member 100 and the chamber of the left atrium.

The anchoring function of coupling assembly 120 can be performed by trapping, clamping, or otherwise retaining the portion of the atrial septum between retaining element 122 and retention member 124. The retaining element 122 and retention member 124 can each include a lumen therethrough, which lumens can be in fluidic communication, e.g. by one of the retaining element 122 and retention member 124 being disposed concentrically within the other, and thus can collectively provide for fluidic communication between the distal end of coupling assembly 120 and the distal opening of flow tube 110. This concentric relationship is consistent with the anchoring function, i.e., by having the portion of the atrial septum disposed within the annulus between the concentrically arranged retaining element 122 and retention member 124.

At least the one of the retaining element 122 and/or retention member 124 that is disposed on the left atrium side of the atrial septum (and the lumen of which is therefore in the flow path from the left atrium to the lumen of flow tube 110) is preferably formed with a flared or tapered shape, i.e. having a distal end that has a larger perimeter than the perimeter of the proximal end.

In alternative embodiments of a cannula system disclosed herein, the retention member 124 and the elongate tubular member 110 may be separable or manufactured integrally connected to make a cannula or inflow tube 10 of the system. An ordinarily skilled artisan will understand that such a cannula or inflow tube will generally have a proximal end, a tubular body (e.g., an elongate tubular member 110), a distal end (e.g., a hollow retention member), an outer surface, and a lumen extending between a proximal opening at the proximal end and a distal opening at the distal end, wherein the distal end is self-expandable to a flared, funnel, or trumpet shape.

The broad inflow orifice, e.g., the distal flared end of a cannula system described herein increases the cross-sectional area for blood to enter the system and thus reduces blood velocity and pressure drop or suction. Accordingly, this cannula system is much less likely to suction atrial tissue that may result in cannula obstruction or tissue damage by suction despite the fact that part of the cannula system remains within the chamber. However, the flared distal end of the cannula system, e.g., hollow retention member 124, does not extend into the atrium and thus avoids having a tip inside the atrium that may suction tissue. Furthermore, after a cannula system described herein is anchored into the atrium, it can be pulled backward, or proximally, so that there is no protrusion into the left atrium. This may be further facilitated by anchoring the cannula system inside the chest to pull the atrial wall or septum outward. The major advantages of this system are clear. For example, there is no cannula tip in the left atrium to allow the formation of stagnant areas and eddy currents. Clots are less likely to form on the cannula tip, so, the risk of embolism and stroke is reduced. Also, the path for blood is very smooth. Blood passes along natural atrial tissue into the cannula in a smooth gentle curve that will produce little turbulence and reduce the risk of clotting.

The distal end of the cannula system will not be inclined to suction against the atrial wall and occlude the cannula, because there is no tip extending into the left atrium to suction tissue. Further, the enlarged inflow orifice reduces the velocity of blood as it enters the cannula system, reducing the likely hood of suction.

A lattice-like stent structure disposed on tissue quickly develops a covering of native tissue. So using a stent to anchor the distal end of the cannula system to the atrial septum will also lead to a covering of natural tissue (which is resistant to clotting) covering in the first part of the pump system.

Accordingly, a cannula system disclosed herein may be attached to the inside of the left atrium and the retention member held in place provides a smooth inflow for blood through the flared distal end (eliminating clots), avoids suction against the atrial wall, provides solid fixation by a retaining means, e.g., a retaining element, to prevent blood leaks and cannula dislodgement. Notably, the retaining element 122 also allows this system to be sutureless. Accordingly, the surgeon may work remotely from the point of entry into the left atrium. The retaining element also prevents movement. For tissue to heal and for attachment of the hollow retention member to the tissue, a strong and immobile connection is important.

The cannula system can generally be made from any biocompatible material. It may be useful for the interior of the hollow retention member 124 to be soft or spongy, which will allow it to "bury" itself into the wall of the elongate tubular member 110 so that any elongate struts are not exposed to the path of blood flow beyond the point where there is atrial tissue. The cannula system may be made of a polymer such as, for example, silicon or polyurethane such that the hollow retention member is flexible and can be reduced into a catheter or other delivery device. The cannula system may also be made according to well-known methods.

Additionally, the cannula system, and in particular, the distal end of the hollow retention member or inflow tube may also be expandable—it could be placed in a smaller diameter and then activated to a larger final size, e.g., with a balloon. In other embodiments, the cannula system can be restrained in a smaller diameter during the first part of implantation and allowed to regain its full size by the end of the procedure.

Several exemplary implementations of cannula system 100 are described in more detail below, and may be placed in fluid communication with an organ chamber with a catheter assembly. Catheter assemblies are well-known in the art, and may include any combination of a catheter 910, a wire 912, an obturator 914, and a dilator 916. In one embodiment, the dilator 916 is modified to comprise cutting surfaces, e.g., metal blades or blade-like features which are molded into the dilator to enable a "clean" entry into the organ chamber through a chamber wall, e.g., into the atrium through the atrial septum, rather than an irregular cut that extends beyond the margin that can be easily sealed. In some cases, it may be difficult to create a defect that is exactly the size of the outer surface of the lumen of the elongate tubular member 110 to aid in the creation of a good seal. For atrial septal puncture a number of manufacturer's make catheter assemblies which include sharp curved needles and catheters to accomplish this task. (St. Jude Medical).

The dilator may also have additional functions: it could be useful in advancing the cannula system by friction between the cannula lumen and the dilator. A balloon or even a mechanical assembly could be added to the dilator to increase or adjust the friction to move a cannula system and then minimize the friction to allow the removal of the dilator.

Although many embodiments describe placing a cannula system 100 in fluidic communication with the left atrium of a heart, an ordinarily skilled artisan will recognize that the devices, systems and methods disclosed herein may be used to direct the flow of material (including liquid or gas) from, or into, most organs having a chamber, e.g., the flow of food from the stomach, the draining of sinuses, bladders, kidneys, lungs, etc.

As described herein, a cannula system 100 comprises (a) a hollow retention member 124 having a proximal end 121, a distal end 123, an outer surface 128, and a lumen 126 extending between the proximal end 121 and the distal end 123, the distal end 123 being expandable between a first configuration and a second configuration in which the perimeter of the outside surface of the distal end is larger than the perimeter of the outside surface of the proximal end; (b) an elongate tubular member 110 having a distal end 113 with a distal opening 114, a proximal end 115 with a proximal opening 116, and a lumen 117 extending therebetween, the distal end 113 of the tubular member 110 configured to cooperate with one or both of the retention member 124 and the organ wall 50 to anchor the distal end 113 of the tubular member 110 outside the chamber with the lumen 117 of the tubular member 110 in fluid communication with the lumen 126 of the retention member 124; and at least one retaining element 122 configured to anchor one or both of (a) at least a portion of the outer surface of the retention member 124 to the chamber side of the organ wall 50 and (b) the tubular member 110 to the organ wall 50 outside the chamber.

FIGS. 3A-3D are longitudinal cross-sectional views of an exemplary cannula system 100 and an exemplary method of placing the cannula system 100 into fluidic communication with a chamber of an organ using a catheter delivery system. In this exemplary embodiment, the elongate tubular member 110 is generally positioned outside the chamber against the organ wall 50 from which material is to be removed—e.g., for removing blood from the heart, the atrial septum if an intravascular approach is used or the left atrial free wall if an approach is used inside the chest. The elongate tubular member 110 has a flare, funnel or trumpet shape at its distal end 113. The elongate tubular member 110 may be fastened or anchored to the atrial wall or the septum so that it remains on the outside of the atrium in such a way that blood can pass freely through the hollow retention member 124 without leaking.

Figure 3A:
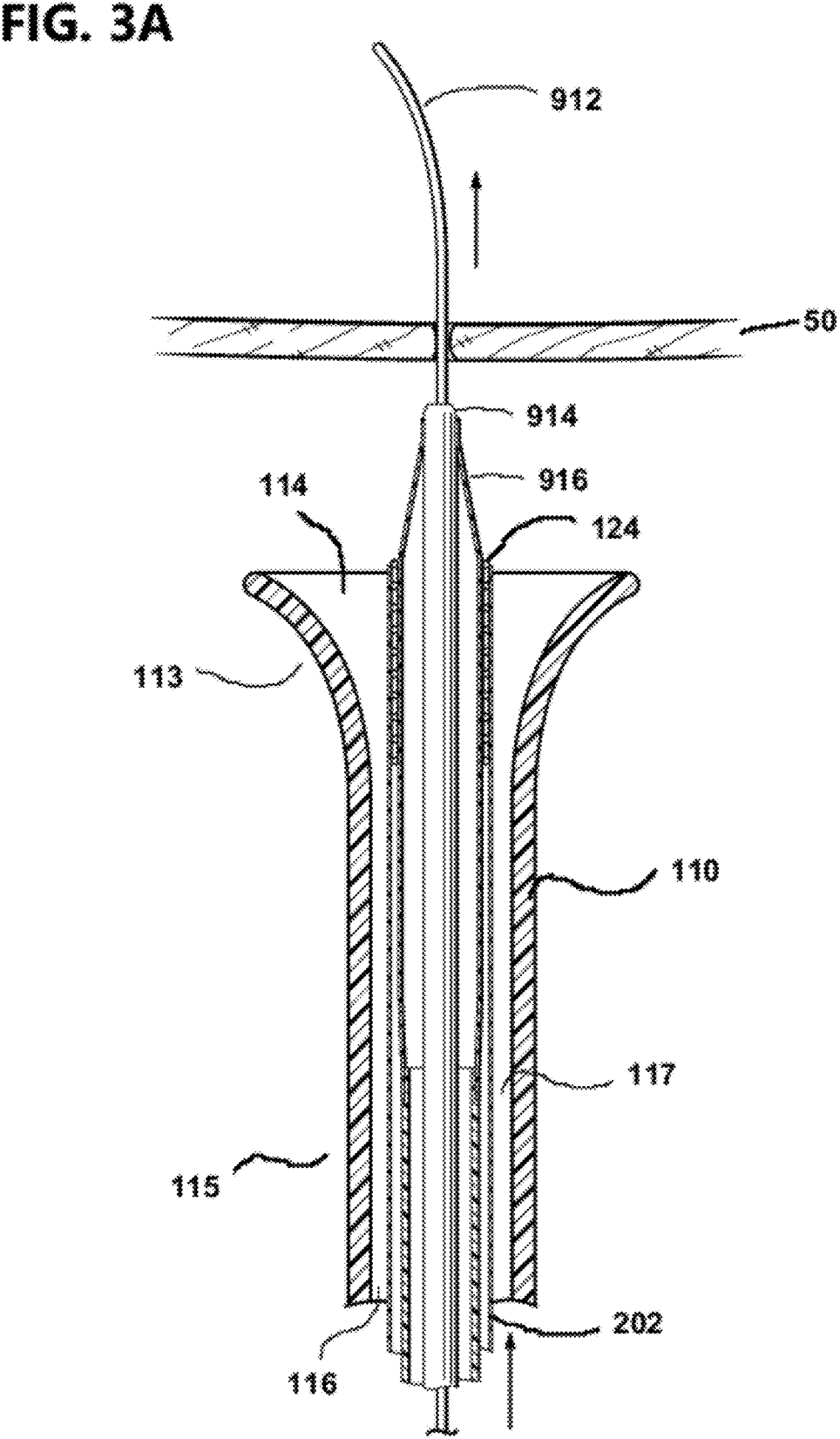
FIGS. 3A-3D are longitudinal cross-sectional views of an exemplary cannula system and an exemplary method of placing the cannula system into fluidic communication with a chamber of an organ using a catheter delivery system.

In FIG. 3A, the elongate tubular member 110 is shown with a trumpet-shaped distal end 113 on the outside of the left atrium. Inside the tubular member 110 is a catheter assembly which contains a wire 912 that is shown passing into the left atrium. The catheter assembly includes a dilator tipped obturator 914 which is used to follow over the wire 912 into the left atrium. The dilator tip allows the wall of the atrium to be gradually enlarged.

As is generally well-known, the wire can be placed through a needle placed under direct vision if the surgeon is working through the chest. Alternatively, the wire 912 may have a sharpened tip to puncture the left atrium. If the interatrial septum is to be punctured, a variety of atrial septal puncture needles are available for this purpose. The surgeon may use fluoroscopy (X-ray) or ultrasound (transthoracic, transesophageal, or even intravascular or intracardiac—ICE) during endovascular procedures to guide the needle/wire 912.

Figure 3B:
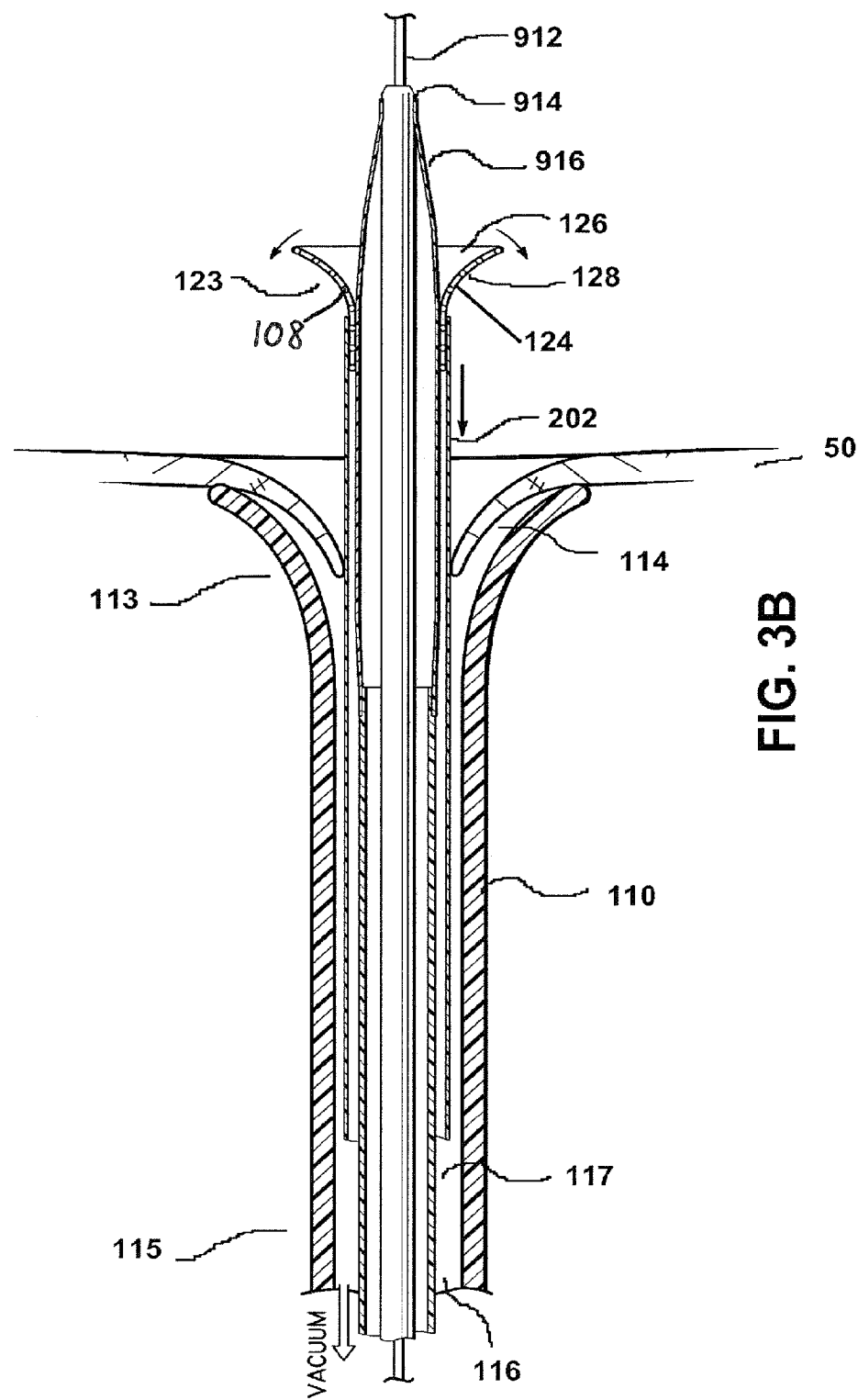

In FIG. 3B, the catheter assembly has been placed inside the left atrium. A hollow retention member 124 comprising a self expanding nitinol stent 108 is shown that is retained by a sheath 202 within the catheter assembly and is partly deployed by withdrawing the sheath 202. The retention member 124 stent 108 can automatically spring open as the sheath 202 is withdrawn. In this embodiment, the retention member 124 is created to conform to the distal opening 114 of the flared distal end 113 of the elongate tubular member 110.

The catheter assembly can then be pulled back toward the atrial wall/septum as the elongate tubular member 110 is pushed against the wall of the left atrium (or the interatrial septum).

Figure 3C:
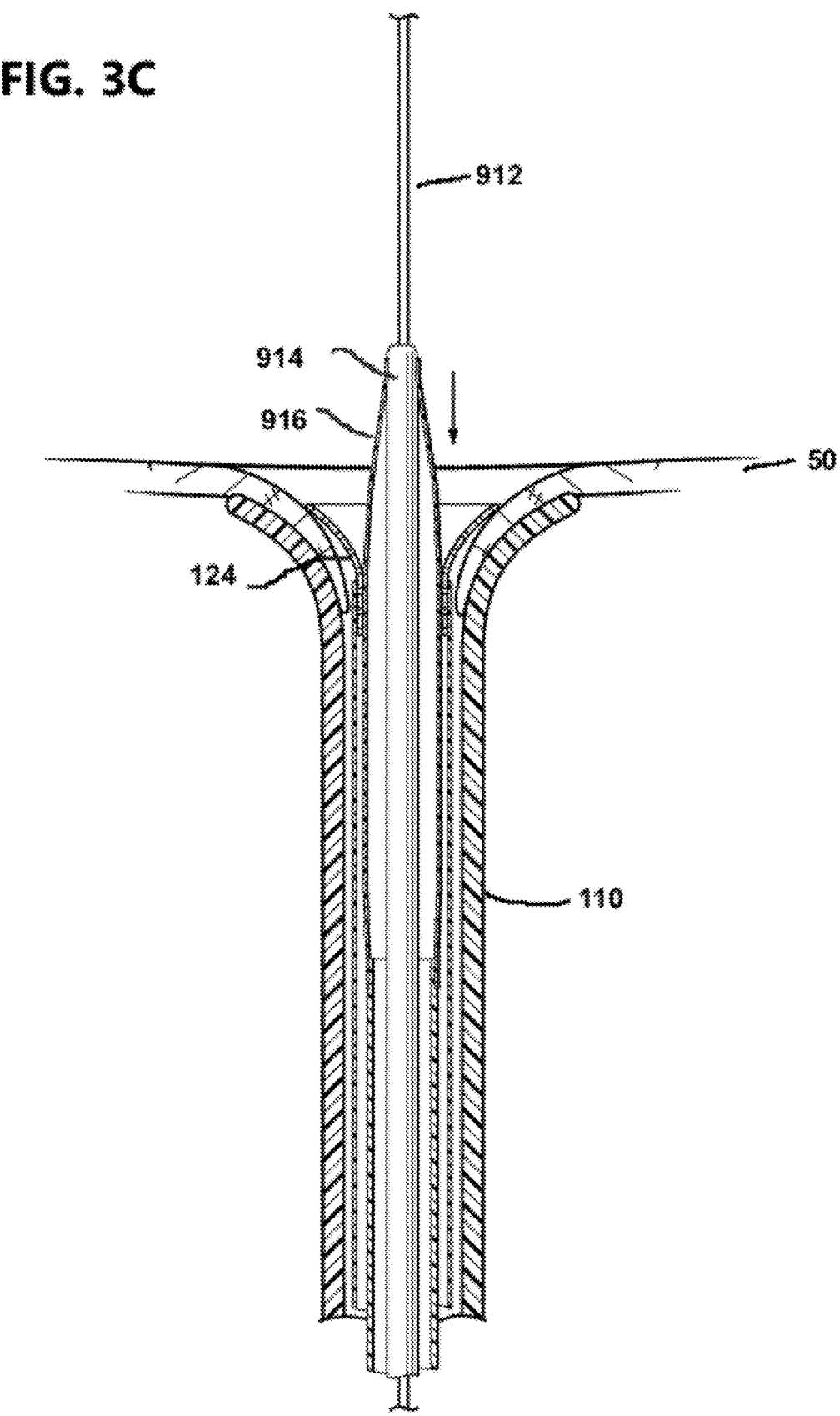
Figure 3D:
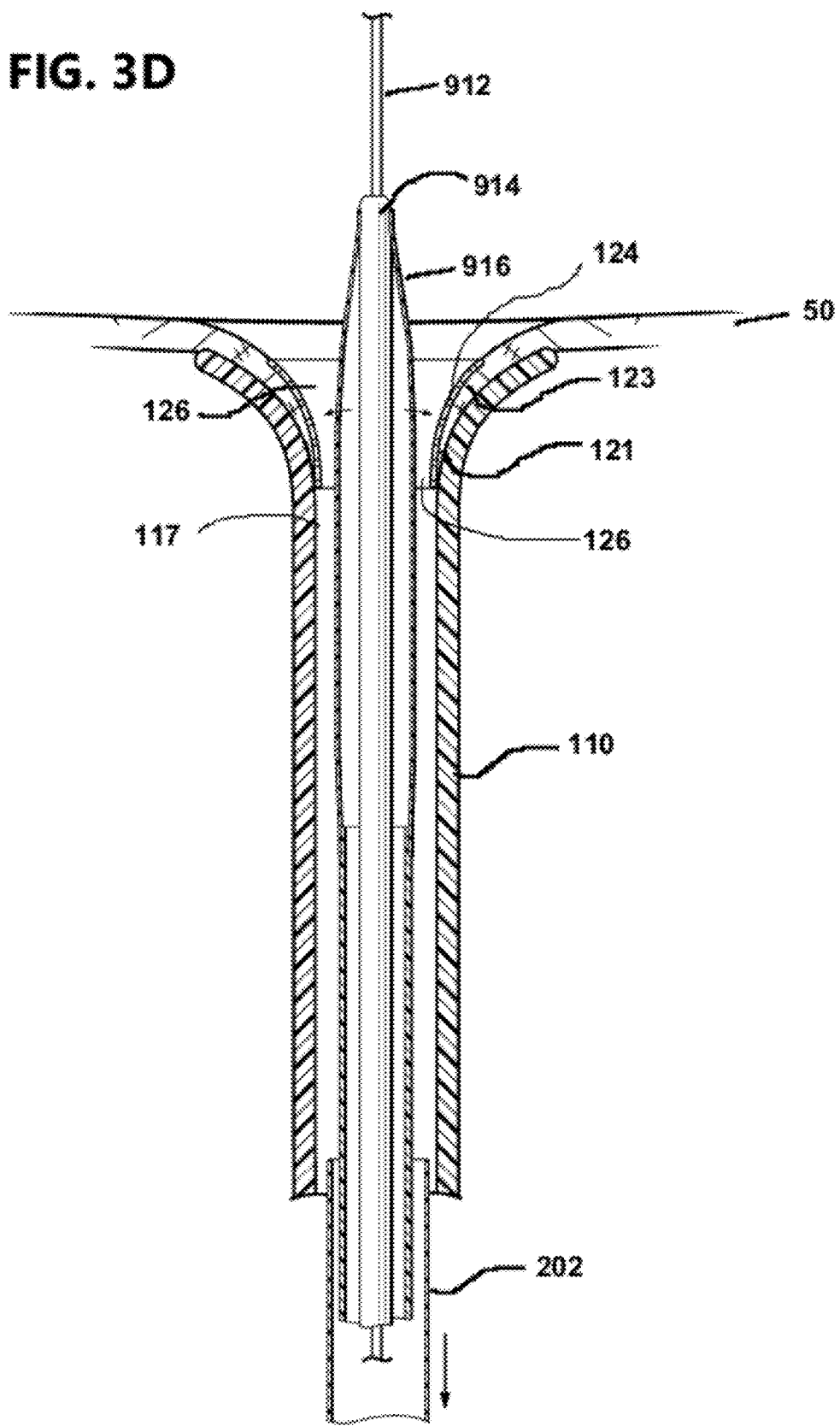
Figure 3E:
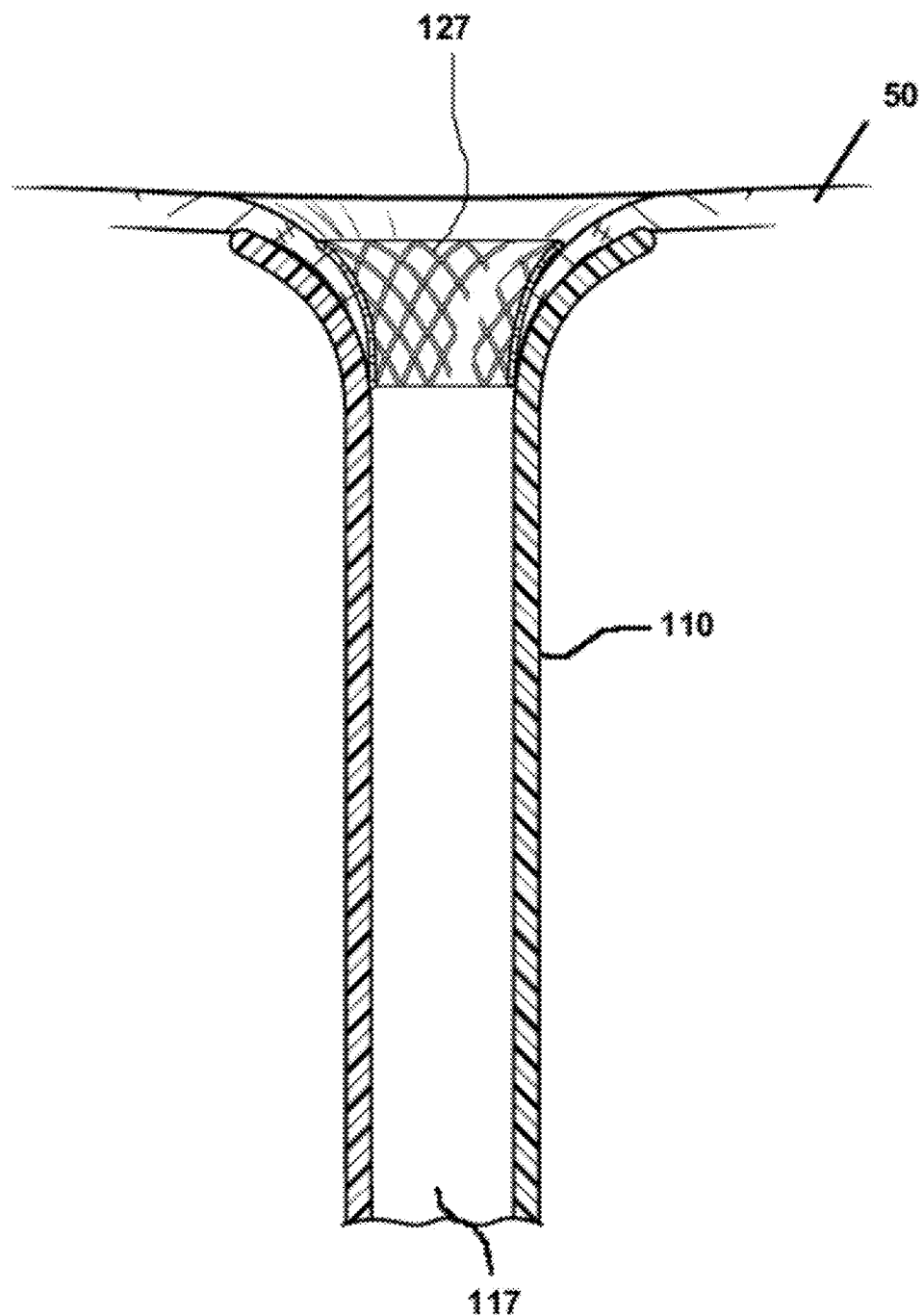
FIG. 3E is a longitudinal cross-sectional view of an exemplary cannula system in fluidic communication with a chamber of an organ.

In FIG. 3C, the retention member 124 is shown pulled back the atrial tissue to trap the atrial tissue 50 between the retention member 124 and the elongate tubular member 110, which remains outside the atrium. In FIG. 3D, the sheath 202 restraining the retention member 124 is further withdrawn, and the retention member 124 is fully expanded and released. The retention member 124 traps the atrial tissue against the tubular member 110. This provides a solid seal to hold the cannula system in place and to prevent leakage of blood. FIG. 3E shows the cannula system 100 in its final configuration and in fluidic communication with the left atrium after the catheter assembly has been withdrawn and released.

Figure 4A:
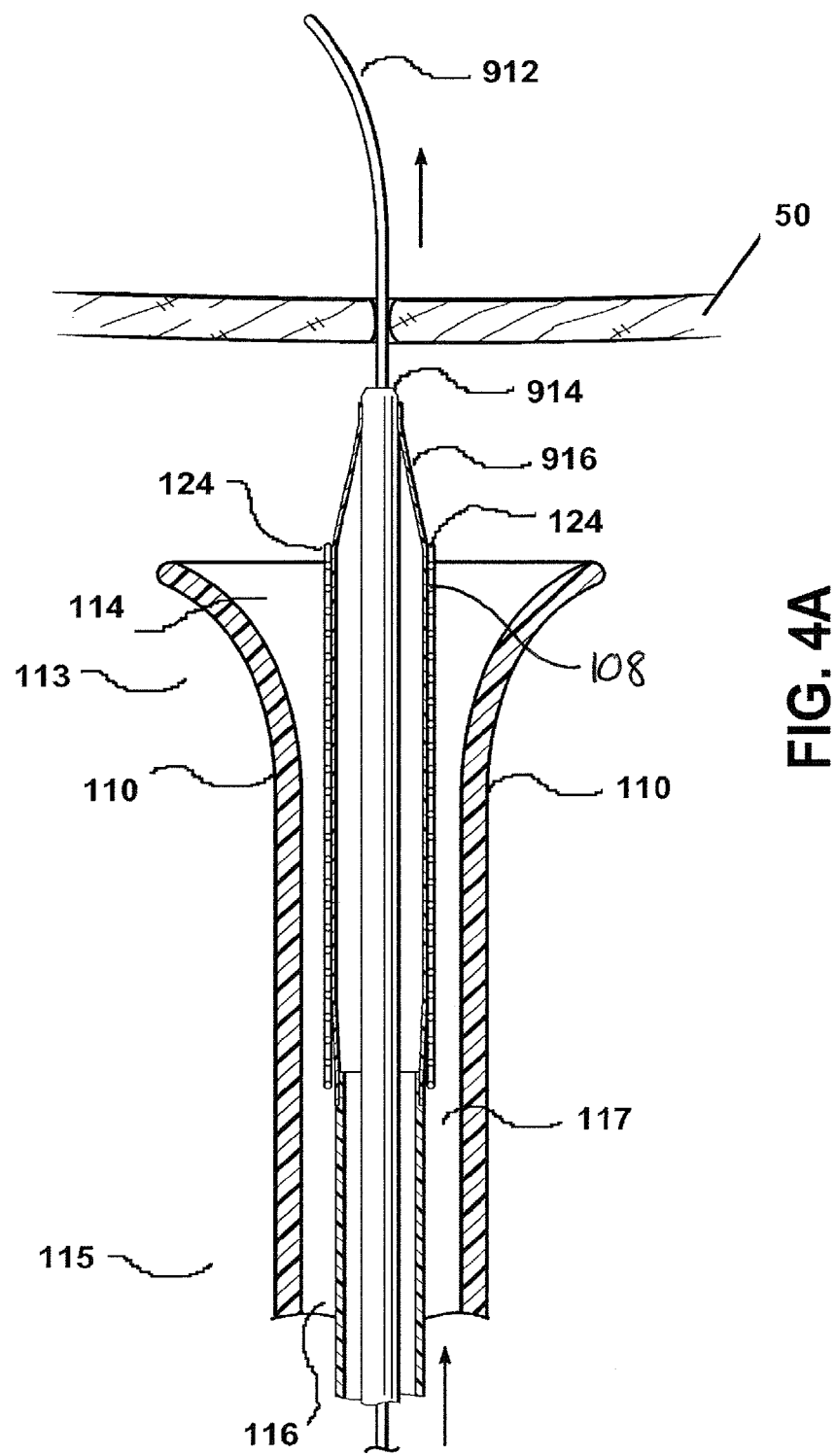
Figure 4B:
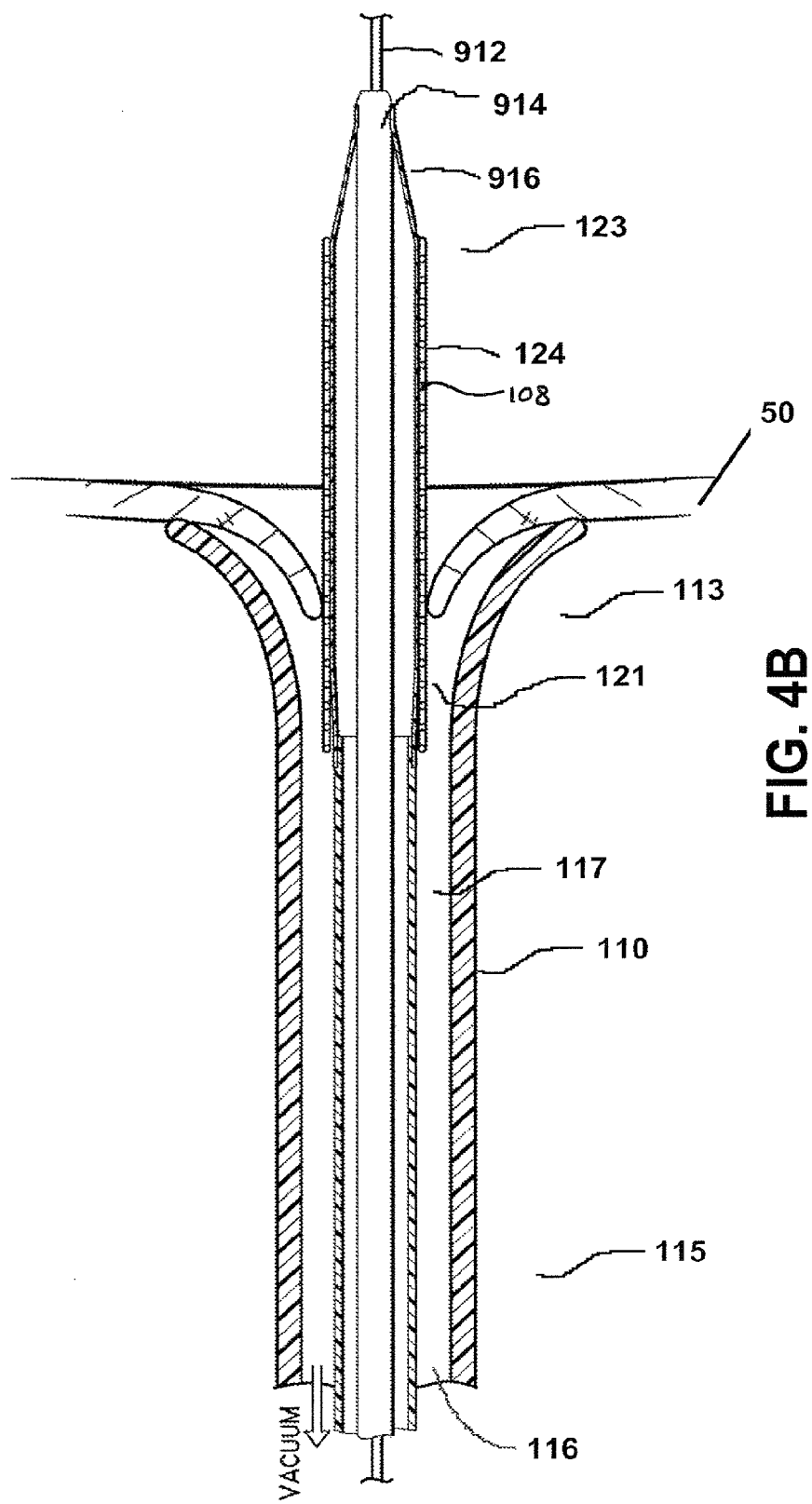
Figure 4C:
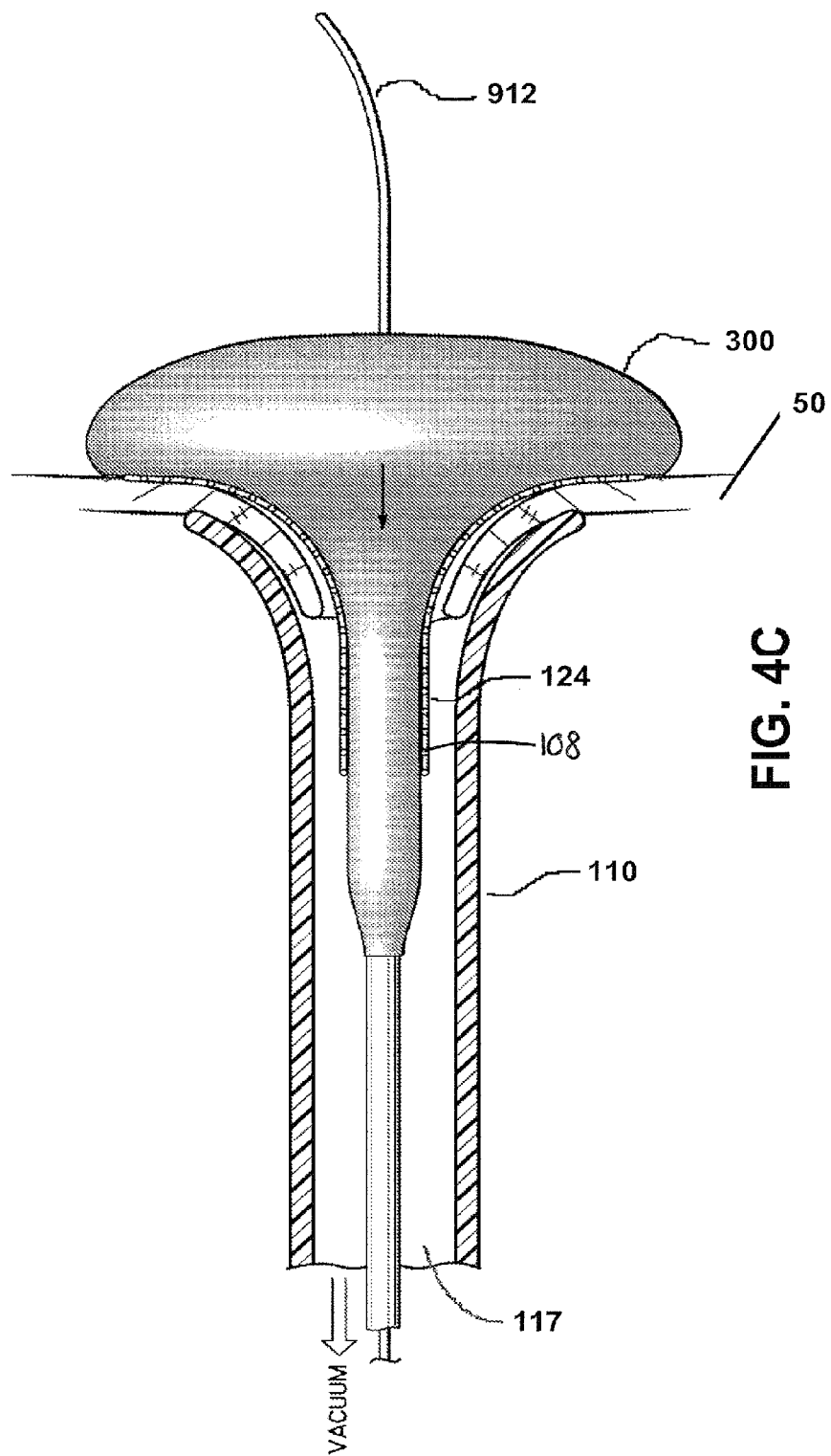

FIGS. 4A-4E provides another exemplary embodiment of a cannula system disclosed herein, wherein the hollow retention tube 100 is not be self-expanding and its placement into an organ chamber wall with another catheter assembly comprising a balloon. Generally, in FIG. 4A an elongate tubular member 110 with a trumpet-shaped distal end and a catheter assembly inside are shown outside the left atrium. A wire 912 has been introduced into the left atrium and a dilator 916 is positioned to guide the catheter assembly into the left atrium. In FIG. 4B, the catheter assembly has been introduced into the left atrium. A hollow retention member 124 comprising a stent 108 is mounted in a first configuration on a balloon 300 and is shown positioned partly inside the left atrium. The balloon 300 is shown partly inflated in FIG. 4C to expand the hollow retention member 124 and the catheter assembly is pulled back against the septum or atrial free wall. Simultaneously, or shortly thereafter, the elongate tubular member 110 is pushed forward against the septum or free wall of the atrium and the hollow retention member 124 begins to take a second configuration in the shape of the balloon.

Vacuum may be placed on the catheter assembly to pull the atrial tissue into the assembly.

Figure 4D:
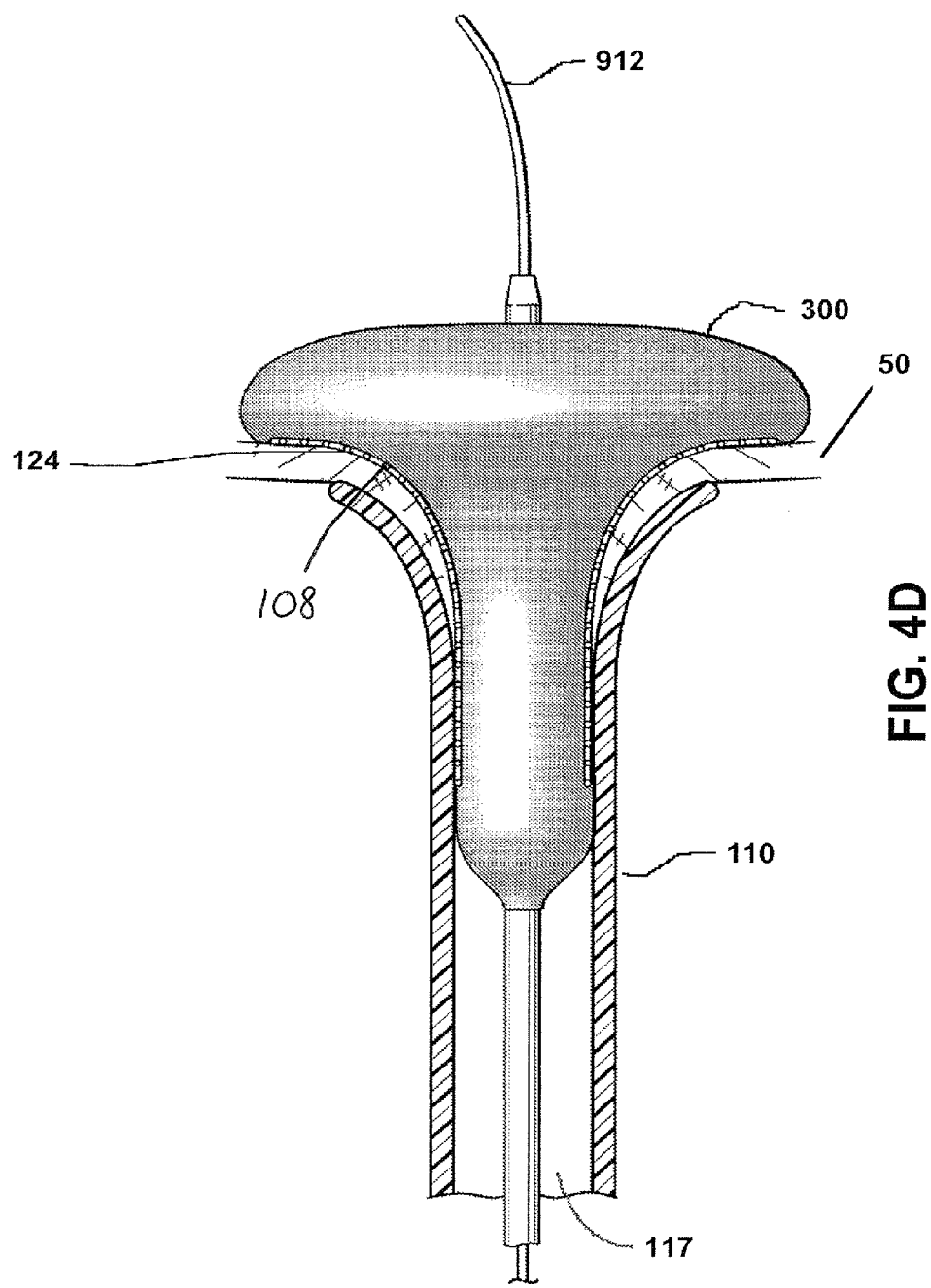

In FIG. 4D, the balloon 300 is fully inflated and the retention member 124 is fully expanded to its second configuration to a shape that conforms to that of the inner surface of the flared distal opening of the elongate tubular member 110. The atrial tissue 50 is now trapped between the retention member 124 and the elongate tubular member 110 and a fluid-tight seal is completed. The catheter assembly is shown withdrawn in FIG. 4E, and the elongate tubular member 110 is shown is shown attached to the atrial wall and entirely outside the left atrium.

Also shown in FIG. 4E is an optional reinforcement element 400 of a cannula system disclosed herein. The optional reinforcement element 400 is shown as surrounding the elongate tubular member 110 to help retain the system. The reinforcement element 400 may be disposed outside, inside, or within the wall of the elongate tubular member. The reinforcement element 400 may be constructed in any of a variety of ways including as a spring or a series of rings. This feature is designed to increase the counterforce of the elongate tubular member 110 against the hollow retention member 124 to improve attachment.

Also shown in FIG. 4E is a means for retaining the outside surface of the hollow retention member 124 against the chamber side of the organ wall and/or the tubular member 110 to the organ wall outside the chamber. The retaining element 122 shown in FIG. 4E is in the form of a plurality of elongate struts 127 that help retain the position of the hollow retention member 124, see also, e.g., FIGS. 3E, 4E, 7A, 8 and 17.

FIG. 4F shows an exemplary cannula system (including a reinforcement element 400) in fluidic communication with the left atrium, with the elongate tubular member 110 remaining outside the atrial wall and atrial tissue trapped between the hollow retention member 124 and the elongate tubular member 110. Again, the key benefits of the system, devices and methods as shown include the absence of a cannula tip in the atrium, which reduces the risk of clots and embolization, a much lower risk of suction with a broad flat entry for blood, a non-thrombogenic inflow pathway for blood (clot resistant), and no need for suture and a secure hemostatic attachment.

Figure 5:
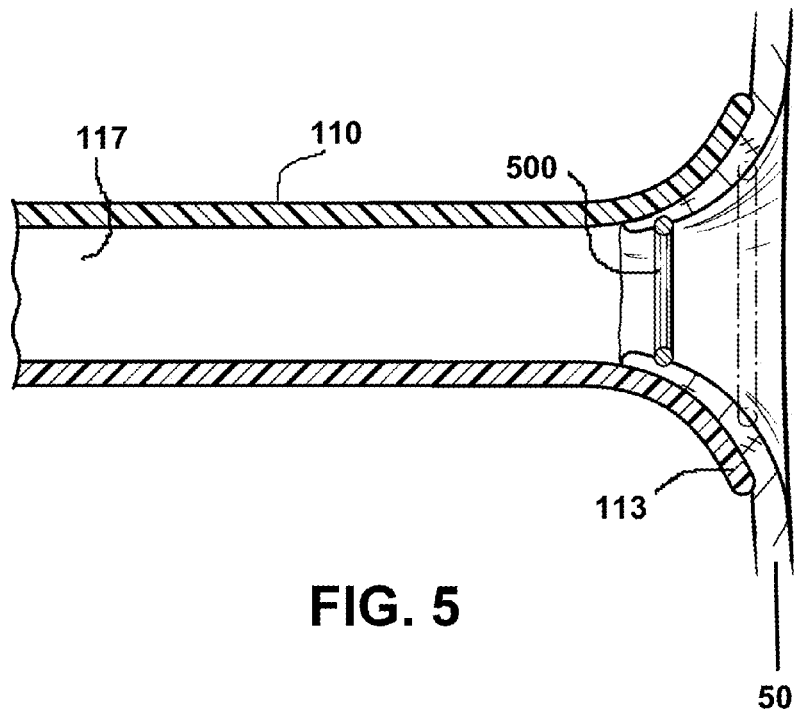
FIG. 5 is a longitudinal cross-sectional view of another exemplary cannula system in fluidic communication with a chamber of an organ.
Figure 6:
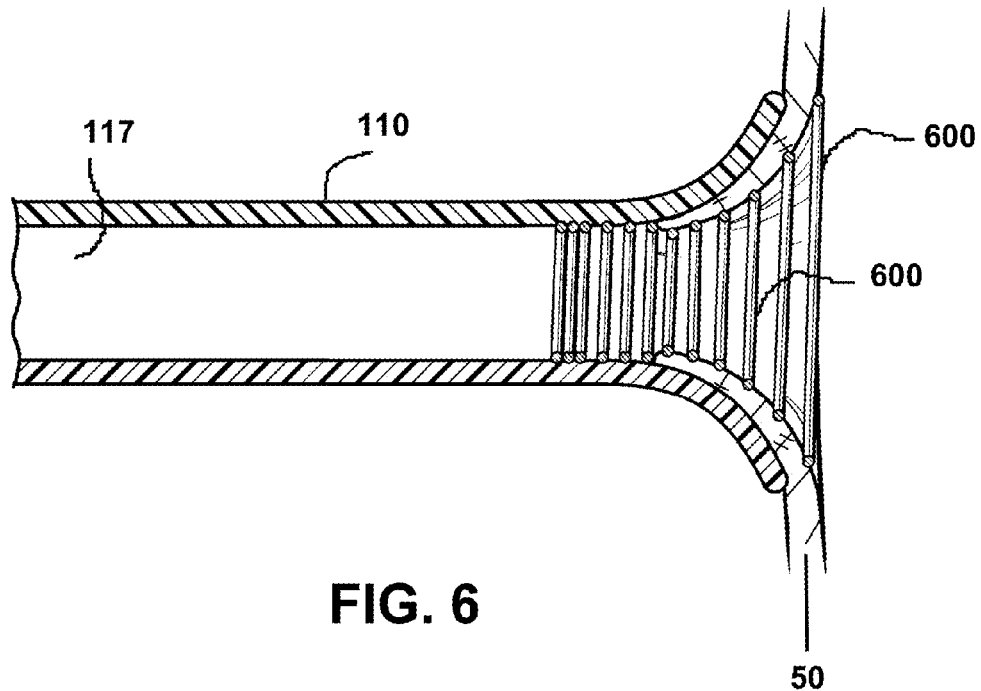
FIG. 6 is a longitudinal cross-sectional view of another exemplary cannula system in fluidic communication with a chamber of an organ.

As described above, FIG. 4E introduces a means for retaining, e.g., anchoring, one or both of (a) at least a portion of the outer surface of the retention member to the chamber side of the organ wall and (b) the tubular member to the organ wall outside the chamber. Other such retaining means, such as retaining elements, include one or more annular rings 500 holding the atrial tissue 50 and elongate tubular member 110 in place (FIG. 5), a spring 600 that has been released from a compressed state to retain the elongate tubular member 110 in place (FIG. 6), a plurality of barbs 125 to retain either or both the elongate tubular member 110 and the hollow retention member 124 to the atrial wall (FIGS. 7A, 7B, 7C, and 8), and a combination of these and any other retaining means, see e.g., FIGS. 7A and 8 (showing a combination of elongate struts and barbs).

Figure 7A:
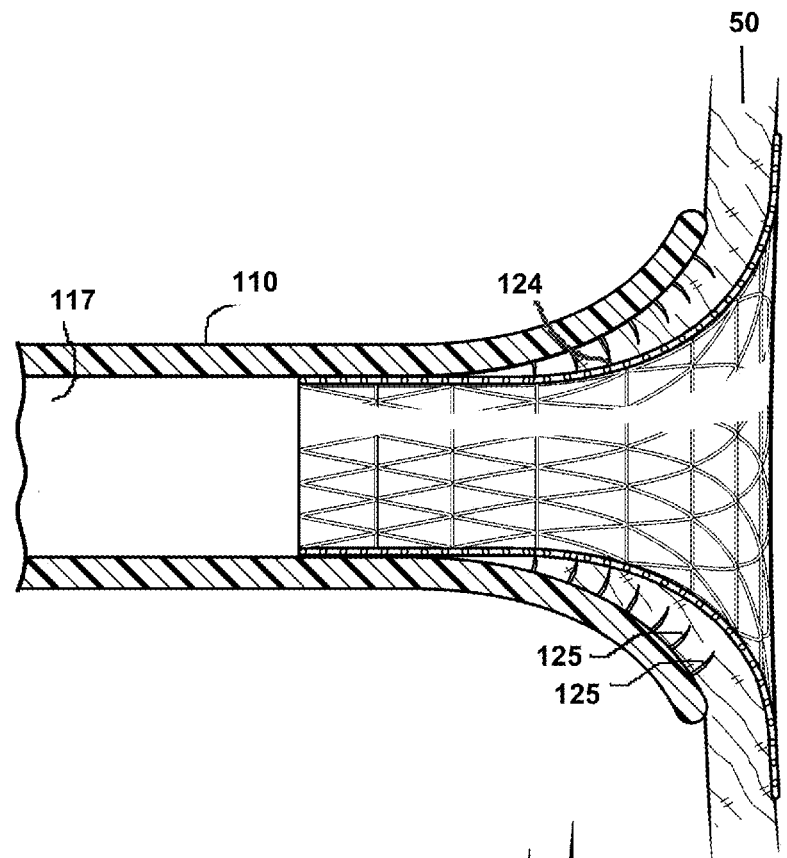
FIG. 7A is a longitudinal cross-sectional view of another exemplary cannula system in fluidic communication with a chamber of an organ.
Figure 7B:
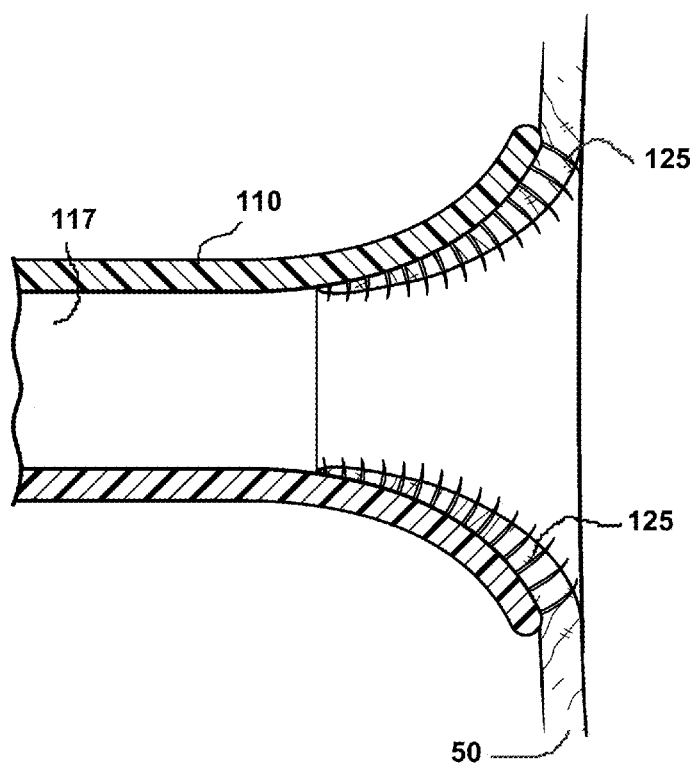
FIG. 7B is a longitudinal cross-sectional view of another exemplary cannula system in fluidic communication with a chamber of an organ.
Figure 7C:
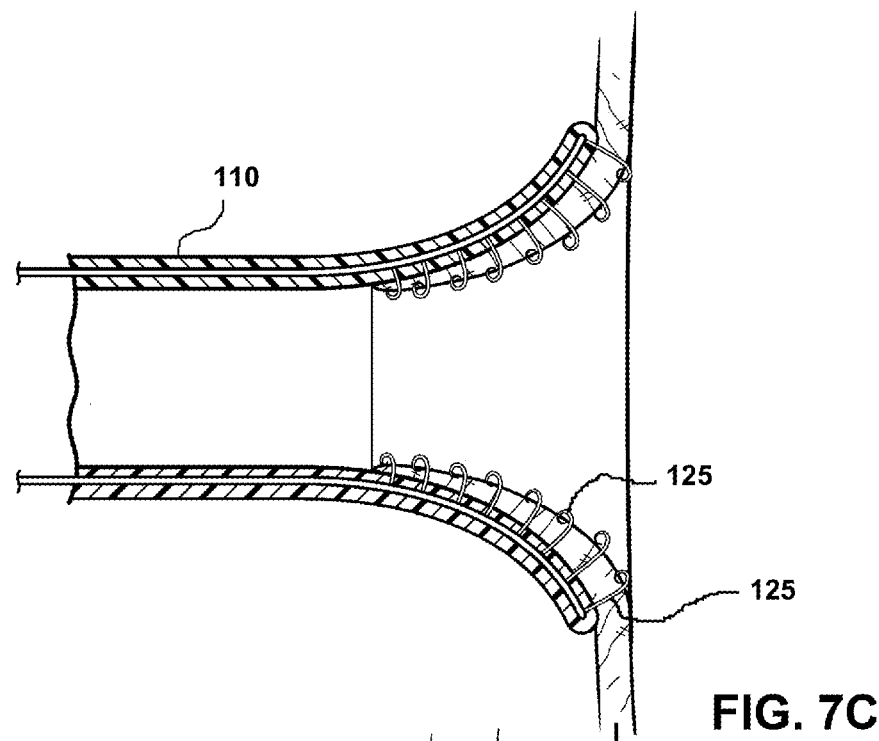
FIG. 7C is a longitudinal cross-sectional view of another exemplary cannula system in fluidic communication with a chamber of an organ.
Figure 8:
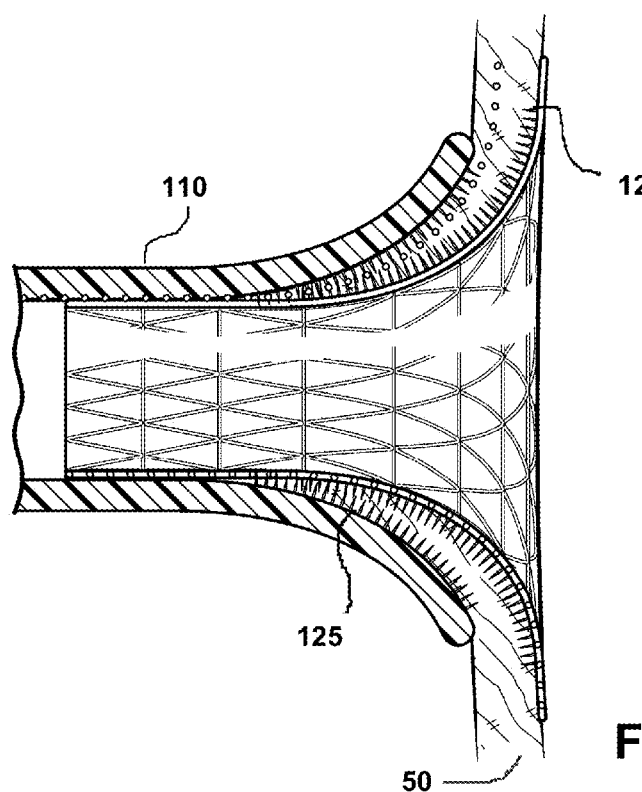
FIG. 8 is a longitudinal cross-sectional view of another exemplary cannula system in fluidic communication with a chamber of an organ.

In one embodiment, the retaining element 122 comprises a plurality of barbs 125 which may be by heat or current to curl or close or change shape such that the organ wall is retained, see, e.g., FIG. 7C. This can avoid the need for another retaining element 122. The barbs may be composed of nitinol and take this shape, or other shapes, on activation. Other shapes could be used to retain the hollow retention member 124 and/or elongate tubular member 110. In one embodiment, a balloon inflated against the atrial tissue may be used push the barbs into the atrial wall.

The cannula system 100 featured in the preceeding figures comprise a hollow retention member 124 that is separate from an elongate tubular member 110, which preferably has a flared distal opening. This configuration allows subsequent removal of the hollow retention member 124 from the organ chamber and system after the inner surface of the flared distal opening of the elongate tubular member 110 has been anchored to the outer surface of the organ chamber wall. For example, the hollow retention member 124 may be compressed into its first configuration, as it is withdrawn through a hole in the wall and the elongate tubular member and/or via a sheath.

As described above, in one embodiment of a cannula system disclosed herein, the hollow retention member 124 and the elongate tubular member 110 are manufactured integrally connected to form a cannula or inflow tube 10. As will be demonstrated in the following figures, even in these embodiments, the retaining element 122 is configured to anchor at least a portion of the flared distal end 13 of the inflow tube 10, to the chamber side of the organ wall.

Accordingly, also described herein is a cannula system comprising a inflow tube 10 having a proximal end 15, a tubular body 11, a distal end 13, an outer surface 28, and a lumen 17 extending between a proximal opening 16 at the proximal end 15 and a distal opening 14 at the distal end 13, the distal end 13 being self-expandable between a first configuration in which the distal opening 14 is substantially closed, and a second configuration in which the distal opening 14 is open and in which the perimeter of the outer surface 28 of the distal end 13 is larger than the perimeter of the outer surface 28 of the tubular body 11, at least a portion of the outer surface 28 of the distal end 13 including a material 804 suitable for promoting tissue ingrowth when the portion of the outer surface 28 of the distal end 13 is in contact with an atrial septum of a heart, the material 804 forming a circumferential step 806 at the junction between the material 804 and the distal end 13; a retaining element 122 configured to secure the distal end 13 to the atrial septum with the distal opening in fluidic communication with the left atrium of the heart and with the inflow tube 10 extending through an opening in the septum and into the right atrium; and a delivery catheter 910 including a compression element releasably engaged with the distal end to selectively maintain the distal end in the first configuration and to allow the distal end to self-expand to the second configuration.

As described herein the compression element may be a sheath 202 disposed about the outer surface 28 and movable proximally relative to the cannula 10 from a first position in which the sheath 202 engages the outer surface 28 of the distal end 13 and a second position in which the sheath 202 is not engaged with the distal end 13. In another embodiment, the compression element may be a compression tip 204 movable distally relative to the cannula 10 from a first position in which the compression tip 204 engages the outer surface 28 of the distal end 13 and a second position in which the compression tip 204 is not engaged with the distal end 13.

Figure 9B:
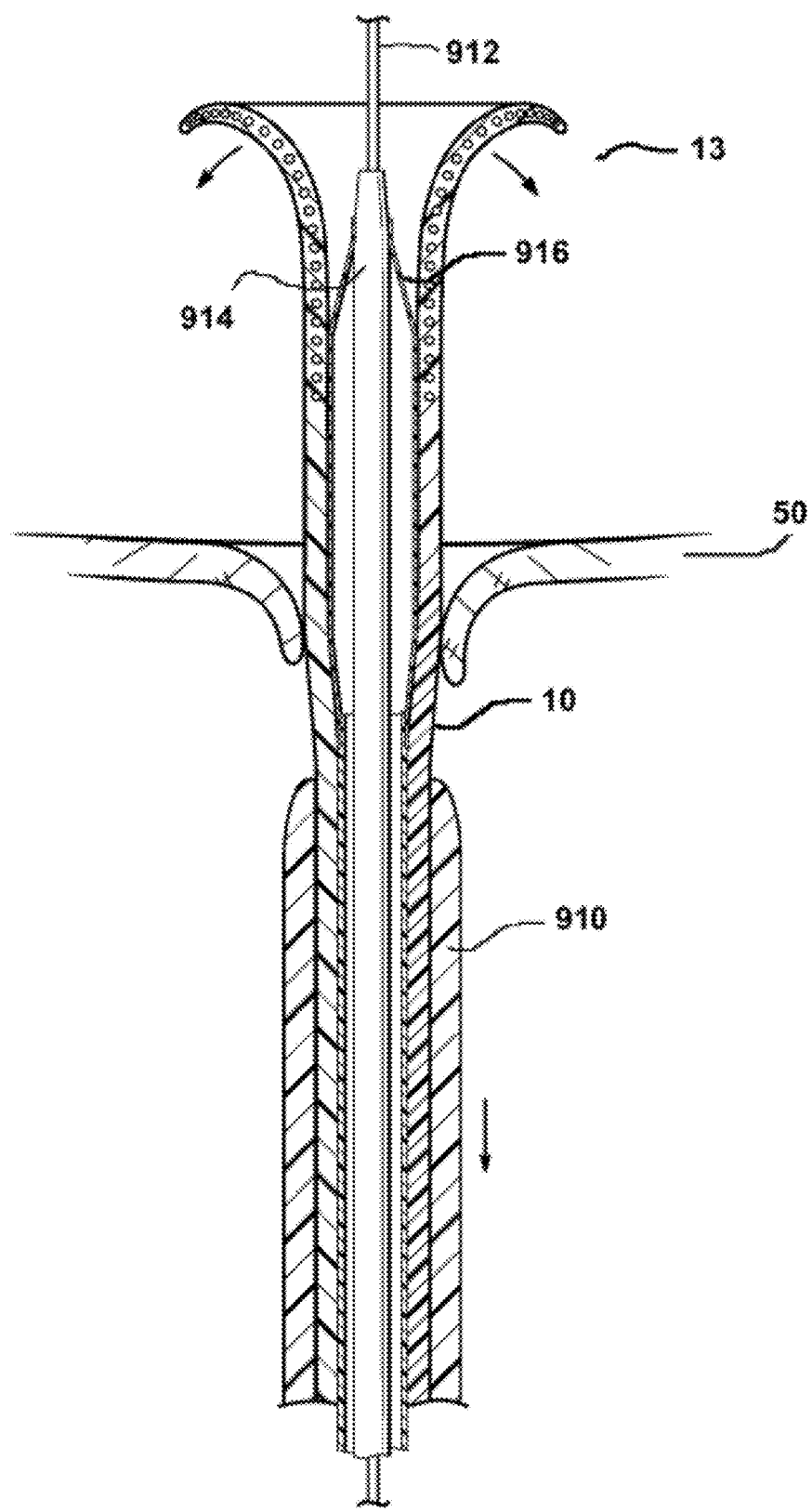
Figure 9C:
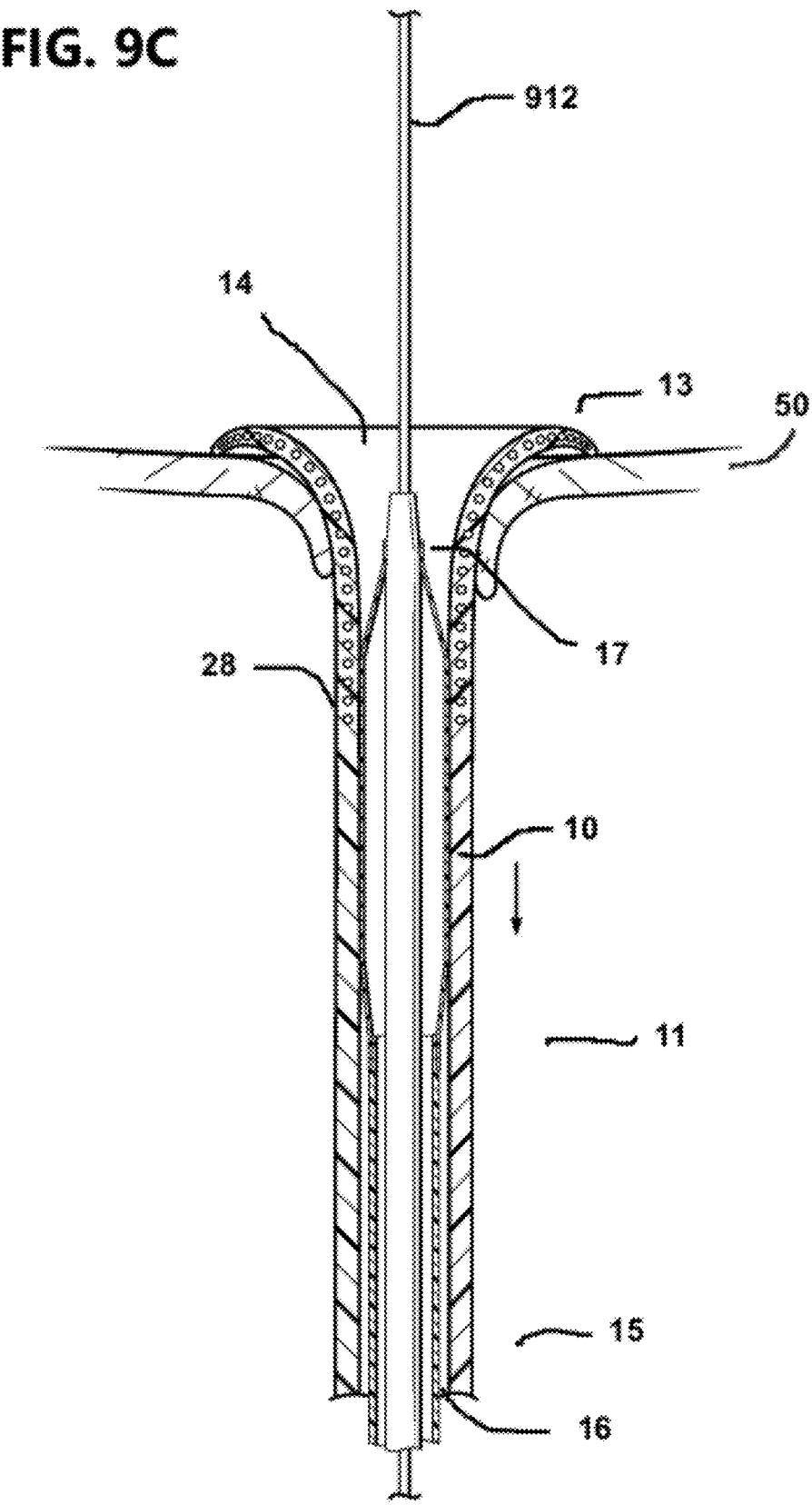
Figure 10A:
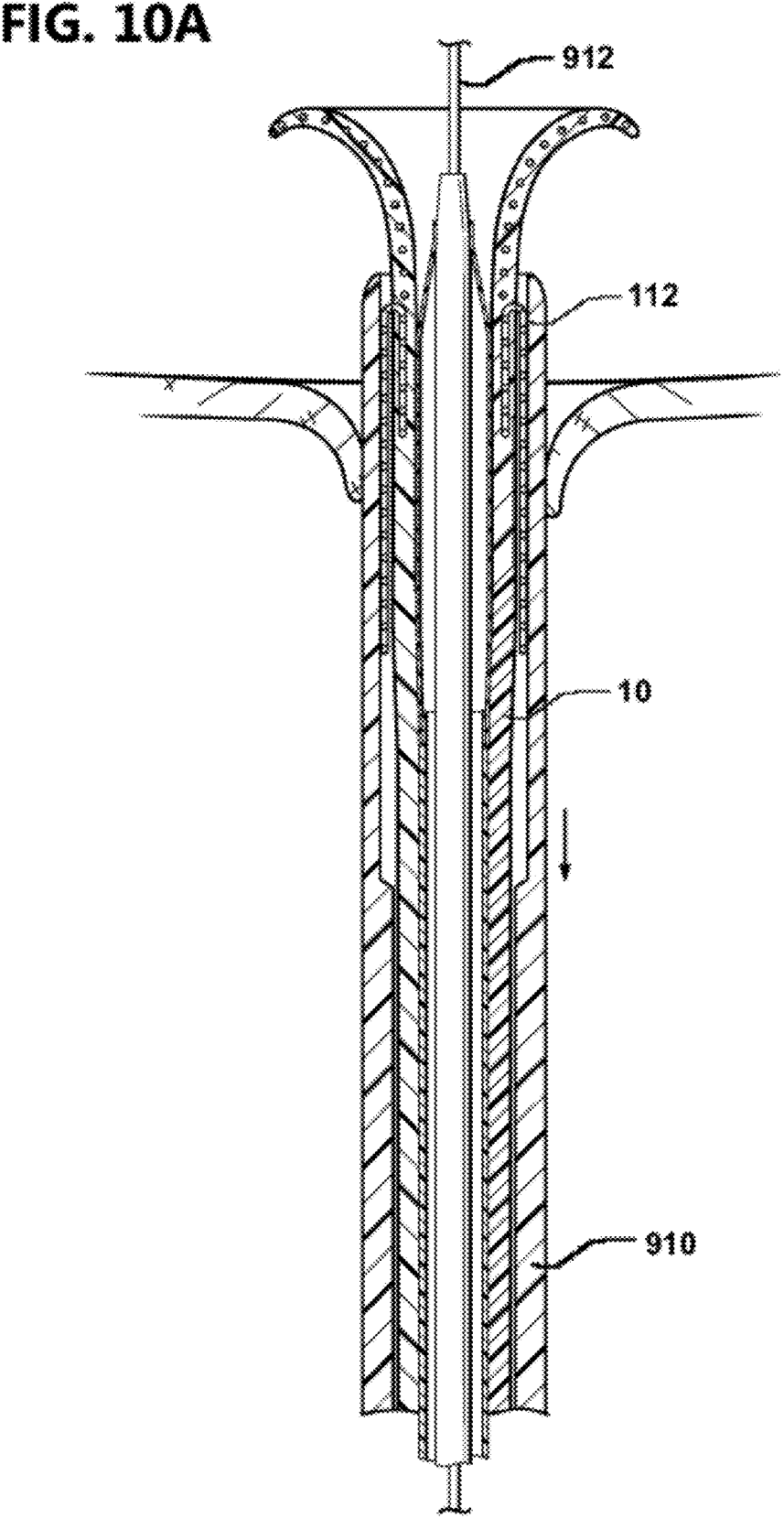
FIGS. 10A-10C are longitudinal cross-sectional views of another exemplary cannula system and an exemplary method of placing the cannula system into fluidic communication with a chamber of an organ using a catheter delivery system.
Figure 10B:
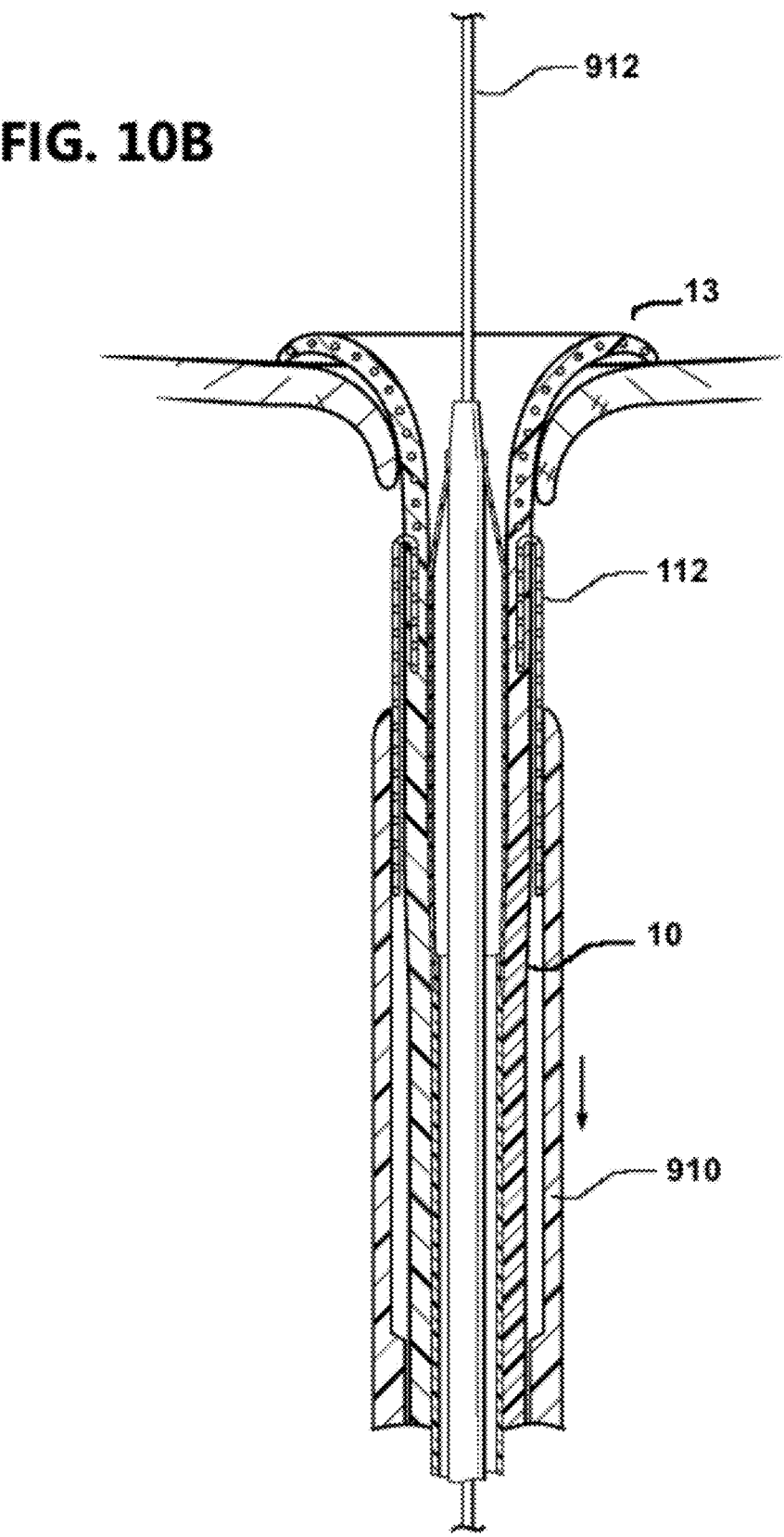
Figure 10C:
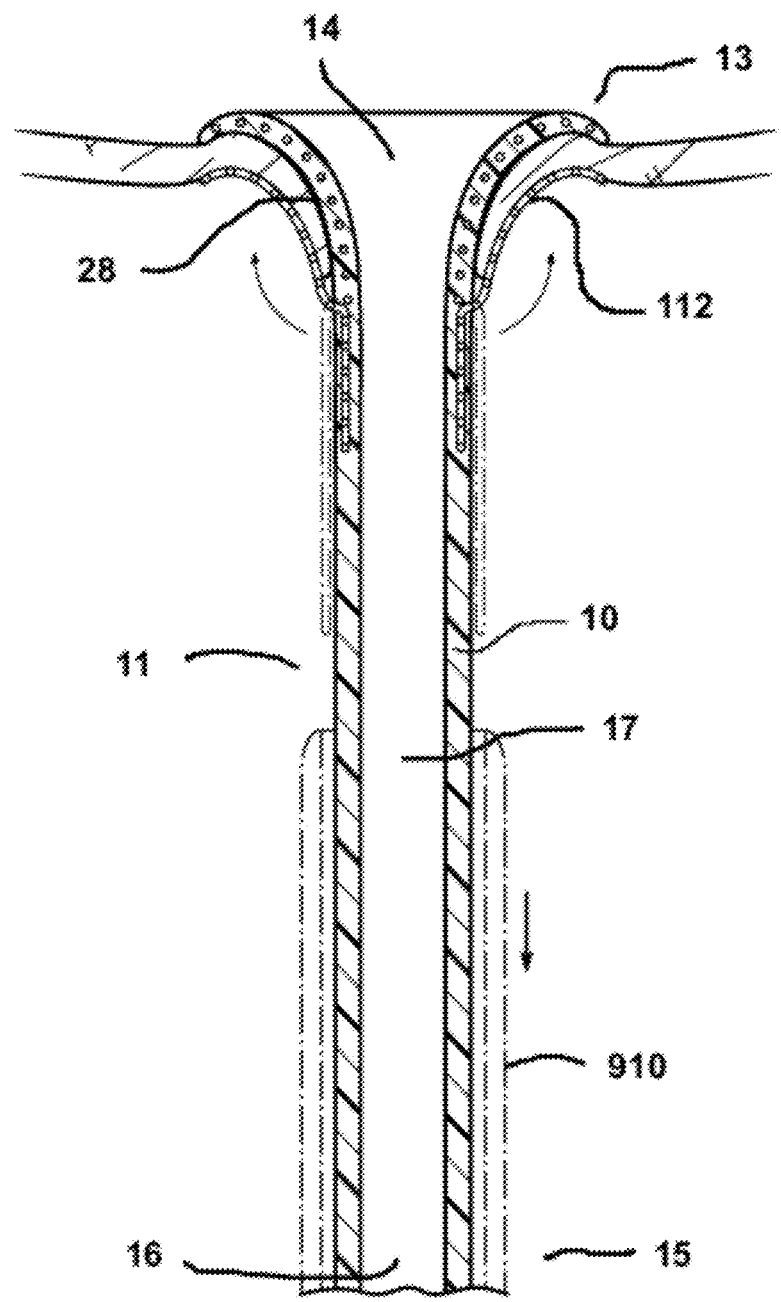

For example, in FIGS. 9C and 10C, a cannula system in which the elongate tubular member 110 and hollow retention member 124 are manufactured as one inflow tube 10 is shown. In FIG. 9A, the inflow tube 10 is shown inside a catheter 910 of a catheter assembly. In this embodiment, distal end 13 of the inflow tube 10 is self expanding and the catheter 910 is also acting as a sheath 202 to maintain the distal end 13 of the inflow tube 10 in the first configuration. Within the inflow tube 10 is a dilator 916 which is used to stretch an opening in the atrial tissue. The dilator has a central lumen to allow it to pass over a wire 912. The cannula system and catheter assembly is shown as it is being pushed into the atrium in the direction of the arrow. Also shown in FIG. 9A as circles within the cannula is a reinforcement element 400 in the shape of a wire, such as stainless steel or nitinol, which has shape memory properties to ensure the cannula tip returns to the ideal shape after deployment.

The inflow tube 10 would be deployed by first puncturing the atrial wall or interatrial septum. For use in blood pumping from the left atrium, a needle or wire 912 is first delivered into the cavity and used to guide the assembly shown in FIG. 9A. The small wire entry point can then be dilated to enlarge the opening into the left atrium. The entire catheter assembly can then be placed inside the left atrium. In FIG. 9B, the catheter 910 has been withdrawn and the distal end 13 of the inflow tube 10 is now expanded inside the atrium. In this embodiment, the cannula is self-centering and the inflow tube 10 centers itself inside the defect the dilator has created such that the flared distal end 13 of the singular inflow tube 10 may seal the entry site. In FIG. 9C, the inflow tube 10 is now moved backward toward the left atrial wall as the remainder of the catheter assembly is removed. Also, the operator will feel the attachment and drag on the cannula as it anchors against the trial tissue. FIG. 9D depicts the cannula system in fluid communication with the left atrium and an additional retaining element 700 that traps atrial tissue to at least a portion of the outer surface of the flared distal end of the inflow tube 10 in a lock and key fashion such that at least a portion of the trapped wall conforms to the shape of the flared distal end 13 of the inflow tube 10. The atrial wall is mobile and by trapping the mobile tissue and shaping it to engage between the flared distal end of the inflow tube 10 on the inside and the retaining element 700 on the outside, the risk of a gap in the connection is reduced. The strong locking reduces the risk of leaking of blood or suction of air—as it produces a water tight and air tight connection.

The particular retaining element 700 shown in FIG. 9D may be applied by sliding it along the outside of the elongate tubular member until the tissue is trapped. It may be held in place by many mechanisms including friction, threads, a washer etc. The retaining element 700 may consist of a simple metal or polymer material or a combination of metal and polymer that can slide along the outside of the elongate tubular portion of the inflow tube 10. It may be introduced after the inflow tube 10 is placed inside the atrium—apart from the system shown in this series of figures.

In one embodiment, the retaining element 700 may be pre-positioned at a fixed but adjustable distance proximal to the distal end 13 of the inflow tube 10. When the operator introduces the distal end 13 of the inflow tube 10 into the atrium, the retaining element 700 may act as a stopper to demonstrate to the operator that the distal end of the inflow tube 10 is safely inside the atrium. The inflow tube 10 may then be withdrawn until the flared distal end 13 is snug against the inside of the heart and the retaining arm can be maneuvered along the elongate tubular member to its final position.

Another important feature of the retaining element 700 is to provide an excellent approximation between the distal end 13 of the inflow tube 10 and the atrial tissue. As a means of circumferentially engaging the outer surface 28 of the flared distal end 13 of the inflow tube 10 to the chamber side of the organ wall 50, the retaining element 700 works from both sides of the atrial wall as it ensures that the entire circumference of the distal end 13 of the inflow tube 10 is firmly touching the atrial wall. This avoids leaving a gap that could allow the formation of a clot that could be drawn into the inflow tube 10 and thence into the blood pump and into the patient's circulation, with the attendant risks to the patient described above.

A retaining element 122 may also be coupled directly to the inflow tube 10, see, e.g., FIGS. 10A-10C. For example, in FIG. 10A, a retaining element 122 is shown as a retaining arm 112 extending from and folded against the inflow tube 10. It may be held folded inside a catheter 910 during insertion and may self deploy to anchor the outer surface of the distal end of the inflow tube 10 to the atrial wall as the catheter 910 is withdrawn. Preferably, the deployed retaining arm 112 is a shape in conformity with the flared distal end 13 of the inflow tube 10. As shown in FIGS. 10A-10C, the cannula system and catheter assembly are introduced into the atrium as described for FIG. 9A. FIG. 10B shows the inflow tube 10 positioned against the atrial wall as described previously for FIG. 9B In FIG. 10C, the dilator 916 tipped obturator 914 has been withdrawn and the inflow tube 10 is positioned against the atrial wall. The retaining arm 112 "sprung" into position (curved arrows) upon release from the catheter, e.g., withdrawal of the catheter (straight arrows). The retaining arm 112 traps the atrial tissue, optionally a means of circumferentially engaging the outer surface 28 of the flared distal end 13 of the inflow tube 10 to the chamber side of the organ wall 50, to the outer surface of the flared distal end of the inflow tube 10 as a retaining means, to aid in preventing the entry of fluid leak/air entry, and to ensure that the margin of the flared distal end of the inflow tube 10 is securely pressed against the atrial tissue.

The retaining arm 112 may be made from a flexible material such as nitinol that springs into the closed position of FIG. 10C, but is bent backwards inside the catheter 910 during delivery. This retaining arm 112 could also be covered by a fabric to encourage healing into the heart tissue.

Figures 11A, 11B, 11C:
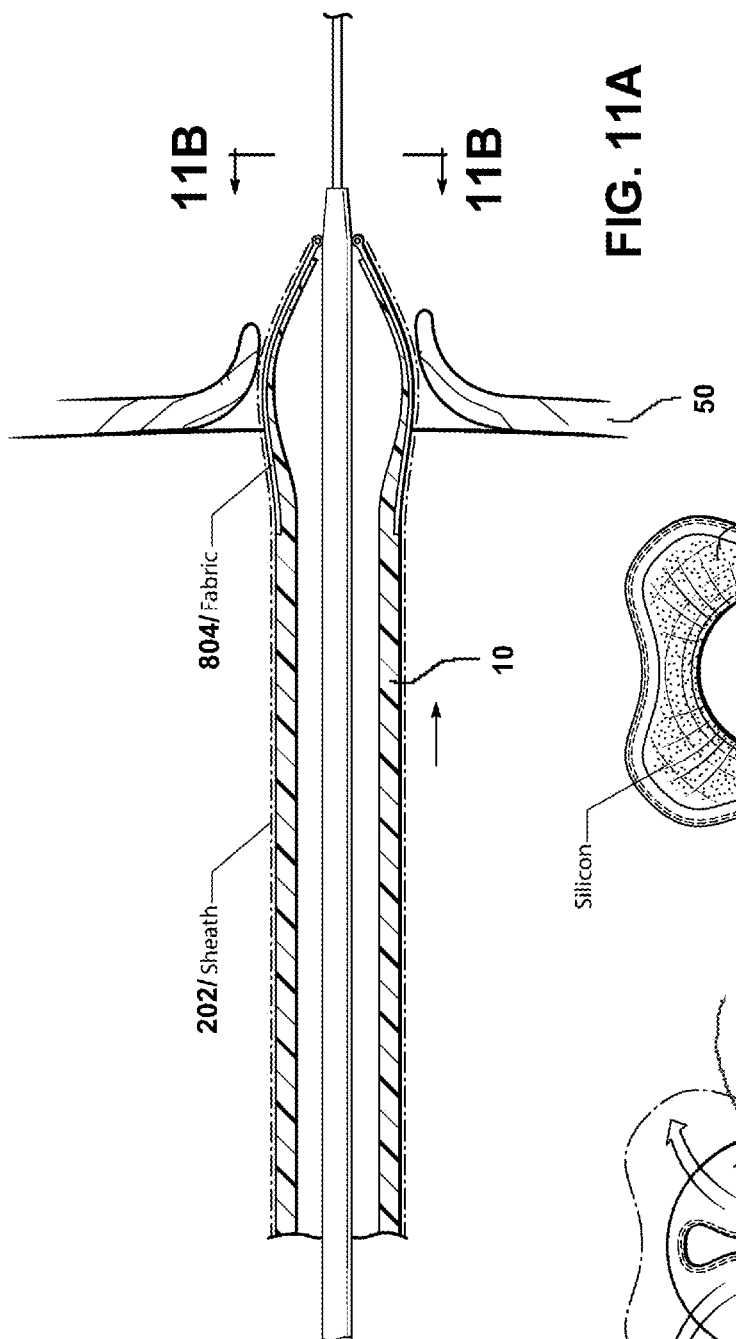
FIG. 11A is a longitudinal cross-sectional view of another exemplary cannula system being placed into fluidic communication with a chamber of an organ using a catheter delivery system.
FIG. 11B is an enlarged cross-sectional view of the distal end of the cannula system of FIG. 11A, in a first, compressed configuration, taken along line 11B-11B of FIG. 11A.
FIG. 11C is an enlarged cross-sectional view of the distal end of the cannula system of FIG. 11A, in a second, expanded configuration, taken along line 11B-11B of FIG. 11A.

The hollow retention member 124 or flared distal end 13 of a inflow tube 10 does not necessarily need to expand to a perfect circular opening. In one embodiment, the hollow retention member 124 or flared distal end 13 of an inflow tube 10 may expand into "leaves or lobes." For example, FIG. 11A shows latitudinal cross-sectional view of the distal end 13 of an inflow tube 10 that expands into a plurality of "leaves or lobes" 109. FIG. 11B shows an important potential advantage of these leaves. In FIG. 11B the leaves have been compressed by a compression means or element into a closed position. The arrows show how they can self-expand into the flared configuration of FIG. 11C. This variation allows folding to a shape like FIG. 11A, to create a blunt tip, such as a "bullet" shape, that can be used to allow smooth passage of the inflow tube 10 without catching tissue, and even to function as a dilator to stretch an opening in the atrial tissue. In FIG. 11A, the inflow tube 10 is delivered inside a sheath 202. It has a fabric backing 804 on the flared distal end of the inflow tube 10 that will come to rest against the atrial wall.

A skilled artisan will recognize that the distal end does not need to have four leaves. Two or three might perform the same function. Or, to facilitate folding, the distal end of the inflow tube 10 may be formed with a plurality of leaves or lobes.

FIG. 11C shows how this may be constructed. The core of the inflow tube 10 may be made from a polymer such as silicone or urethane (shown here in shading and labeled Silicon). The outer surface the distal end of the inflow tube 10 (its outside) that interfaces the atrial wall in the final position may have a fabric coating 804, or roughened surface, that extends beyond the perimeter of the silicone to create a step 806.

In FIG. 11C, a wire is shown as a dotted line that can be used to keep this shape to the four leaves. The wire could be housed inside a fabric (like a closed sock) so it does not touch tissue and is not exposed to blood. Wire, such as nitinol with shape memory characteristics, may be a good choice for this location. The wire which creates the leaves may have important three-dimensional characteristics. In addition to creating a multi-sided leaf shape, it may also be important to have this wire curve backward toward the atrial wall in a direction orthogonal to the leaf shape. This will facilitate the contact with tissue. The wire may be more than just a simple single loop. It could be a series of wires in the fabric, in the silicone or both in the silicone and fabric. It is also possible that a stent structure could perform the same function—a nitinol or stainless steel stent could be within the fabric, the polymer or in both.

In FIG. 11C the margin of the silicon core of the cannula generally follows the course of the four lobes. It is also possible for the silicon to deviate from the path of the fabric 804. For example, the margin of the silicon could also be circular or otherwise not precisely follow the fabric margin of the inflow tube 10.

Figure 11D:
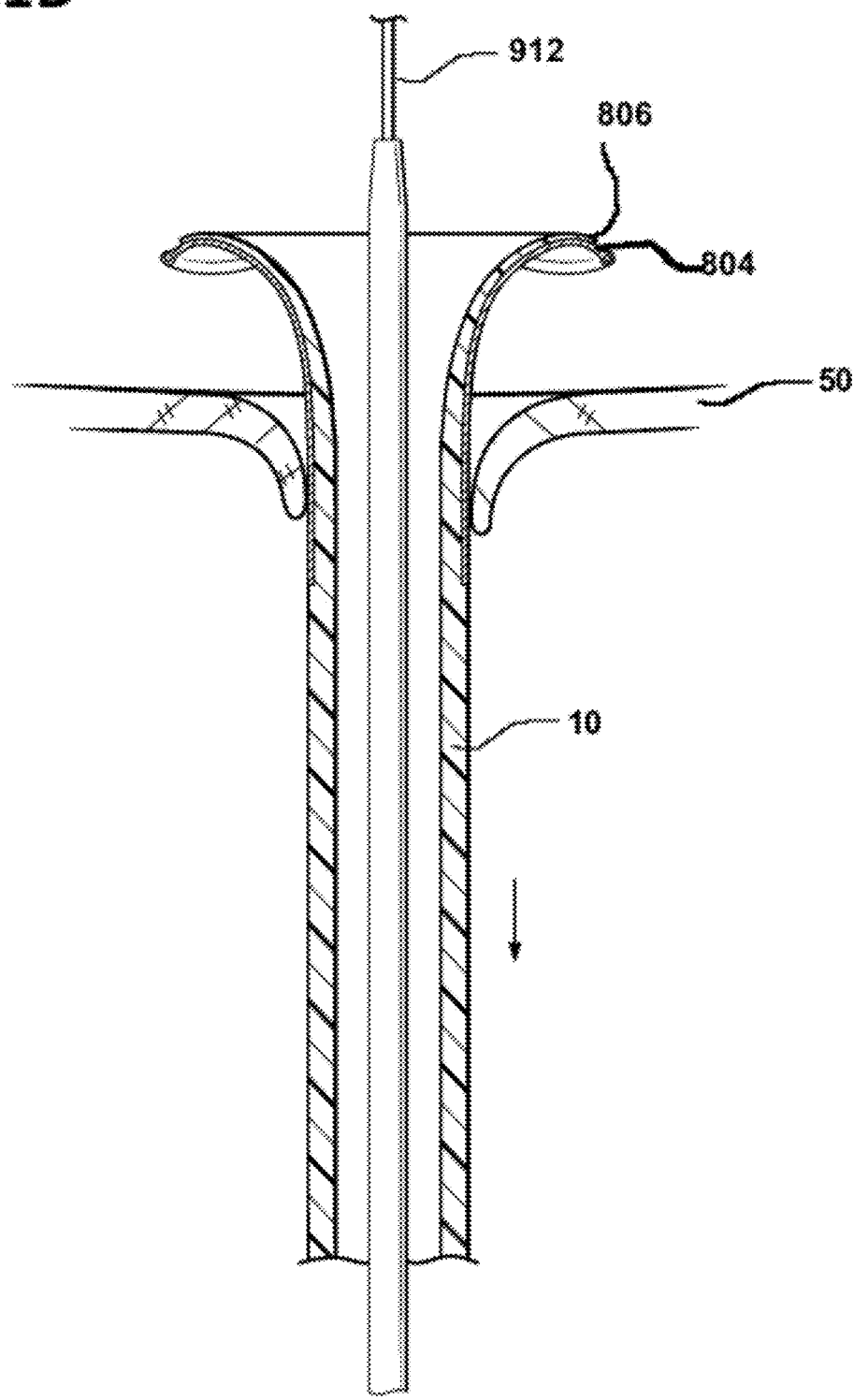
FIG. 11D is a longitudinal cross-sectional view of the cannula system of FIG. 11A in the second configuration.

Shown in FIG. 11D is one embodiment that incorporates principles described herein. A inflow tube 10 is shown with the distal end in a flared second configuration which could have any number of leaves. The wire helps the distal end retain its shape and provides a solid edge to the inflow tube 10 at the point where it contacts tissue. A fabric backing 804 is shown. The fabric covers a wire at the margin of the trumpet tip. Alternatively the fabric, the cannula may have a roughened surface which functions to encourage tissue adhesion and eliminate the need for fabric.

The wire does not need to be in a circle—it could be formed in a zig-zag pattern that is easier to fold for insertion. An ordinarily skilled artisan will recognize that if the cannula is stiff enough, e.g., of adequate thickness, it may not at all be necessary to have a wire cannula. The cannula may retain its shape alone without support.

Figure 11E:
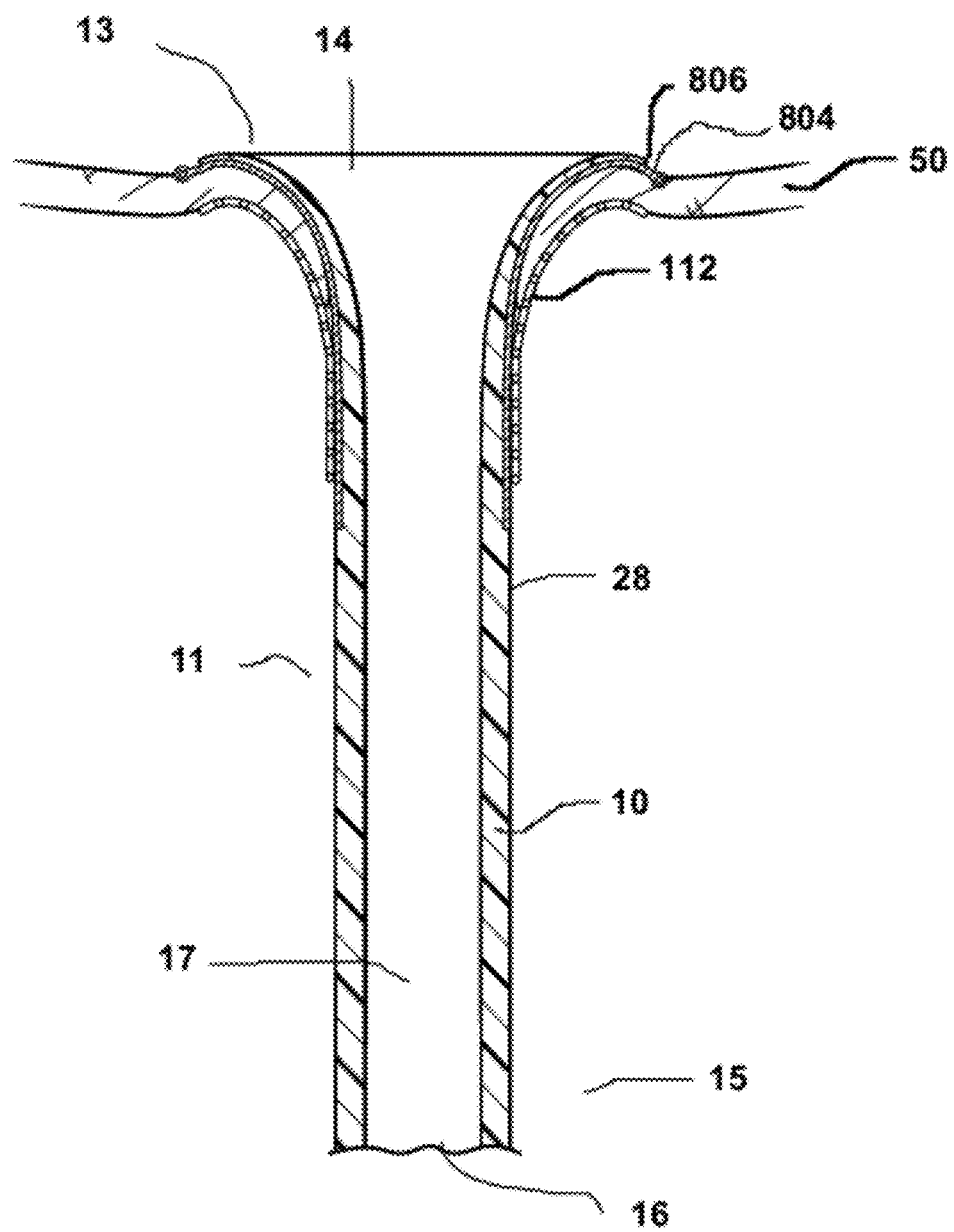
FIG. 11E is a longitudinal cross-sectional view of another exemplary cannula system in fluidic communication with a chamber of an organ.

FIG. 11E shows a cannula system as described in fluidic communication with the left atrium of a heart. The atrial wall or atrial septum is trapped between the outside surface of the flared distal end of the inflow tube 10 and the retaining arm 112. The fabric material 804 on the cannula is held in position by a wire around its margin. The polymer material sits on the fabric material 804 and there is a small step 806 up along the polymer surface where it meets the fabric to mimic the situation found in a heart valve and to encourage tissue to grow from the wall of the heart, along the roughened fabric surface, but stop at the polymer material in the cannula.

In another embodiment, a cannula system need not be placed in fluidic communication with an organ chamber with a catheter assembly. For example, in FIG. 12A, the cannula system is not inside a catheter assembly. The distal end of the inflow tube 10 is compressed in the first folded shape by a compression means.

In this figure, a dilator catheter has a central opening to allow passage of the system over a guidewire. As long as the dilator and distal end of the inflow tube 10 are held together, the distal end of inflow tube 10 is compressed into a first configuration and is compact and easy to insert inside the heart. In this embodiment, the dilator acts a means for compressing the distal end of the inflow tube 10, e.g., as a compression tip 204 and inflow tube 10 has just been pushed inside the left atrium, although the distal end is not ready for expansion into a second configuration until it is farther inside.

In FIG. 12B, the cannula system and dilator assembly have been pushed further inside the atrium. The dilator tip has then been pushed forward to allow the distal end of the inflow tube 10 to "spring open" to reform into its generally flared shape.

A wire (labeled Hoop) is shown. This is a zig zag shaped wire that allows the trumpet tip to reform after unfolding. Note that a wire would not have to have a zig zag shape. A circular wire could be folded inside the dilator tip, but packing and stability may be better with a preformed zig zag wire. Also, with enough folds, the margin of perimeter of the distal end of the inflow tube 10 effectively becomes a circle.

In FIG. 12C, the distal end of the inflow tube 10 is expanding; with many folds, the generally circular shape is regained and the inflow tube 10 is pulled back, proximally against the inner wall of the heart chamber (in the direction indicated by the arrow). It is approaching its final position. The atrial wall is dragged with the distal end of the cannula and begins to take the general curve of the outer wall of the cannula.

Figure 12D:
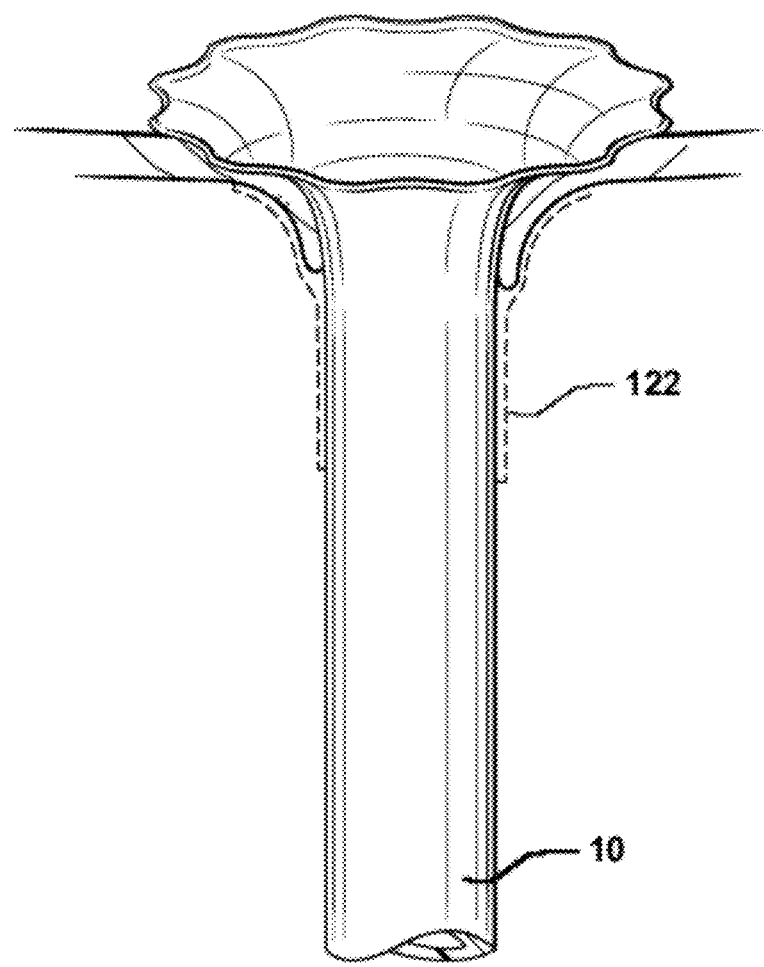
FIG. 12D is a longitudinal cross-sectional view of another exemplary cannula system in fluidic communication with a chamber of the organ.

In FIG. 12D, the inflow tube 10 is shown in fluidic communication with the left atrium. Although this figure does not depict a fabric backing, circumferential step, etc., at the interface of heart tissue and the cannula, all these features may be incorporated here. Also depicted in this figure is a means for retaining the cannula, trapping atrial tissue, etc. This means may comprise any of the retaining elements previously described and a combination thereof.

Notably, as depicted, there is no need for a catheter assembly to place the cannula system in fluidic communication. The distal end of the inflow tube 10 is bent inward and held by a compression means, e.g., the tip of a dilator. This solves many of the disadvantages associated with use of a catheter assembly, e.g, the cannula system may stick to a catheter wall and considerable engineering and expense is necessary to guarantee delivery. Even with good engineering, bends along the course may prevent easy delivery of the cannula system or blood can get inside the catheter, clot and lock the cannula system inside the catheter.

Figure 12E:
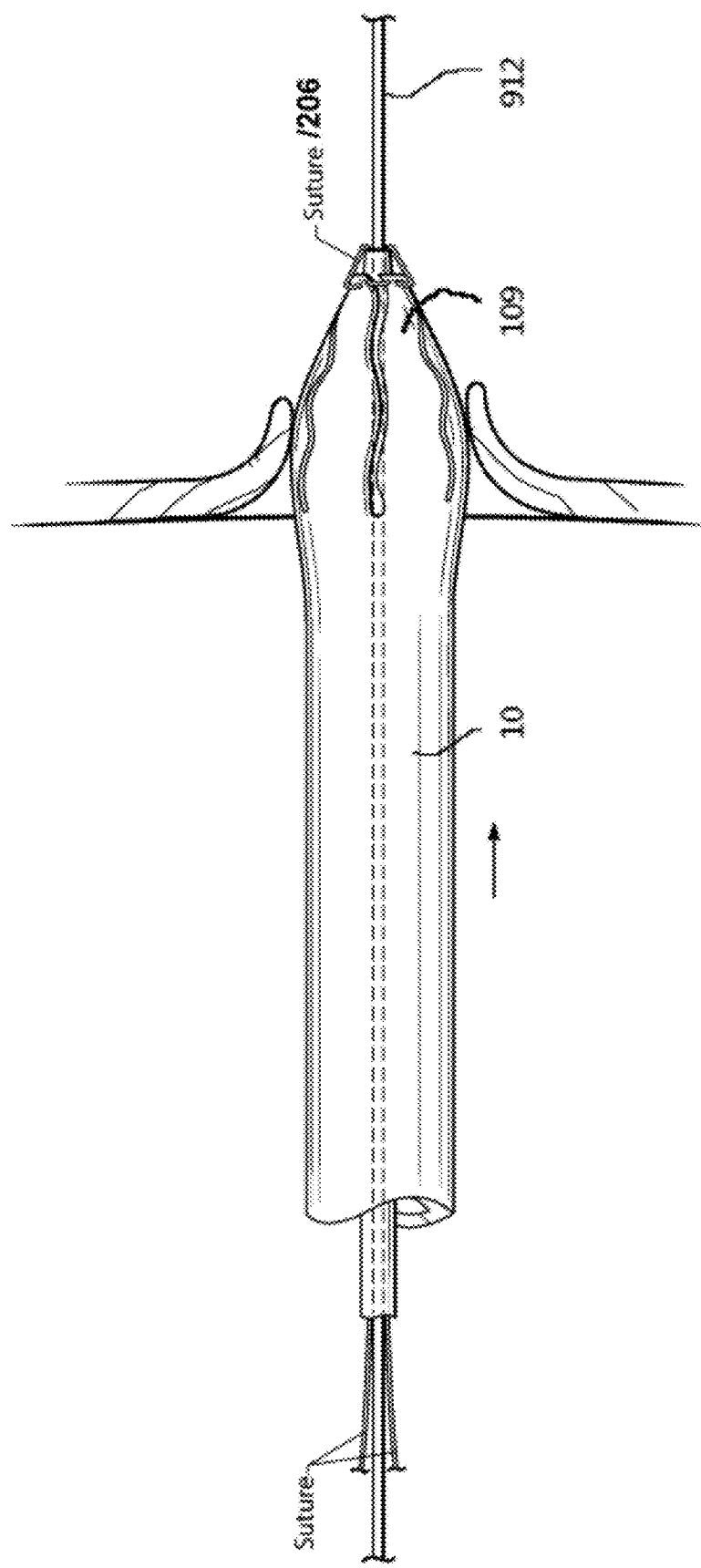
FIG. 12E is a longitudinal cross-sectional view of an alternate method of implanting the cannula system of FIGS. 12A-12C.

A dilator tip was shown as a compression means to hold the distal end of the cannula in a bullet shape. Other compression elements are available to perform this function. As shown in FIG. 12E, a smooth suture 206 may be run around the leaves of the cannula tip. To avoid injury to the polymer, the suture thread may be passed through fabric. The ends of the suture thread could be pulled to compress the distal end of the cannula and then passed down the inflow tube 10. The suture 206 may be held tight until the cannula is inside the left atrium. The suture 206 may then be released to allow the distal end of the cannula to expand into the final configuration. One end of the suture thread could be pulled until the entire suture is removed from the system at the end of the procedure.

A suture could also be used to help retain the leaves in a closed system and hold the leaves to a dilator tip so they do not become separated. A suture loop could also be used temporarily to hold the dilator tip to the inflow tube 10 during the insertion procedure.

Another compression means is depicted in FIG. 13. In FIG. 13A, a coil is shown inside the distal end of the inflow tube 10. The natural shape of the distal end of the cannula is a trumpet or flare (see FIGS. 8C and 8D). The cannula is formed from silicone with a spiral channel inside that accommodates a wire spring that can be pulled out of the proximal end of the cannula. In FIG. 13A, the wire spring is shown being held by a forceps, but this could be any compression element. Upon release of the wire, it follows the track inside the distal end which then begins to unfold.

Figure 13A:
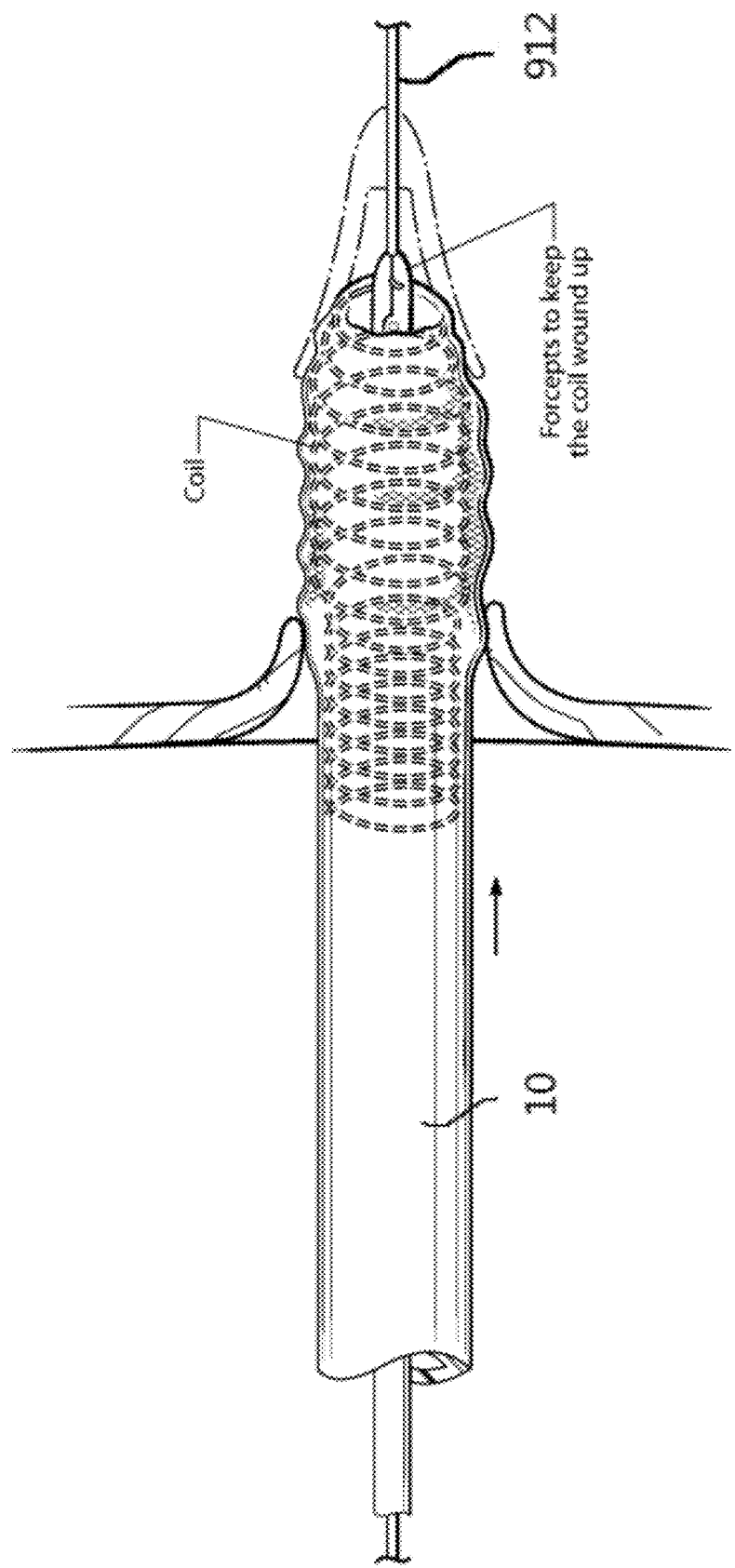
FIGS. 13A-13B are longitudinal cross-sectional views of another exemplary cannula system and an exemplary method of placing the cannula system into fluidic communication with a chamber of an organ.
Figure 13B:
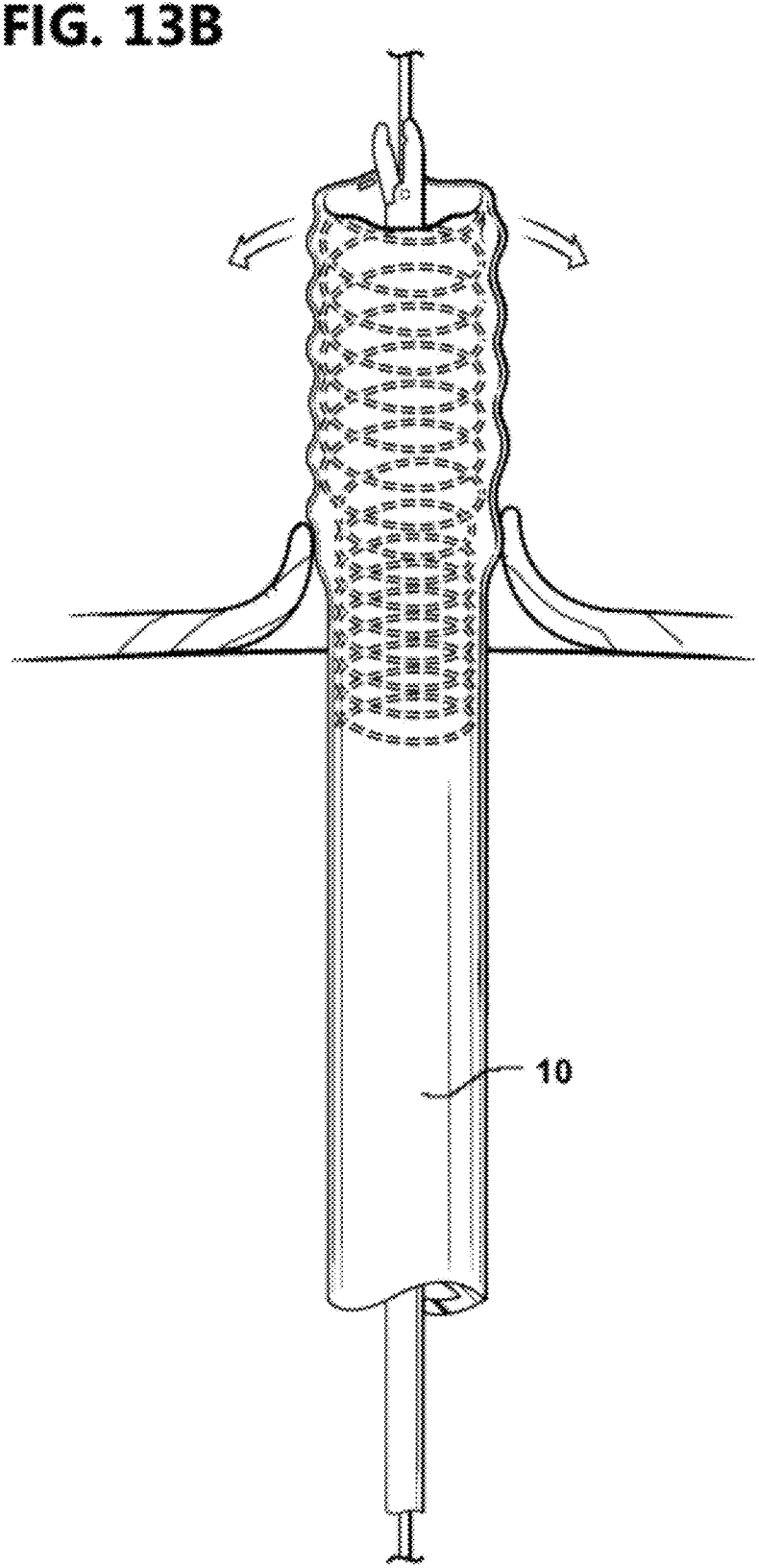
Figure 13C:
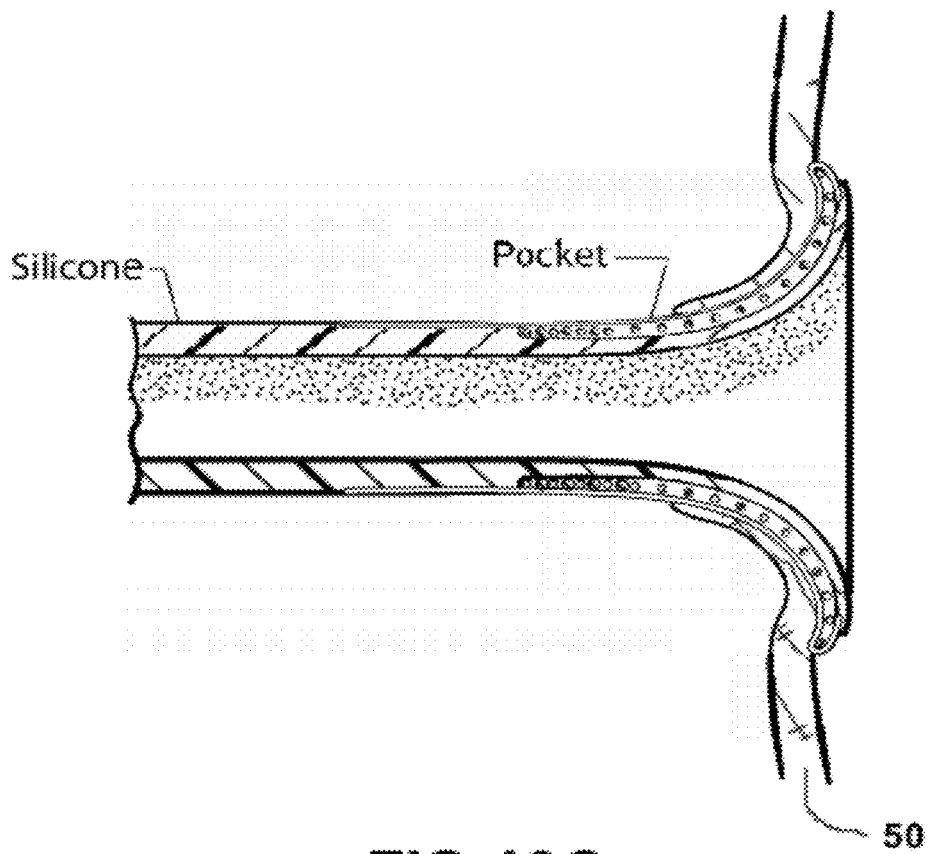
FIG. 13C is a cross-sectional view of another exemplary cannula system in fluidic communication with a chamber of an organ.
Figure 13D:
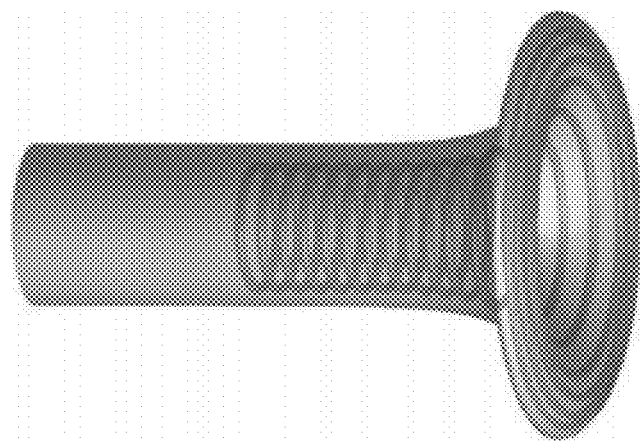
FIG. 13D is a three-dimensional rendering of another exemplary cannula.

FIG. 13C shows a longitudinal cross section after the distal end of the inflow tube 10 has achieved its second final configuration and the inflow tube 10 is in fluid communication with the organ. FIG. 13D is a three-dimensional rendering of this embodiment.

Attaching an artificial device inside the circulation preferably entails more than just providing a smooth surface on the artificial device. The interface of the heart tissue and the artificial material is often the site of clot formation as the artificial material does not easy heal or incorporate into the heart tissue. Unfortunately clots may be formed and released repeatedly. The clots can travel anywhere in the body. Fortunately, many lessons have been learned from multiple years of experience with heart valves. Valves are typically attached to the heart tissue with fabrics such as Dacron or Teflon. The artificial valve is held inside the fabric—which serves as a buffer for tissue ingrowth into the valve. The same principle of using a fabric to interface between a cannula system and the heart tissue will also prevent tissue growing into the cannula system.

Fabrics such as Teflon or Dacron are typically used for this purpose. Although a fabric is often used, roughened surfaces can be produced on otherwise smooth materials by adding a texture (roughening) to a plastic or by sintering a smooth metallic surface. The principal is to promote tissue ingrowth by altering the surface to encourage native tissue to fill spaces in the implanted material in order to close the gap between the patient's tissue and the implanted device.

FIG. 14 provides an enlarged view of how a fabric 804 or roughened surface may be added to the distal end of a hollow retention member 124/inflow tube 10 at the tissue interface. The combination of the smooth material of the cannula system, a material (such as a fabric) at the tissue interface and strong approximation to the heart tissue to hold it without risk of motion, to encourage tissue ingrowth into the material (by trapping the tissue between the cannula tip and the external retaining element) are prerequisites for excellent biologic compatibility.

Figure 14A:
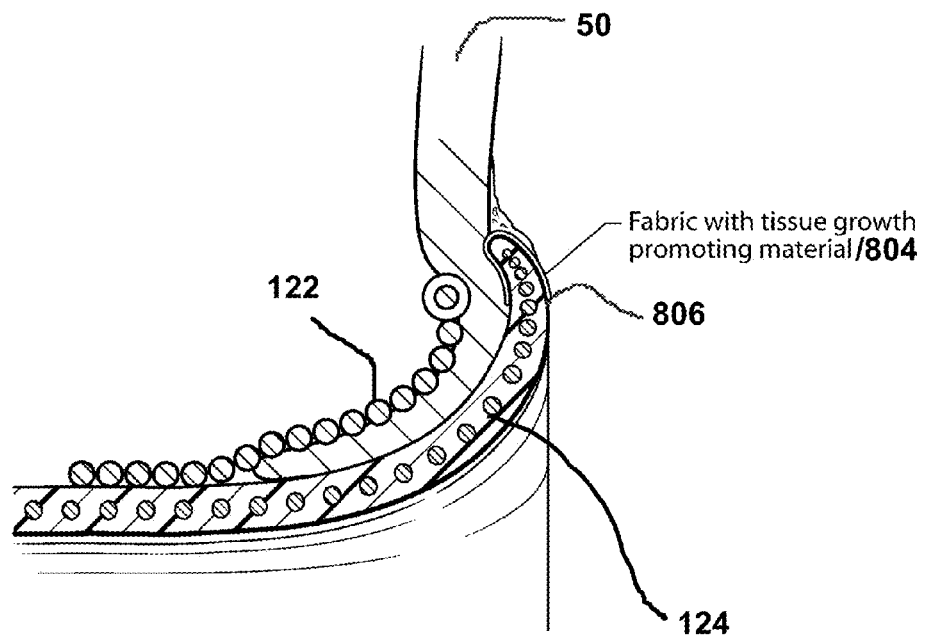
FIGS. 14A-14C are enlarged cross-sectional views of an organ wall trapped between alternative embodiments of a retaining element and the outer surface of a retention member.
Figure 14B:
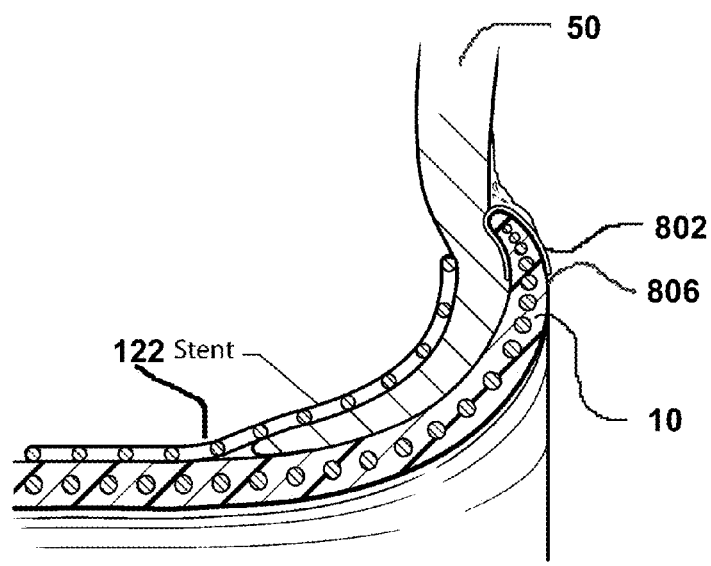

An exemplary retaining means is also shown in FIG. 14A. The atrial tissue is deformed between the outer surface of the distal end of the hollow retention member/cannula and the retaining element 122 in such a way as to produce a solid and uninterrupted contact between the atrial tissue and the outer surface of the distal end around the entire perimeter. FIG. 14B shows a stent as a retaining element.

The junction between a rough surface (such as a fabric coated surface) and a smooth surface (such as a urethane, silicone, pyrolytic carbon or a metal) can cause a risk to the patient. If the junction is in one plane, there is a risk that tissue will grow from the rough surface and onto the smooth surface. As the tissue does not adhere well to the smooth surface, the tissue traveling onto this smooth surface can break off and embolize—carrying the same risks to the patient as a blood clot. To avoid this problem, a step can be formed at the junction between the rough surface and the smooth surface. It is unusual for tissue to travel onto a smooth surface when there is a sharp change in direction at such a junction from rough to smooth surfaces.

Figure 14C:
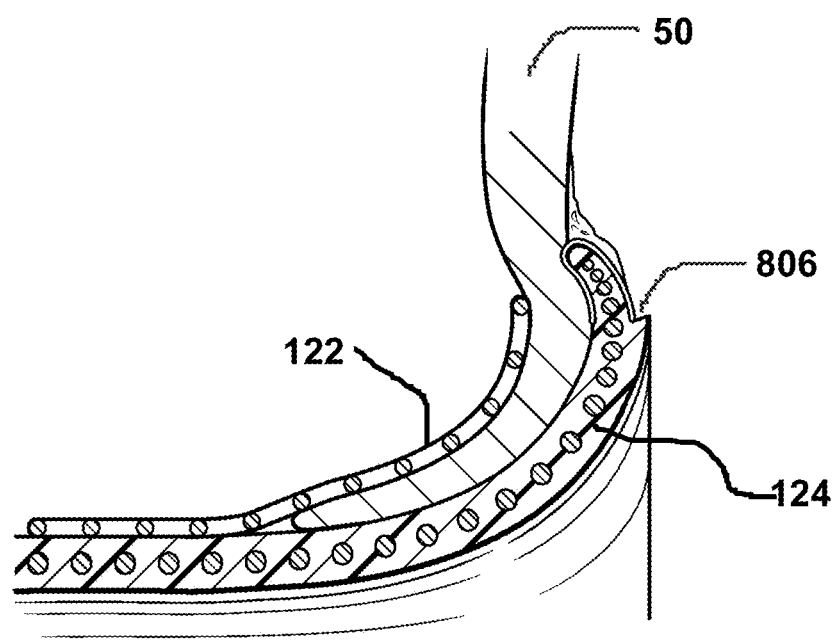

FIG. 14C depicts a cross-sectional view of a step 806 at the junction of the fabric or roughened surface and the cannula to avoid the growth of tissue at the junction point.

There are many ways to create a step. The fabric could be disposed only on the side of the flared distal end that touches the atrial wall and the polymer such as silicon could be disposed on top of the fabric so that a step is created at their junction.

In order to improve the ability of the flow of material through the cannula system, it may be useful to be able to adjust the position of the elongate tubular member 110/singular inflow tube 10. A method for adjusting the cannula system is shown in FIG. 15, wherein the elongate tubular member has cables imbedded in the walls to steer and adjust the angle of the distal end of the elongate tubular member.

Figure 15A:
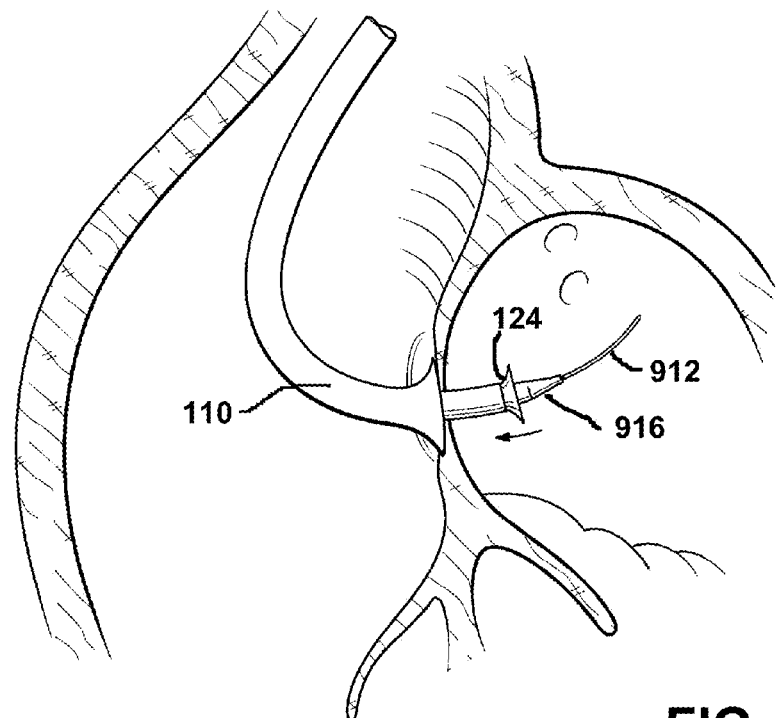
FIGS. 15A-15D are diagrammatic views of a method of adjusting the orientation of the tubular member of another exemplary cannula system.
Figure 15B:
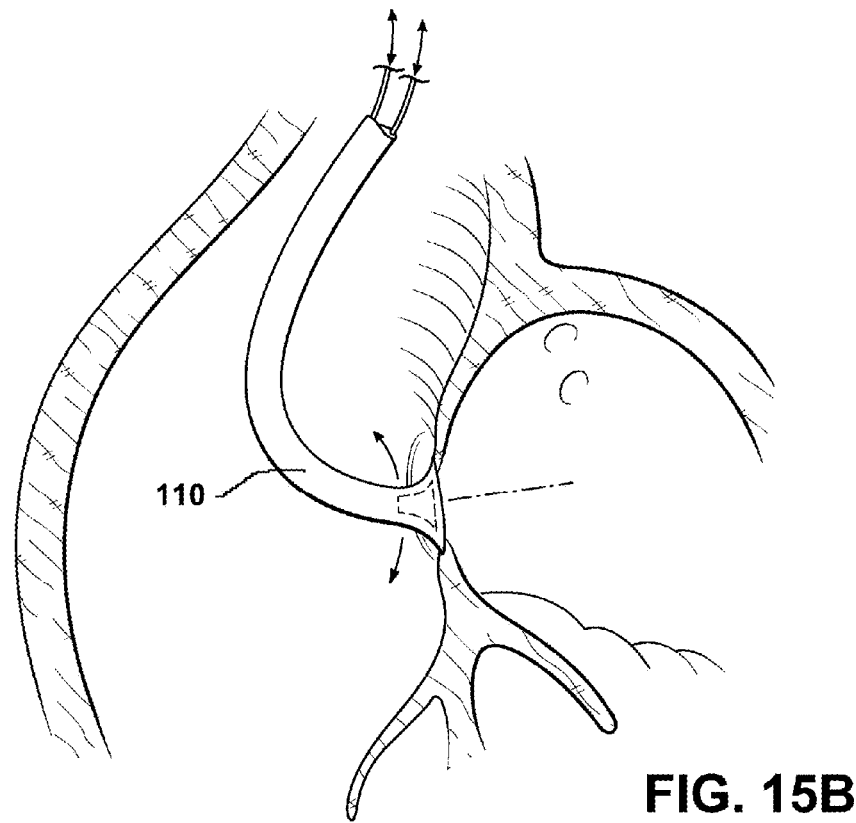

In FIG. 15A, a cannula system is being placed in fluidic communication with the left atrium of a heart with an elongate tubular member 110 anchored outside of the left atrium and with a hollow retention member 124 comprising a self expanding stent disposed in the chamber as previously shown, see, e.g., FIG. 3. In FIG. 15B, the cannula system has been secured in position.

Figure 15C:
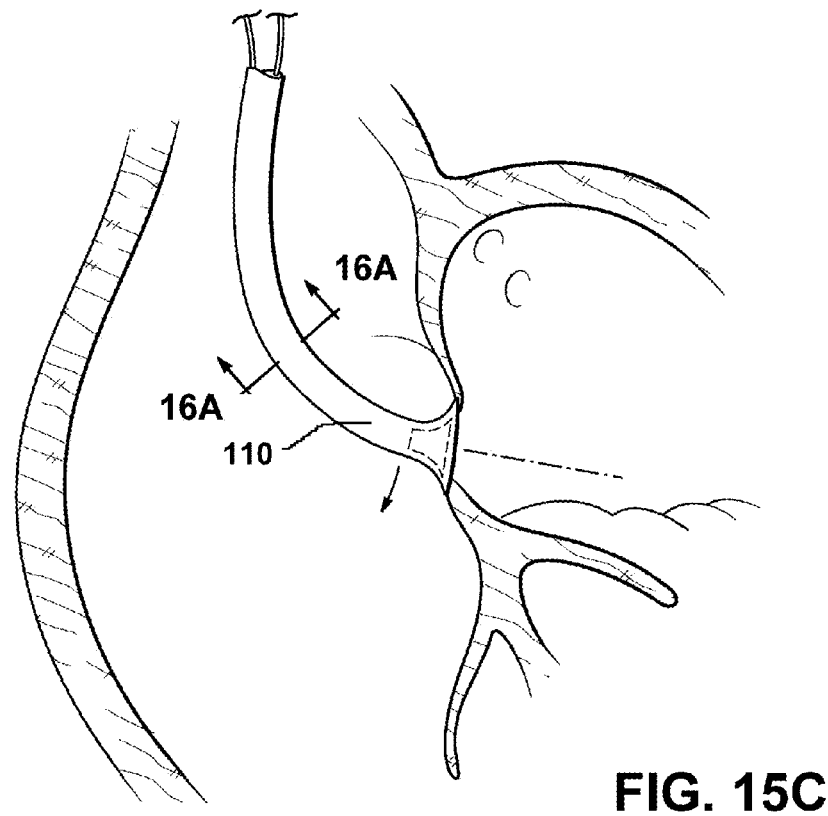
Figure 15D:
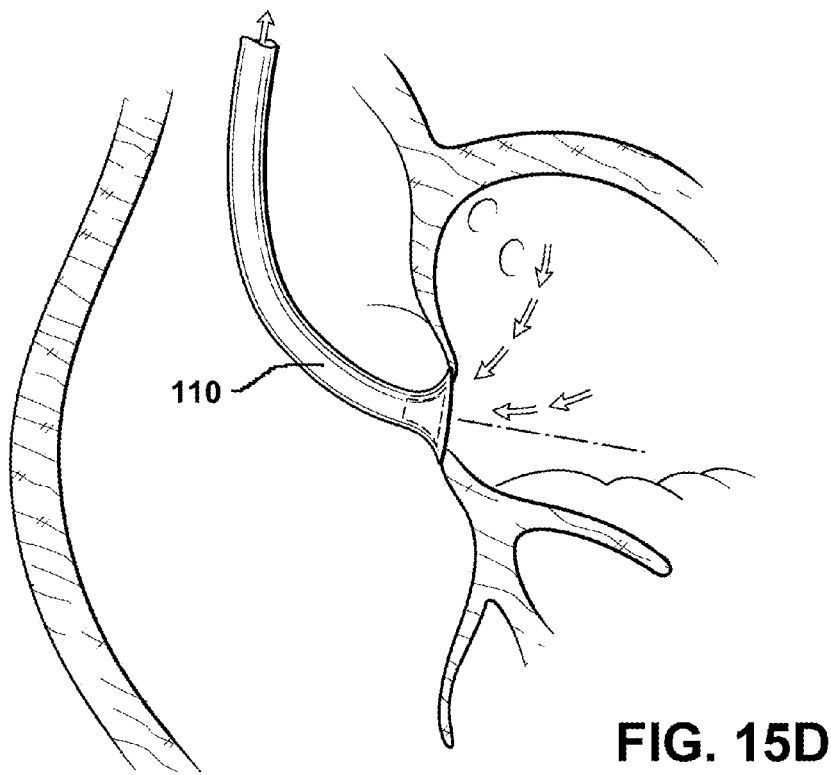

In FIGS. 15C and 15D, the position of the distal end of the elongate tubular member has been adjusted with the cables slightly downward toward the mitral valve and reduce the risk of suctioning the atrial tissue into the mouth of the system. Cables are commonly used in the wall of a catheter. The cables are tensioned and loosened from the end of the cannula outside the patient. Typically the cables are fixed at the end of the cannula inside the patient and are attached to a push/pull mechanism or a rotating handle to tension and loosen them thereby adjusting the tip location.

"Stiffeners" inside the cannula system, particular the elongate tubular member may aid in the methods of placing a cannula system in fluidic communication with an organ as described above. Stiffeners are generally known as trochars, and are often formed of metals that are malleable and allow a surgeon to generally form the shape of the cannula for insertion. After the cannula is placed, they are removed. In some embodiments, a dilator tip may serve as a trochar—it could have sufficient rigidity to serve as a stiffener to introduce the system, but the operator could bend it to a shape that makes it easy to enter the heart. In a form like this embodiment, the dilator could have central lumen to allow it to be guided over a wire. Many trochars are solid—they have no central lumen. In this case the surgeon pushes the trochar tip through the tissue directly (without the benefit of guidance over a wire). A variation of the dilator shown in these figures that retains the tip of the cannula for entry in the heart could also be formed without a central lumen.

In one embodiment, a cannula system, particularly the elongate tubular member will have to make a variety of turns inside the body to reach a pump. In one embodiment, such elongate tubular member comprises circumferential thickenings or ribs to give more stiffness to the elongate tubular member (prevent collapse) and to allow the cannula to make turns and bends without kinking the internal lumen. The ribs could be circular, linear or spiral or a combination. In another embodiment, the cannula system, particularly the elongate tubular member is externally reinforced with wire or polymers to prevent collapse and to help them maintain a desired pathway inside the body. Reinforcement elements may be wires or plastics that form spiral shapes or sleeves around the elongate tubular member.

Additionally, to give shape to the cannula system, longitudinal channels may be made in the wall of the cannula system members and elements to allow the passage of wires or shape retaining structures to force the system to follow a particular direction. The wires could be malleable. The wires or shaping elements could also be removable from these channels. This could allow softer, stiffer or different shapes to be placed in the wall of the cannula.

Figure 16A:
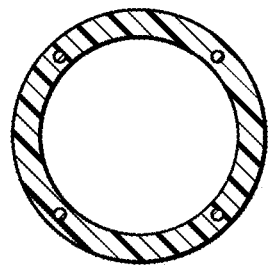
FIGS. 16A-16B are cross-sectional views of the tubular member of FIGS. 15A-15DD, taken along the line 16A-16A of FIG. 15C.
Figure 16B:
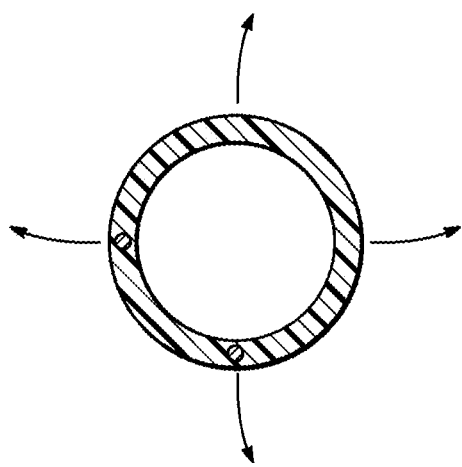

FIGS. 16A and 16B show an alternative embodiment to adjust the position of the cannula system. As shown in FIG. 16A, one embodiment uses channels inside the walls of the cannula system and to insert stiffener rods in preformed shapes to deflect the tip into a desirable shape. Rods can be preformed or can be adjusted by the user to achieve the required deflection.

FIG. 17 shows an embodiment of hollow retention member 124/distal end of a inflow tube 10 having an expanded flared, funnel or trumpet shape. The larger surface area provides a smooth path for blood, a reduced entry velocity and a lower suction pressure to entice atrial tissue to be suctioned into the cannula system.

Figure 18B:
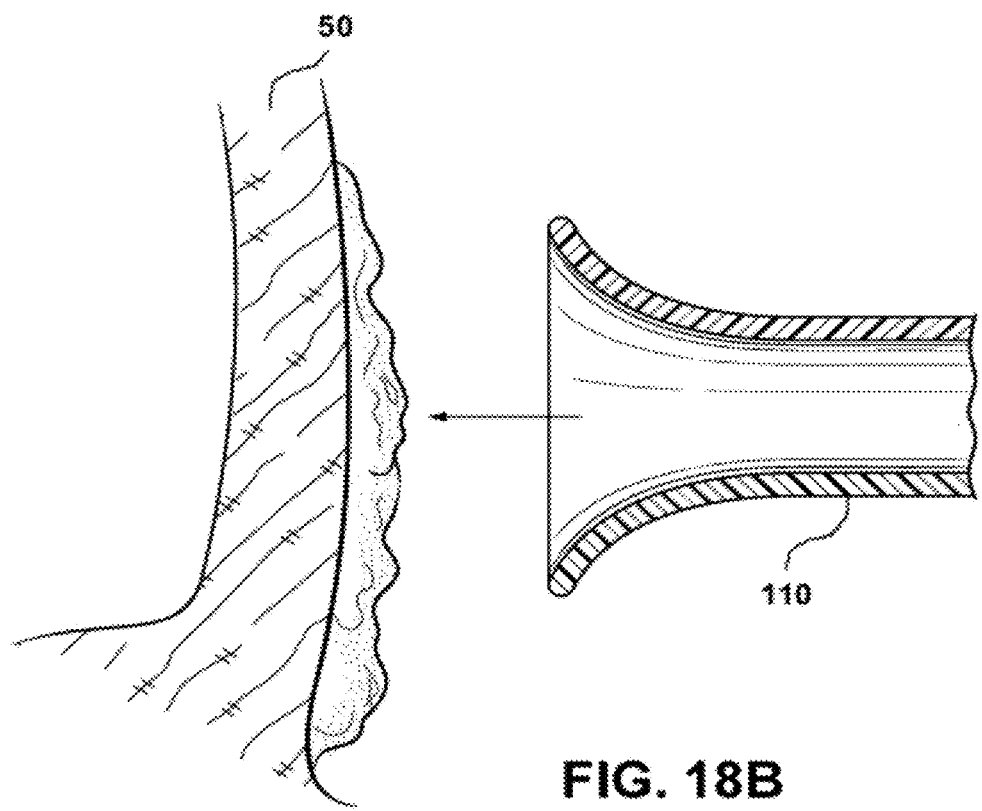
Figure 18C:
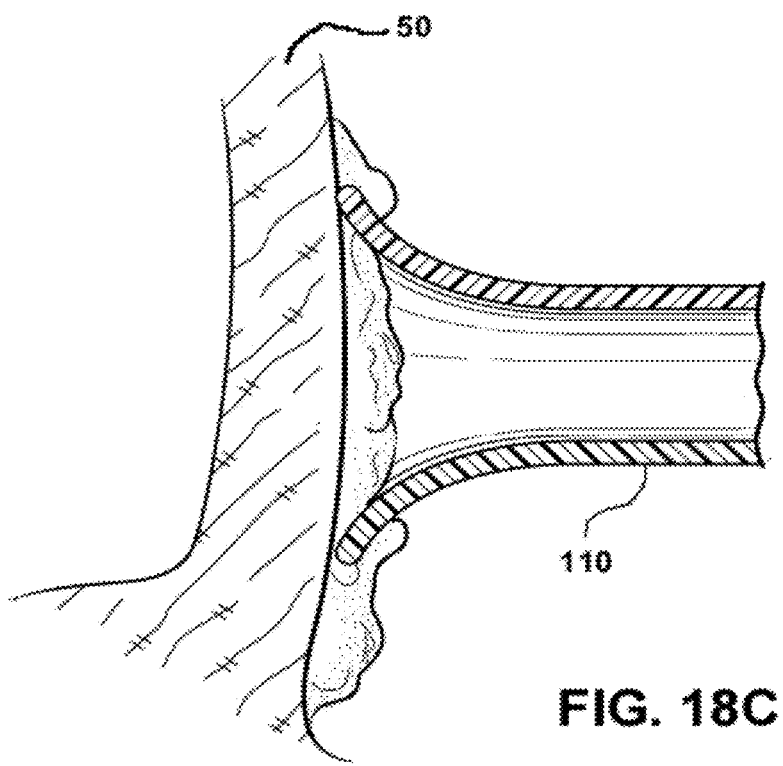
Figure 18E:
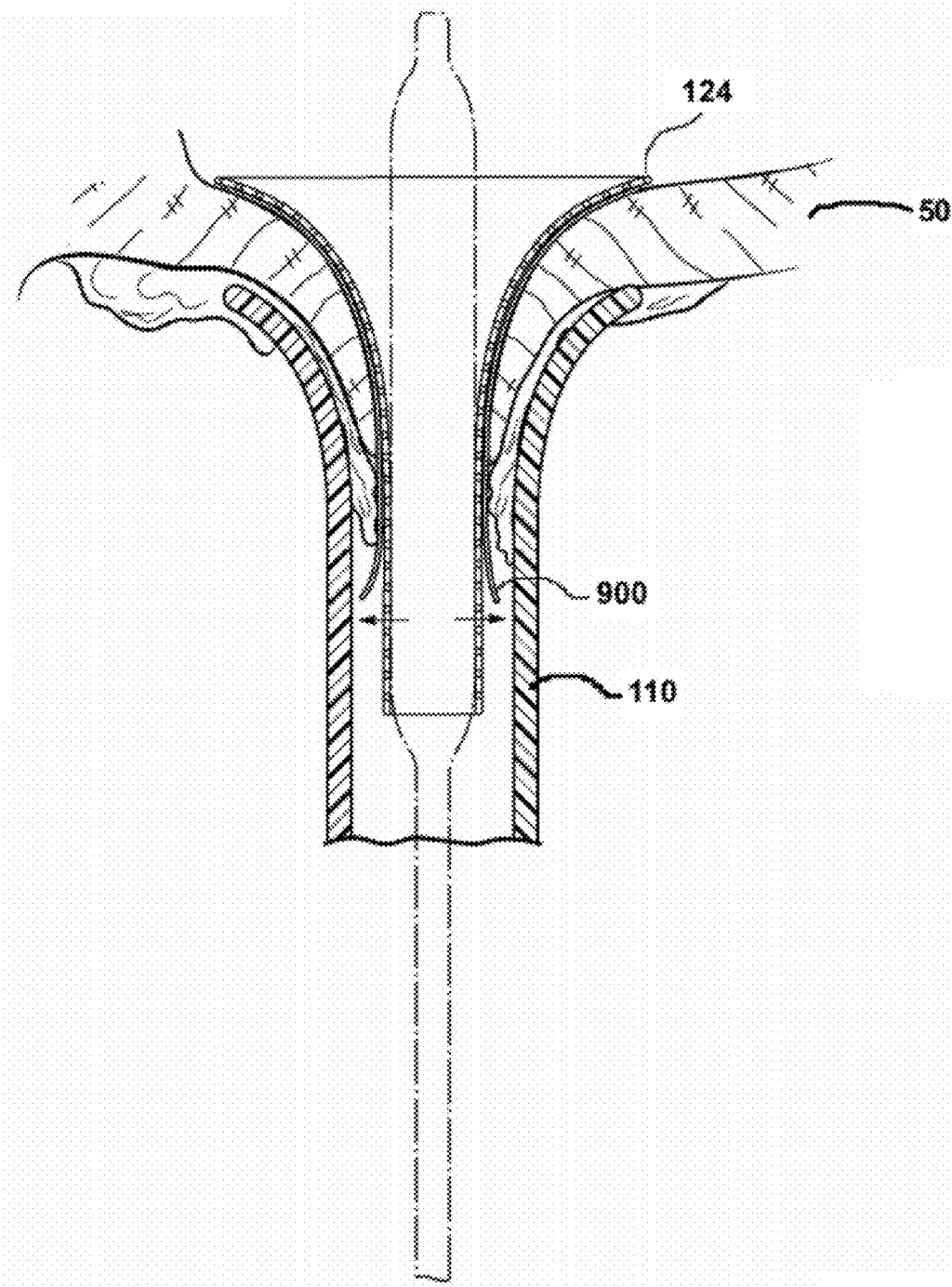
Figure 18F:
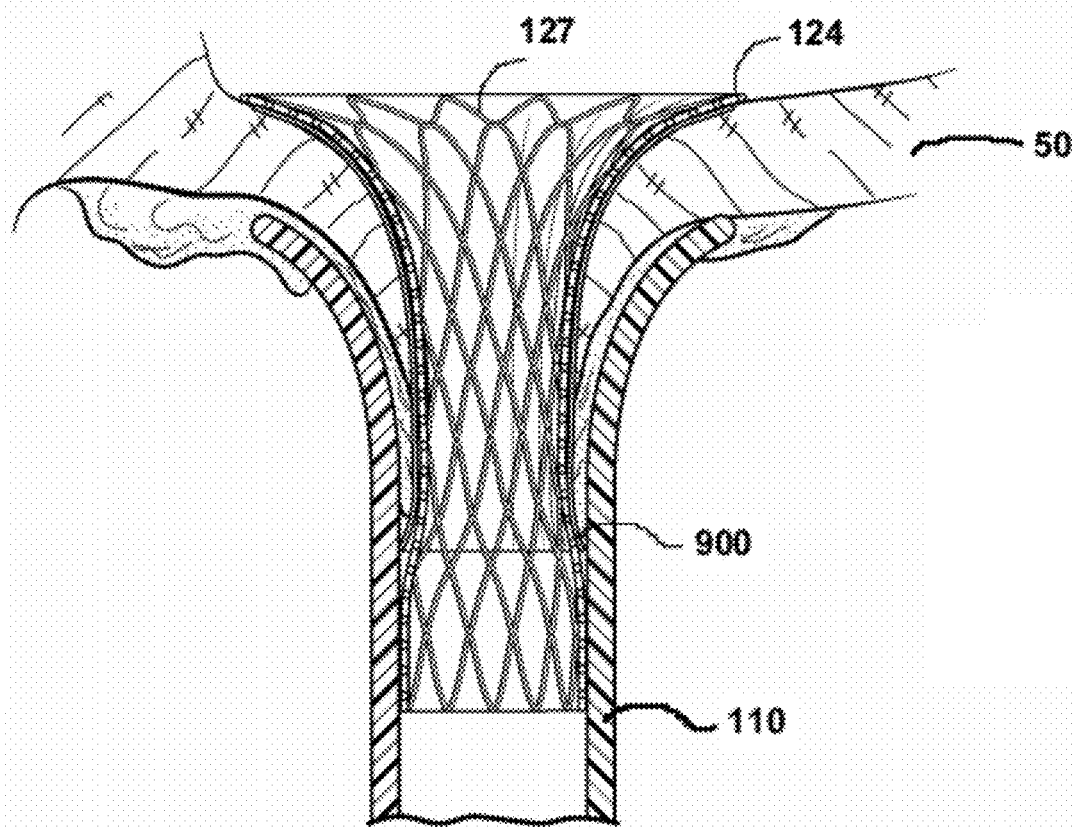

When a cannula system is placed from outside the heart, a small entry is made into the chest and the cannula is placed directly into the atrium, see, FIG. 18A The entry site is typically in the region of the entry of the two right pulmonary veins. This area is often covered with tissue and fat, see, FIG. 18B. As the cannula system is attached to the atrium, fat may be brought into the cannula system and it could be sucked into the system, see, FIG. 18C to prevent embolization of fatty material, a cannula system as described herein may further comprise a "sleeve" 900 barrier configured to trap fat under it and prevent its entry into the cannula system, see, FIG. 18E. To deploy the sleeve 900, the sleeve may be positioned on a balloon such that inflation of the balloon expands the sleeve 900, which may then be disposed between the retention member 124 and the distal opening of the tubular member so that the organ wall can be trapped by the retention member and between the sleeve 900 and the distal opening of the tubular member. The blood encounters a smooth surface. The sleeve could be made from any biocompatible material.

Figure 19:
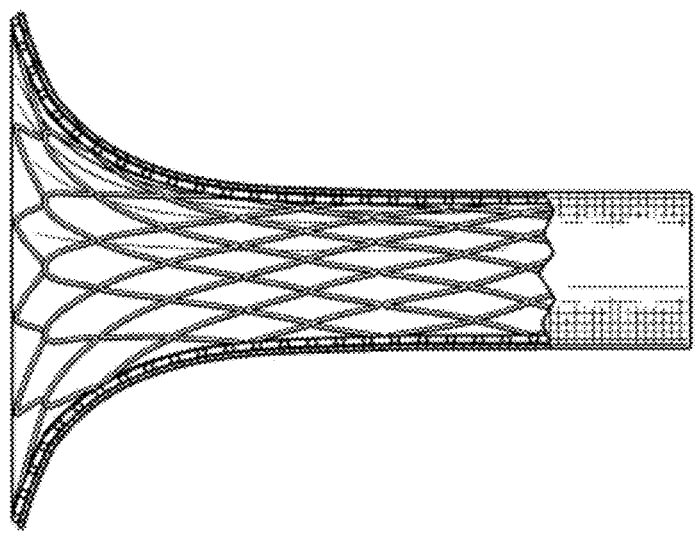
FIG. 19 is a longitudinal cross-sectional view of the cannula system of FIGS. 18B-18F with an alternative embodiment of the sleeve.

The same configuration may be achieved with a hollow retention member comprising a stent including a covering between its elongate struts, see, FIG. 19. A wide variety of "covered stents" have been used and then often employ an ePTFE covering.

All patents and patent publications referred to herein are hereby incorporated by reference.

Certain modifications and improvements will occur to those skilled in the art upon a reading of the foregoing description. It should be understood that all such modifications and improvements have been deleted herein for the sake of conciseness and readability but are properly within the scope of the following claims.

The invention claimed is:

1. An apparatus, comprising:
an elongate tubular member having a proximal end portion, a distal end portion, an inner surface and an outer surface, the inner surface defining a lumen extending between the proximal end portion and the distal end portion;
a wire coupled to the elongate tubular member such that at least a portion of the wire is disposed between the inner surface and the outer surface, the wire configured to move between a first configuration and a second configuration, the wire configured to form a flared structure at the distal end portion of the elongate tubular member when the wire is in the second configuration;
a fabric material disposed about the distal end portion of the elongate tubular member at a junction along the inner surface of the elongate tubular member, the junction forming a circumferential step between the fabric material and the elongate tubular member, the fabric material formulated to promote tissue ingrowth when the flared structure is coupled to a first side of an organ wall; and
a retaining element coupled to the elongate tubular member, the retaining element configured to contact a second side of the organ wall to couple the organ wall between the flared structure and the retaining element.

2. The apparatus of claim 1, wherein the wire forms a plurality of lobes within the flared structure at the distal end portion of the elongate tubular member, the plurality of lobes disposed circumferentially about the lumen.

3. The apparatus of claim 1, wherein the wire forms a zig zag shape within the flared structure.

4. The apparatus of claim 1, wherein the wire is constructed from a shape memory material.

5. The apparatus of claim 1, further comprising:
a compression member coupled to the distal end portion of the elongate tubular member, the compression member configured to maintain the wire in its first configuration.

6. The apparatus of claim 1, wherein the wire and the retaining element are collectively configured to anchor the flared structure to the first side of the organ wall to form a fluid-tight seal.

7. The apparatus of claim 1, wherein the retaining element includes a surface configured to contact the second side of the organ wall without puncturing the organ wall.

8. The apparatus of claim 1, wherein the fabric material includes a roughened surface configured to promote tissue ingrowth.

9. The apparatus of claim 1, wherein the fabric material includes at least one of polytetrafluoroethylene or polyethylene teraphthalate.

10. The apparatus of claim 1, wherein:
at least the inner surface of the elongate tubular member is constructed from a polymer; and
the junction is configured to retard tissue growth at the inner surface of the elongate tubular member.

11. The apparatus of claim 1, wherein the junction forms a discontinuous surface.

12. The apparatus of claim 1, wherein the junction forms a circumferential step that surrounds the lumen.

13. The apparatus of claim 1, wherein the elongate tubular member is constructed from a polymer including at least one of silicone, urethane or polyurethane.

* * * * *